(12) United States Patent
Strangeman et al.

(10) Patent No.: US 12,343,184 B2
(45) Date of Patent: Jul. 1, 2025

(54) PATIENT POSITIONING SYSTEM

(71) Applicant: LEO CANCER CARE, INC., Middleton, WI (US)

(72) Inventors: Mark Strangeman, West Sussex (GB); Ralf Spriestersbach, Athens (GR); Paul Dixon, Surrey (GB); Tony Westwood, East Sussex (GB); Darren Forcey, Brighton (GB); Stephen Towe, East Sussex (GB)

(73) Assignee: LEO CANCER CARE, INC., Middleton, WI (US)

( * ) Notice: Subject to any disclaimer, the term of this patent is extended or adjusted under 35 U.S.C. 154(b) by 337 days.

(21) Appl. No.: 17/894,335

(22) Filed: Aug. 24, 2022

(65) Prior Publication Data

US 2023/0172566 A1 Jun. 8, 2023

Related U.S. Application Data

(60) Provisional application No. 63/237,513, filed on Aug. 26, 2021.

(51) Int. Cl.
*A61B 6/04* (2006.01)
*A61B 6/00* (2024.01)

(52) U.S. Cl.
CPC .......... *A61B 6/0407* (2013.01); *A61B 6/0421* (2013.01); *A61B 6/0487* (2020.08); *A61B 6/04* (2013.01)

(58) Field of Classification Search
CPC ... A61B 6/0407; A61B 6/0421; A61B 6/0487; A61B 6/04; A61G 7/002; A61G 7/015; A61G 7/018; A61G 7/109; A61G 7/1096; A61G 7/1098; A61G 13/02; A61G 13/08; A61G 13/123; A61G 13/1245; A61G 13/125
USPC .......... 5/601, 600, 613, 616–618, 648, 651; 378/208, 209
See application file for complete search history.

(56) References Cited

U.S. PATENT DOCUMENTS

| 5,161,274 A | 11/1992 | Hayes et al. |
| 6,547,809 B1 | 4/2003 | Cuccia |
| 7,466,792 B2 | 12/2008 | Bakai et al. |
| 7,761,942 B2 | 7/2010 | Benzo et al. |

(Continued)

FOREIGN PATENT DOCUMENTS

| AU | 2018337070 B9 * | 7/2024 | ............. A61B 5/055 |
| AU | 2024205499 A1 * | 8/2024 | ............. A61B 5/055 |

(Continued)

OTHER PUBLICATIONS

Boisbouvier, S. et al. Upright patient positioning for pelvic radiotherapy treatments. Tech Innov Patient Support Radiat Oncol. Nov. 28, 2022;24:124-130.

(Continued)

*Primary Examiner* — Robert G Santos
(74) *Attorney, Agent, or Firm* — Casimir Jones, S.C.; Thomas A. Isenbarger; Thomas J. Lyneis

(57) ABSTRACT

Provided herein is technology relating to medical imaging and radiation therapy and particularly, but not exclusively, to devices, methods, and systems for positioning a patient with respect to a radiation source to image the patient and/or to treat the patient by exposing the patient to a radiation beam produced by the radiation source.

17 Claims, 28 Drawing Sheets

(56) References Cited

U.S. PATENT DOCUMENTS

| | | | |
|---|---|---|---|
| 8,712,012 B2 | 4/2014 | O'Connor | |
| 11,529,109 B2 * | 12/2022 | Feain | A61B 6/0478 |
| 11,918,397 B2 * | 3/2024 | Harper | A61B 34/10 |
| 2004/0220467 A1 | 11/2004 | Bonutti | |
| 2011/0218430 A1 | 9/2011 | Balakin | |
| 2012/0324648 A1 | 12/2012 | Amano | |
| 2013/0064344 A1 | 3/2013 | Carol | |
| 2019/0117483 A1 | 4/2019 | Tessmer et al. | |
| 2020/0268327 A1 | 8/2020 | Feain et al. | |
| 2022/0183641 A1 | 6/2022 | Harper et al. | |
| 2023/0172566 A1 * | 6/2023 | Strangeman | A61B 6/0421 5/601 |
| 2023/0172567 A1 * | 6/2023 | Feain | A61B 6/107 |
| 2024/0252129 A1 * | 8/2024 | Harper | A61B 6/447 |

FOREIGN PATENT DOCUMENTS

| | | | | |
|---|---|---|---|---|
| WO | WO-2019056055 A1 * | 3/2019 | | A61B 5/055 |
| WO | WO-2023028102 A1 * | 3/2023 | | A61B 6/0407 |
| WO | WO-2024035695 A2 * | 2/2024 | | A61N 5/1075 |
| WO | WO-2024151806 A1 * | 7/2024 | | A61N 5/1075 |
| WO | WO-2024233522 A2 * | 11/2024 | | A61B 6/0487 |

OTHER PUBLICATIONS

Eslick E.M. et al. The Nano-X Linear Accelerator: A Compact and Economical Cancer Radiotherapy System Incorporating Patient Rotation. Technol Cancer Res Treat. Oct. 2015;14(5):565-72.

International Search Report and Written Opinion for PCT/US2022/041313, 17 pages.

Jinzaki, M. et al. Development of Upright Computed Tomography With Area Detector for Whole-Body Scans: Phantom Study, Efficacy on Workflow, Effect of Gravity on Human Body, and Potential Clinical Impact. Invest Radiol. Feb. 2020;55(2):73-83.

Rahim et al. Upright Radiation Therapy—A Historical Reflection and Opportunities for Future Applications. Front Oncol. Feb. 25, 2020;10:213.

Schreuder, N. et al. Fixed beamlines can replace gantries for particle therapy. Med Phys. Apr. 2022;49(4):2097-2100.

U.S. Appl. No. 63/396,444, filed Aug. 9, 2022, Towe et al.

U.S. Appl. No. 63/399,862, filed Aug. 22, 2022, Towe et al.

Yamada, Y. et al. Differences in Lung and Lobe Volumes between Supine and Standing Positions Scanned with Conventional and Newly Developed 320-Detector-Row Upright CT: Intra-Individual Comparison. Respiration. 2020;99(7):598-605.

Supplementary European Search Report for European Application No. 22862014.2, mailed Apr. 22, 2025, 09 Pages.

* cited by examiner

PATIENT POSITIONING SYSTEM

This application claims priority to U.S. provisional patent application Ser. No. 63/237,513, filed Aug. 26, 2021, which is incorporated herein by reference in its entirety.

FIELD

Provided herein is technology relating to medical imaging and radiation therapy and particularly, but not exclusively, to devices, methods, and systems for positioning a patient with respect to a radiation source to image the patient and/or to treat the patient by exposing the patient to a radiation beam produced by the radiation source.

BACKGROUND

Radiation sources have many uses in medicine, including medical imaging and radiation therapy. Generally, radiation sources are configured to move in relation to a stationary patient, e.g., to expose a specific part or region of the patient to radiation produced by the source. Further, while radiation therapy and the associated diagnostic and planning imaging are conventionally performed with patients in prone or supine horizontal positions, some patients benefit from therapy while in an unconventional position, such as an upright position. However, limitations in acquiring upright imaging data to plan upright therapy have hindered adoption and use of beneficial upright radiotherapy methods. For example, upright positioning systems have been demonstrated to have reduced positional reproducibility relative to horizontal patient positioning. See, e.g., Rahim et al. (2020) Frontiers in Oncology 10, article 213, incorporated herein by reference. Some previous technologies developed to meet this need provide a patient positioning system that is configured to maintain the position of a patient in an upright, stable position to maximize patient comfort and to minimize patient movement that could reduce image quality. See, e.g., U.S. Pat. App. Pub. No. 20200268327, which is incorporated herein by reference.

SUMMARY

The technology provided herein relates to several aspects of a patient positioning system for medical imaging and/or radiation therapy. In some embodiments, the technology described herein supplements and/or modifies a patient positioning apparatus and/or a patient support, e.g., as described in U.S. Pat. App. Pub. No. 20200268327, which is incorporated herein by reference. In some embodiments, the patient positioning system stabilizes and supports a patent in an upright (e.g., standing, sitting, kneeling, perched) position. Imaging and/or treating patients in an upright position provides the benefits of increasing patient comfort. Further, diagnosis and/or treatment of patients in an upright position provides advantages over conventional diagnosis and/or treatment of patients in a horizontal position for many indications (e.g., lung cancer, breast cancer). While imaging and/or treating an upright patient provides diagnostic and therapeutic advantages, medical imaging and treatment needs improved patient positioning systems for stabilizing and supporting patients in a suitable upright position for delivering therapeutic radiation doses to target areas and for planning treatment using medical imaging.

In some embodiments, the technology provides a patient support. For example, in some embodiments, the patient support comprises a first support member configured to contact a patient; a second support member configured to contact the patient; and an actuation assembly coupled to the first support member and the second support member, wherein the actuation assembly is configured to move the first support member and the second support member between a first configuration and a second configuration. In some embodiments, the actuation assembly is configured to move the first support member and the second support member simultaneously between the first configuration and the second configuration. In some embodiments, the first configuration and the second configuration are customized for the patient. In some embodiments, the first configuration is a patient ingress state and the second configuration is a patient imaging or treatment state. In some embodiments, the first configuration is a patient ingress state and the second configuration is a patient standby state. In some embodiments, the first configuration is a patient standby state and the second configuration is a patient imaging or treatment state. In some embodiments, the first configuration is a patient standby state and the second configuration is a patient egress state. In some embodiments, the first configuration is a patient imaging or treatment state and the second configuration is a patient egress state.

In some embodiments, the actuation assembly includes a motor and a microprocessor. In some embodiments, the first support member is a back rest, a head rest, an arm rest, a seat member, a shin rest, or a foot brace (e.g., heel stop). In some embodiments, the patient support further includes a dynamic configuration. In some embodiments, the dynamic configuration assists ingress of the patient to the patient support. In some embodiments, the dynamic configuration assists egress of the patient from the patient support.

In some embodiments, the technology further provides a patient positioning system comprising a center beam axis; a support configured to support a patient; an actuation assembly coupled to the support and configured to move the support, wherein the support is movable along a first axis, movable along a second axis that is orthogonal to the first axis, and movable along a third axis that is orthogonal to the first axis and the second axis; wherein the support is rotatable about the first axis, the second axis, and the third axis; and wherein a desired region of the patient is aligned with the center beam axis when the support is in a first position and a second position different than the first position. In some embodiments, the support moves a first compensation amount along the first axis and a second compensation amount along the second axis in response to rotation of the support about any one of the first axis, the second axis, and the third axis. In some embodiments, a first amount of mechanical flex in the support occurs in the first position and a second amount of mechanical flex in the support occurs regardless of the size of the patient. In some embodiments, the patient positioning system further comprises a processor and a memory, wherein the memory includes a deflection correction table with a plurality of compensations to maintain the desired region aligned with the center beam axis for the support in a plurality of positions and for a plurality of patient weights.

In some embodiments, the technology provides an adjustable seat assembly. For example, in some embodiments, the technology provides an adjustable seat assembly comprising a base including a slot; a seat movably coupled to the base between a first position and a second position; a rod coupled to the seat and positioned within the slot; and a mount coupled to the base, wherein the seat slides relative to the mount and the rod slides within the slot as the seat moves between the first position and the second position. In some embodiments, the seat includes a first surface configured to support a patient and a second surface opposite the first surface, wherein the second surface is coupled to the mount. In some embodiments, the second surface is an arcuate surface. In some embodiments, the rod is offset from a rotational axis of the seat. In some embodiments, the adjustable seat assembly further comprises a cleat coupled to the seat, wherein the cleat includes a wing. In some embodiments, the mount includes a flange that is engageable with the wing of the cleat. In some embodiments, the cleat and the mount restrict vertical movement of the seat. In some embodiments, the slot is arcuate. In some embodiments, the mount includes an arcuate surface that receives the seat.

In some embodiments, the technology provides a system comprising a patient support assembly in a first configuration; and an adjustor configured to move the patient support assembly in a first direction while the patient support assembly remains in the first configuration. In some embodiments, the adjustor includes a first block and a second block movable with respect to the first block. In some embodiments, the adjustor includes a first sheet positioned between the first block and the second block, and a second sheet positioned on the second block. In some embodiments, the adjustor includes a groove defined between the first block and the second block; wherein the groove is configured to receive wedges to adjust the position of the second block relative to the first block. In some embodiments, the adjustor is a first adjustor, and the system further includes a second adjustor and a third adjustor. In some embodiments, the first adjustor sets a first position of the patient support assembly in a first direction; and the second adjustor and the third adjustor set a second position of the patient support assembly in a second direction.

In some embodiments, the technology provides a patient positioning system comprising a platform; a load cell coupled to the platform, wherein the load cell generates an output based on the weight of the platform and a weight supported on the platform; and a processor configured to receive the output and determine the weight supported on the platform. In some embodiments, the load cell includes a strain gauge. In some embodiments, the load cell is positioned between the platform and a chain drive. In some embodiments, the chain drive includes a chain and a support member coupled to an end of the chain, and the support member is configured to receive a portion of the load cell. In some embodiments, the support member includes a notch to receive the portion of the load cell. In some embodiments, the processor is further configured to determine a location on the platform where the weight is supported. In some embodiments, the processor is further configured to detect a change in the weight supported on the platform. In some embodiments, the processor controls movement of a portion of the patient positioning system in response to the detected weight supported on the platform.

In some embodiments, the technology provides a patient support assembly comprising a base including a receptacle and a first pad positioned within the receptacle; and a support member including a tongue with a second pad, the tongue removably received within the receptacle to couple the support member with the base, wherein the second pad directly engages the first pad when the tongue is received within the receptacle. In some embodiments, the first pad is nylon. In some embodiments, the second pad is nylon. In some embodiments, the first pad includes a first beveled edge, and the second pad includes a second beveled edge. In some embodiments, the first pad is positioned on a first side of the receptacle, the receptacle further including a third pad positioned on a second side of the receptacle, opposite the first side; and wherein the tongue includes a fourth pad that directly engages the third pad when the tongue is received within the receptacle. In some embodiments, the support member further includes a first rod and a second rod. In some embodiments, the tongue is positioned between the first rod and the second rod. In some embodiments, the first rod and the second rod extend in a direction parallel to the tongue. In some embodiments, the base includes a first block with a first bore and a second block with a second bore, wherein the first rod is received within the first block and the second rod is received within the second block when the tongue is received within the receptacle. In some embodiments, the first block permits adjustment in a first direction, and the second block permits adjustment in a second direction orthogonal to the first direction.

In some embodiments, the technology provides a patient positioning system comprising a base; a platform comprising a patient support; a scissor frame coupled to the base and the platform; and a chain drive coupled to the base and the platform, wherein the chain drive is configured to move the platform between a retracted position and an extended position. In some embodiments, the platform is a first distance from the base in the retracted position and the platform is a second distance from the base in the extended position, the second distance being larger than the first distance. In some embodiments, the scissor frame includes a first upper mount and a second upper mount coupled to the platform, wherein the first upper mount is slidable with respect to the platform. In some embodiments, the scissor frame includes a first lower mount and a second lower mount coupled to the base, wherein the first lower mount is slidable with respect to the base. In some embodiments, the chain drive includes a chain with a plurality of links, wherein the plurality of links include an interlocking profile. In some embodiments, the scissor frame is a first scissor frame, and the chain drive is a first chain drive, wherein the patient positioning system further includes a second scissor frame coupled to the platform and a second chain drive coupled to the platform.

In some embodiments, the technology provides a conformable patient support comprising: an outer layer; an interior cavity including a first section, a second section, and a dividing member positioned between the first section and the second section; a first plurality of beans (e.g., polymer (e.g., polystyrene, expanded polystyrene (EPS), expanded polypropylene (EPP), STYROFOAM, etc. beads or beans having a diameter of approximately 2 mm to 10 mm) positioned within the first section; and a second plurality of beans positioned within the second section, wherein the first section is positioned above the second section when the conformable patient support is oriented to conform to a patient in an upright position. In some embodiments, the technology provides methods related to the conformable patient support. For example, in some embodiments, the technology provides a method of conforming a bag to a patient in an upright position, said method comprising evacuating a portion of the air within a bag containing a plurality of beans; orienting the bag vertically; pressing the bag against a patient in an upright position; and evacuating a second portion of the air within the bag.

In some embodiments, the technology provides a patient positioning system comprising a movable patient support; an actuator configured to move the movable patient support; a main power supply electrically coupled to the actuator; a backup electrical circuit coupled to the actuator, the backup electrical circuit including a low voltage battery, a relay, and a brake; wherein the backup electrical circuit is configured to operate the actuator when the main power supply is disabled.

In some embodiments, the technology provides a patent positioning system comprising a floor panel comprising a drainage hole; and an integrated fluid control cassette below said floor panel, said fluid control cassette comprising an absorbent material. In some embodiments, the patient positioning system comprises a fluid control receiving aperture configured to receive the integrated fluid control cassette. In some embodiments, the patient positioning system comprises a first rail and a second rail to guide insertion of the fluid control cassette into the fluid control cassette receiving aperture and to provide support for the inserted fluid control cassette. In some embodiments, the fluid control cassette is disposable or reusable. In some embodiments, the fluid control cassette comprises an antimicrobial compound, an antiviral compound, an antibacterial compound, a disinfectant, an anti-odor compound, and/or a superabsorbent polymer.

Additional embodiments will be apparent to persons skilled in the relevant art based on the teachings contained herein.

BRIEF DESCRIPTION OF THE DRAWINGS

These and other features, aspects, and advantages of the present technology will become better understood with regard to the following drawings.

Figure 1:
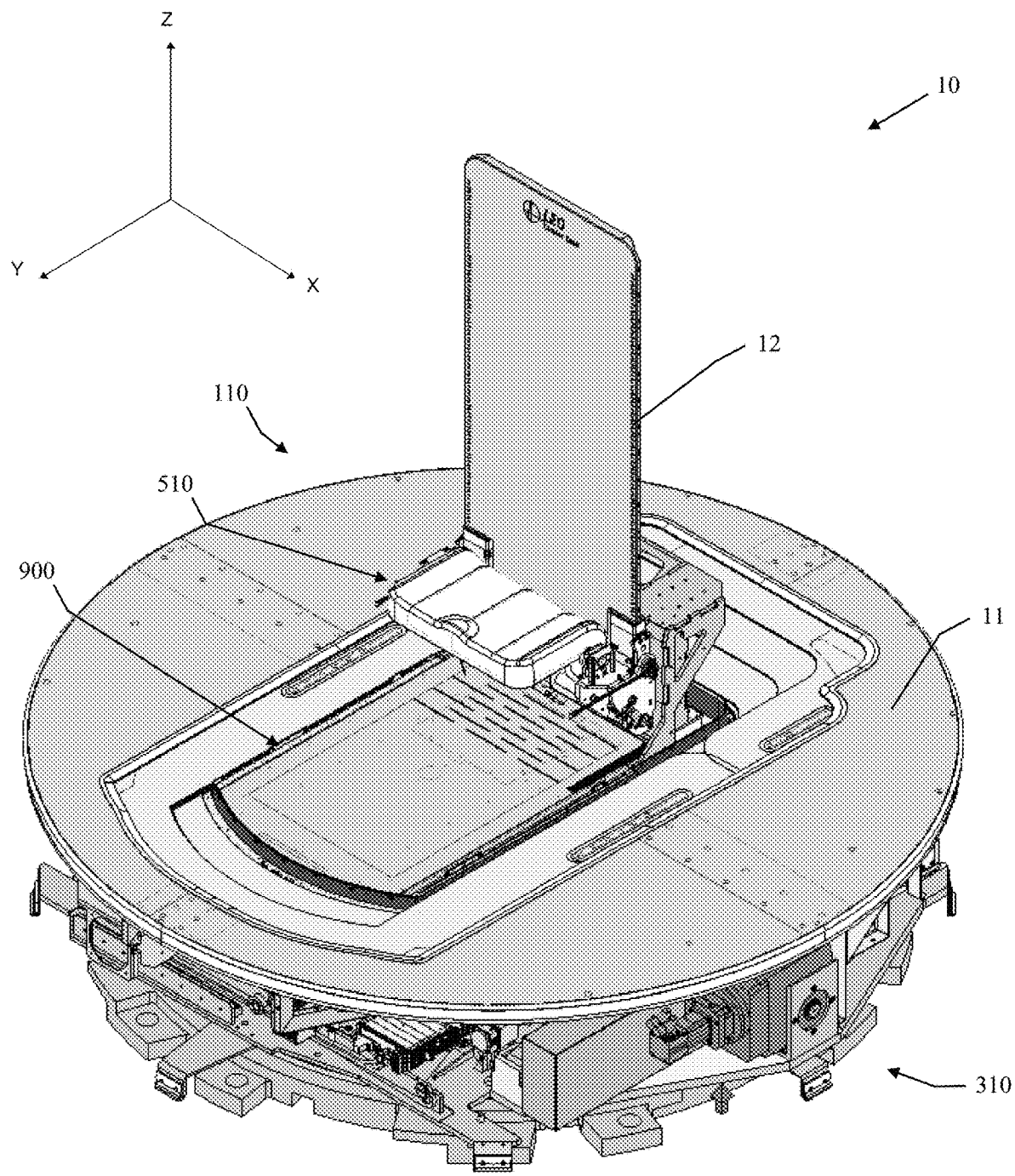
FIG. 1 is a perspective view of a patient positioning system.
Figure 2:
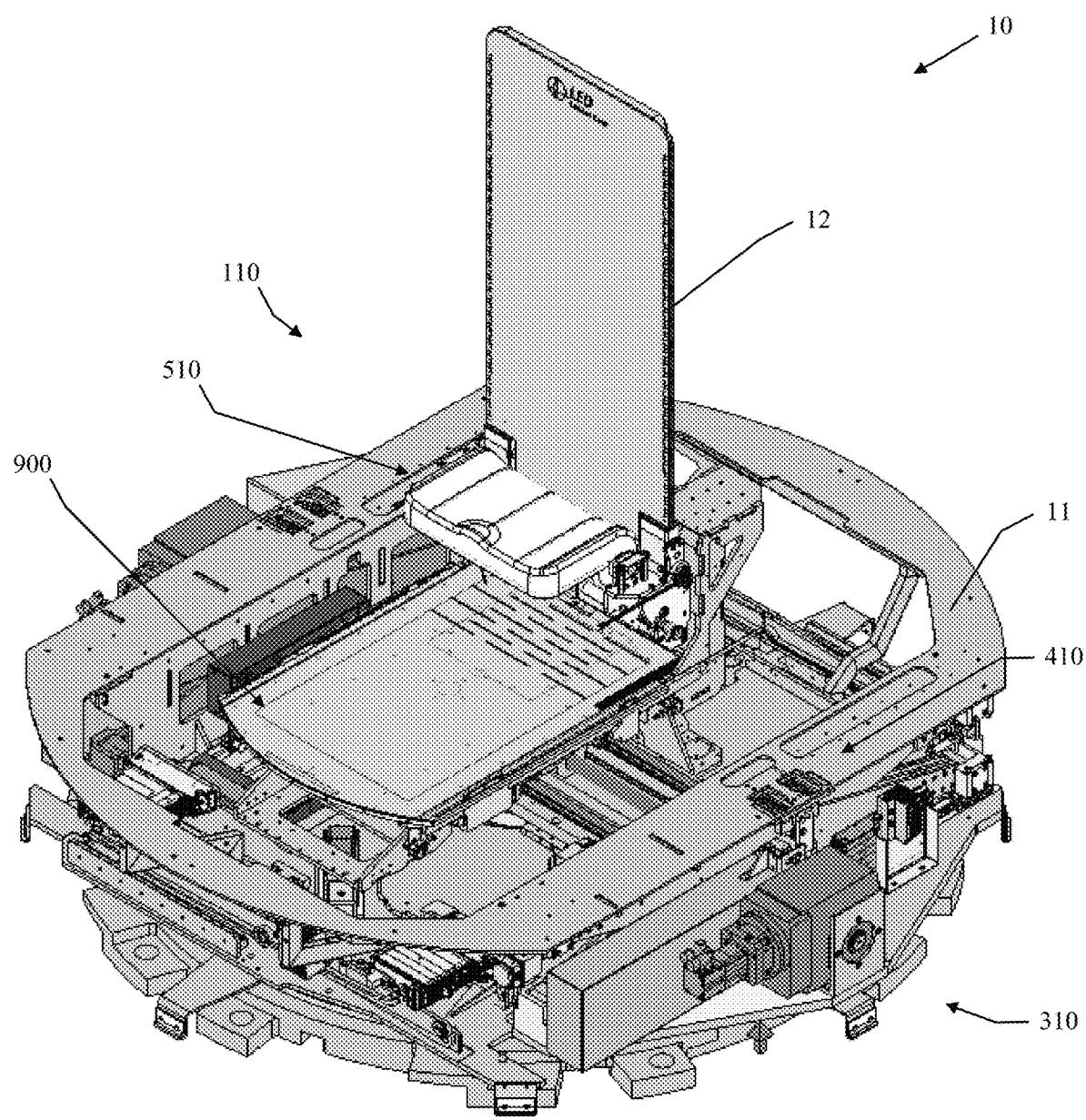
FIG. 2 is a perspective view of the patient positioning system of FIG. 1 with some components removed for clarity.
Figure 3:
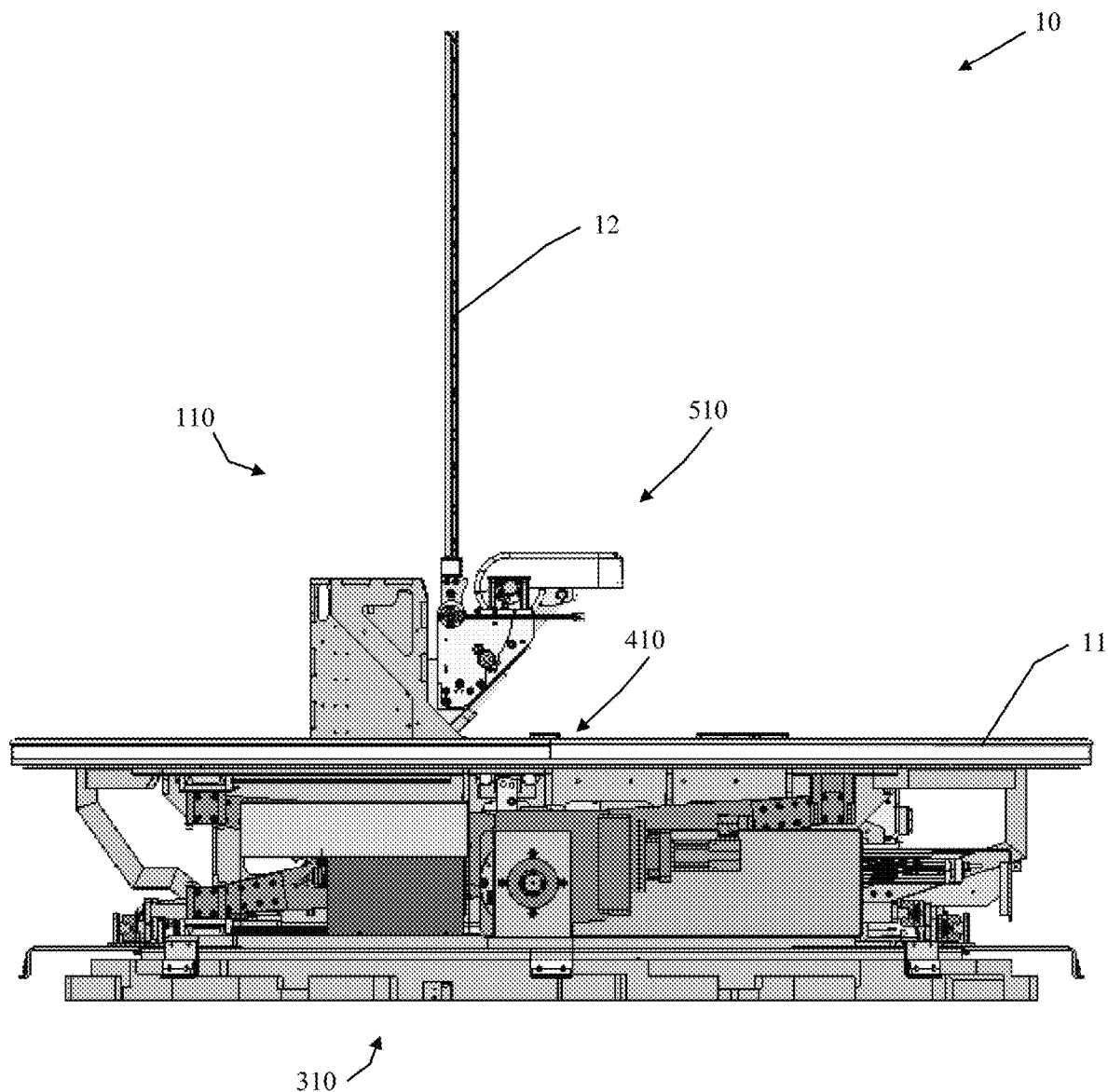
FIG. 3 is a side view of the patient positioning system of FIG. 1.
Figure 4:
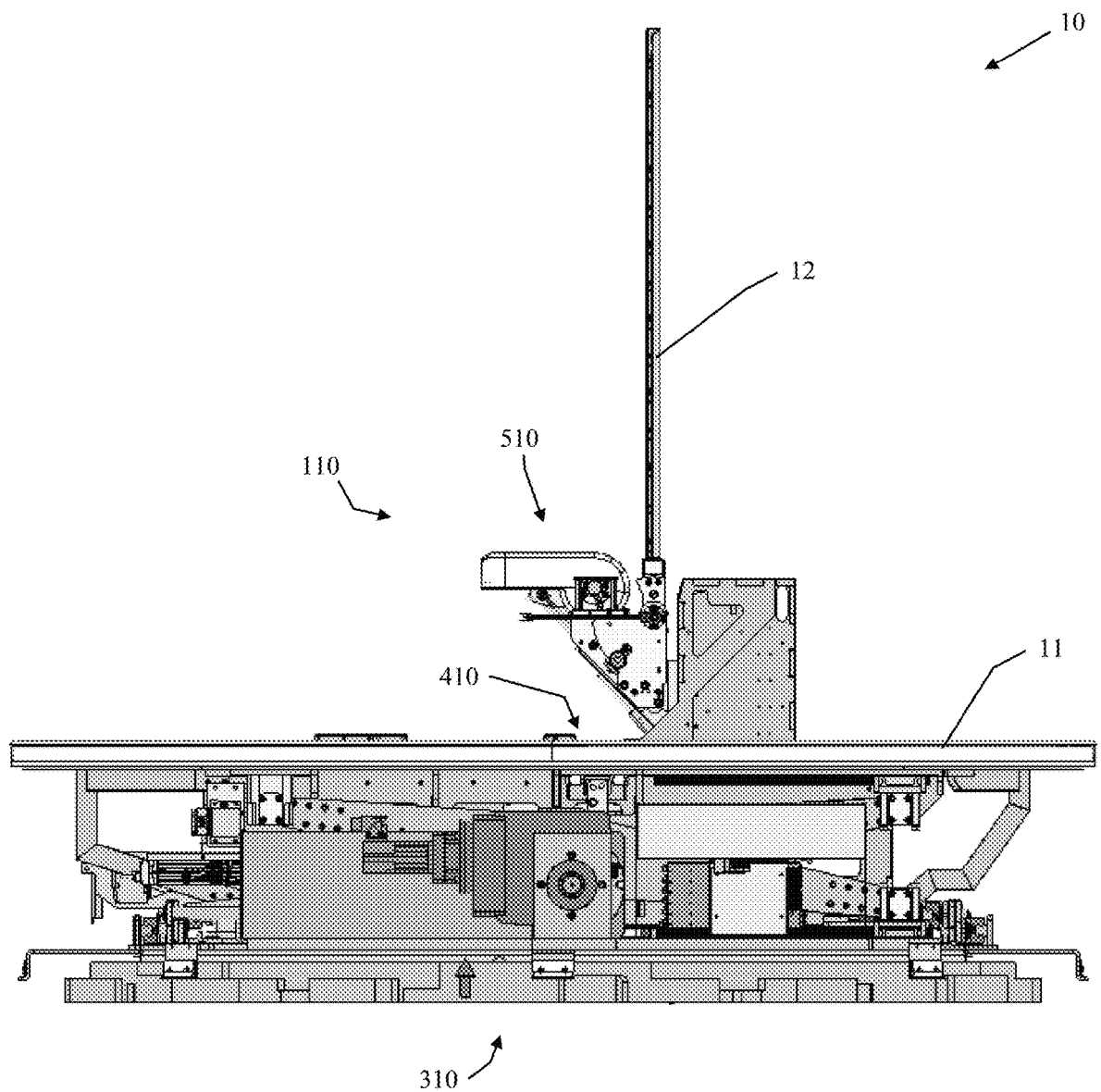
FIG. 4 is another side view of the patient positioning system of FIG. 1.

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DETAILED DESCRIPTION

Provided herein is technology relating to medical imaging and radiation therapy and particularly, but not exclusively, to devices, methods, and systems for positioning a patient with respect to a radiation source to image the patient and/or to treat the patient by exposing the patient to a radiation beam produced by the radiation source.

In this detailed description of the various embodiments, for purposes of explanation, numerous specific details are set forth to provide a thorough understanding of the embodiments disclosed. One skilled in the art will appreciate, however, that these various embodiments is practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

All literature and similar materials cited in this application, including but not limited to, patents, patent applications, articles, books, treatises, and internet web pages are expressly incorporated by reference in their entirety for any purpose. Unless defined otherwise, all technical and scientific terms used herein have the same meaning as is commonly understood by one of ordinary skill in the art to which the various embodiments described herein belongs. When definitions of terms in incorporated references appear to differ from the definitions provided in the present teachings, the definition provided in the present teachings shall control. The section headings used herein are for organizational purposes only and are not to be construed as limiting the described subject matter in any way.

Definitions

To facilitate an understanding of the present technology, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention is readily combined, without departing from the scope or spirit of the invention.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

As used herein, the terms "about", "approximately", "substantially", and "significantly" are understood by persons of ordinary skill in the art and will vary to some extent on the context in which they are used. If there are uses of these terms that are not clear to persons of ordinary skill in the art given the context in which they are used, "about" and "approximately" mean plus or minus less than or equal to 10% of the particular term and "substantially" and "significantly" mean plus or minus greater than 10% of the particular term.

As used herein, disclosure of ranges includes disclosure of all values and further divided ranges within the entire range, including endpoints and sub-ranges given for the ranges. As used herein, the disclosure of numeric ranges includes the endpoints and each intervening number therebetween with the same degree of precision. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

As used herein, the suffix "-free" refers to an embodiment of the technology that omits the feature of the base root of the word to which "-free" is appended. That is, the term "X-free" as used herein means "without X", where X is a feature of the technology omitted in the "X-free" technology. For example, a "calcium-free" composition does not comprise calcium, a "mixing-free" method does not comprise a mixing step, etc.

Although the terms "first", "second", "third", etc. is used herein to describe various steps, elements, compositions, components, regions, layers, and/or sections, these steps, elements, compositions, components, regions, layers, and/or sections should not be limited by these terms, unless otherwise indicated. These terms are used to distinguish one step, element, composition, component, region, layer, and/or section from another step, element, composition, component, region, layer, and/or section. Terms such as "first", "second", and other numerical terms when used herein do not imply a sequence or order unless clearly indicated by the context. Thus, a first step, element, composition, component, region, layer, or section discussed herein could be termed a second step, element, composition, component, region, layer, or section without departing from technology.

As used herein, the word "presence" or "absence" (or, alternatively, "present" or "absent") is used in a relative sense to describe the amount or level of a particular entity (e.g., component, action, element). For example, when an entity is said to be "present", it means the level or amount of this entity is above a pre-determined threshold; conversely, when an entity is said to be "absent", it means the level or amount of this entity is below a pre-determined threshold. The pre-determined threshold is the threshold for detectability associated with the particular test used to detect the entity or any other threshold. When an entity is "detected" it is "present"; when an entity is "not detected" it is "absent".

As used herein, an "increase" or a "decrease" refers to a detectable (e.g., measured) positive or negative change, respectively, in the value of a variable relative to a previously measured value of the variable, relative to a pre-established value, and/or relative to a value of a standard control. An increase is a positive change preferably at least 10%, more preferably 50%, still more preferably 2-fold, even more preferably at least 5-fold, and most preferably at least 10-fold relative to the previously measured value of the variable, the pre-established value, and/or the value of a standard control. Similarly, a decrease is a negative change preferably at least 10%, more preferably 50%, still more preferably at least 80%, and most preferably at least 90% of the previously measured value of the variable, the pre-established value, and/or the value of a standard control. Other terms indicating quantitative changes or differences, such as "more" or "less," are used herein in the same fashion as described above.

As used herein, a "system" refers to a plurality of real and/or abstract components operating together for a common purpose. In some embodiments, a "system" is an integrated assemblage of hardware and/or software components. In some embodiments, each component of the system interacts with one or more other components and/or is related to one or more other components. In some embodiments, a system refers to a combination of components and software for controlling and directing methods. For example, a "system" or "subsystem" may comprise one or more of, or any combination of, the following: mechanical devices, hardware, components of hardware, circuits, circuitry, logic design, logical components, software, software modules, components of software or software modules, software procedures, software instructions, software routines, software objects, software functions, software classes, software programs, files containing software, etc., to perform a function of the system or subsystem. Thus, the methods and apparatus of the embodiments, or certain aspects or portions thereof, may take the form of program code (e.g., instructions) embodied in tangible media, such as floppy diskettes, CD-ROMs, hard drives, flash memory, or any other machine-readable storage medium wherein, when the program code is loaded into and executed by a machine, such as a computer, the machine becomes an apparatus for practicing the embodiments. In the case of program code execution on programmable computers, the computing device generally includes a processor, a storage medium readable by the processor (e.g., volatile and non-volatile memory and/or storage elements), at least one input device, and at least one output device. One or more programs may implement or utilize the processes described in connection with the embodiments, e.g., through the use of an application programming interface (API), reusable controls, or the like. Such programs are preferably implemented in a high-level procedural or object-oriented programming language to communicate with a computer system. However, the program(s) can be implemented in assembly or machine language, if desired. In any case, the language is a compiled or interpreted language, and combined with hardware implementations.

As used herein, the term "computed tomography" is abbreviated "CT" and refers both to tomographic and non-tomographic radiography. For instance, the term "CT" refers to numerous forms of CT, including but not limited to X-ray CT, positron emission tomography (PET), single-photon emission computed tomography (SPECT), and photon counting computed tomography. Generally, computed tomography (CT) comprises use of an X-ray source and a detector that rotates around a patient and subsequent reconstruction of images into different planes. In embodiments of CT (e.g., devices, apparatuses, and methods provided for CT) described herein, the X-ray source is a static source and the patient is rotated with respect to the static source. Currents for X-rays used in CT describe the current flow from a cathode to an anode and are typically measured in milliamperes (mA).

As used herein, the term "structured to [verb]" means that the identified element or assembly has a structure that is shaped, sized, disposed, coupled, and/or configured to perform the identified verb. For example, a member that is "structured to move" is movably coupled to another element and includes elements that cause the member to move or the member is otherwise configured to move in response to other elements or assemblies. As such, as used herein, "structured to [verb]" recites structure and not function. Further, as used herein, "structured to [verb]" means that the identified element or assembly is intended to, and is designed to, perform the identified verb.

As used herein, the term "associated" means that the elements are part of the same assembly and/or operate together or act upon/with each other in some manner. For example, an automobile has four tires and four hub caps. While all the elements are coupled as part of the automobile, it is understood that each hubcap is "associated" with a specific tire.

As used herein, the term "coupled" refers to two or more components that are secured, by any suitable means, together. Accordingly, in some embodiments, the statement that two or more parts or components are "coupled" shall mean that the parts are joined or operate together either directly or indirectly, e.g., through one or more intermediate parts or components. As used herein, "directly coupled" means that two elements are directly in contact with each other. As used herein, "fixedly coupled" or "fixed" means that two components are coupled so as to move as one while maintaining a constant orientation relative to each other. Accordingly, when two elements are coupled, all portions of those elements are coupled. A description, however, of a specific portion of a first element being coupled to a second element, e.g., an axle first end being coupled to a first wheel, means that the specific portion of the first element is disposed closer to the second element than the other portions thereof. Further, an object resting on another object held in place only by gravity is not "coupled" to the lower object unless the upper object is otherwise maintained substantially in place. That is, for example, a book on a table is not coupled thereto, but a book glued to a table is coupled thereto.

As used herein, the term "removably coupled" or "temporarily coupled" means that one component is coupled with another component in an essentially temporary manner. That is, the two components are coupled in such a way that the joining or separation of the components is easy and does not damage the components. Accordingly, "removably coupled" components is readily uncoupled and recoupled without damage to the components.

As used herein, the term "operatively coupled" means that a number of elements or assemblies, each of which is movable between a first position and a second position, or a first configuration and a second configuration, are coupled so that as the first element moves from one position/configuration to the other, the second element moves between positions/configurations as well. It is noted that a first element is "operatively coupled" to another without the opposite being true.

As used herein, the term "rotatably coupled" refers to two or more components that are coupled in a manner such that at least one of the components is rotatable with respect to the other.

As used herein, the term "translatably coupled" refers to two or more components that are coupled in a manner such that at least one of the components is translatable with respect to the other.

As used herein, the term "temporarily disposed" means that a first element or assembly is resting on a second element or assembly in a manner that allows the first element/assembly to be moved without having to decouple or otherwise manipulate the first element. For example, a book simply resting on a table, e.g., the book is not glued or fastened to the table, is "temporarily disposed" on the table.

As used herein, the term "correspond" indicates that two structural components are sized and shaped to be similar to each other and is coupled with a minimum amount of friction. Thus, an opening which "corresponds" to a member is sized slightly larger than the member so that the member may pass through the opening with a minimum amount of friction. This definition is modified if the two components are to fit "snugly" together. In that situation, the difference between the size of the components is even smaller whereby the amount of friction increases. If the element defining the opening and/or the component inserted into the opening are made from a deformable or compressible material, the opening may even be slightly smaller than the component being inserted into the opening. With regard to surfaces, shapes, and lines, two, or more, "corresponding" surfaces, shapes, or lines have generally the same size, shape, and contours.

As used herein, a "path of travel" or "path," when used in association with an element that moves, includes the space an element moves through when in motion. As such, any element that moves inherently has a "path of travel" or "path."

As used herein, the statement that two or more parts or components "engage" one another shall mean that the elements exert a force or bias against one another either directly or through one or more intermediate elements or components. Further, as used herein with regard to moving parts, a moving part may "engage" another element during the motion from one position to another and/or may "engage" another element once in the described position. Thus, it is understood that the statements, "when element A moves to element A first position, element A engages element B," and "when element A is in element A first position, element A engages element B" are equivalent statements and mean that element A either engages element B while moving to element A first position and/or element A either engages element B while in element A first position.

As used herein, the term "operatively engage" means "engage and move." That is, "operatively engage" when used in relation to a first component that is structured to move a movable or rotatable second component means that the first component applies a force sufficient to cause the second component to move. For example, a screwdriver is placed into contact with a screw. When no force is applied to the screwdriver, the screwdriver is merely "coupled" to the screw. If an axial force is applied to the screwdriver, the screwdriver is pressed against the screw and "engages" the screw. However, when a rotational force is applied to the screwdriver, the screwdriver "operatively engages" the screw and causes the screw to rotate. Further, with electronic components, "operatively engage" means that one component controls another component by a control signal or current.

As used herein, the term "number" shall mean one or an integer greater than one (e.g., a plurality).

As used herein, in the phrase "[x] moves between its first position and second position," or, "[y] is structured to move [x] between its first position and second position," "[x]" is the name of an element or assembly. Further, when [x] is an element or assembly that moves between a number of positions, the pronoun "its" means "[x]," i.e., the named element or assembly that precedes the pronoun "its."

As used herein, a "radial side/surface" for a circular or cylindrical body is a side/surface that extends about, or encircles, the center thereof or a height line passing through the center thereof. As used herein, an "axial side/surface" for a circular or cylindrical body is a side that extends in a plane extending generally perpendicular to a height line passing through the center. That is, generally, for a cylindrical soup can, the "radial side/surface" is the generally circular sidewall and the "axial side(s)/surface(s)" are the top and bottom of the soup can.

As used herein, a "diagnostic" test includes the detection or identification of a disease state or condition of a subject, determining the likelihood that a subject will contract a given disease or condition, determining the likelihood that a subject with a disease or condition will respond to therapy, determining the prognosis of a subject with a disease or condition (or its likely progression or regression), and determining the effect of a treatment on a subject with a disease or condition. For example, a diagnostic can be used for detecting the presence or likelihood of a subject having a cancer or the likelihood that such a subject will respond favorably to a compound (e.g., a pharmaceutical, e.g., a drug) or other treatment.

As used herein, the term "condition" refers generally to a disease, malady, injury, event, or change in health status.

As used herein, the term "treating" or "treatment" with respect to a condition refers to preventing the condition, slowing the onset or rate of development of the condition, reducing the risk of developing the condition, preventing or delaying the development of symptoms associated with the condition, reducing or ending symptoms associated with the condition, generating a complete or partial regression of the condition, or some combination thereof. In some embodiments, "treatment" comprises exposing a patient or a portion thereof (e.g., a tissue, organ, body part, or other localize region of a patient body) to radiation (e.g., electromagnetic radiation, ionizing radiation).

As used herein, the term "beam" refers to a stream of radiation (e.g., electromagnetic wave and/or or particle radiation). In some embodiments, the beam is produced by a source and is restricted to a small-solid angle. In some embodiments, the beam is collimated. In some embodiments, the beam is generally unidirectional. In some embodiments, the beam is divergent.

As used herein, the term "patient" or "subject" refers to a mammalian animal that is identified and/or selected for imaging and/or treatment with radiation. Accordingly, in some embodiments, a patient or subject is contacted with a beam of radiation, e.g., a primary beam produced by a radiation source. In some embodiments, the patient or subject is a human. In some embodiments, the patient or subject is a veterinary or farm animal, a domestic animal or pet, or animal used for clinical research. In some embodiments, the subject or patient has cancer and/or the subject or patient has either been recognized as having or at risk of having cancer.

As used herein, the term "treatment volume" or "imaging volume" refers to the volume (e.g., tissue) of a patient that is selected for imaging and/or treatment with radiation. For example, in some embodiments, the "treatment volume" or "imaging volume" comprises a tumor in a cancer patient. As used herein, the term "healthy tissue" refers to the volume (e.g., tissue) of a patient that is not and/or does not comprise the treatment volume. In some embodiments, the imaging volume is larger than the treatment volume and comprises the treatment volume.

As used herein, the term "radiation source" or "source" refers to an apparatus that produces radiation (e.g., ionizing radiation) in the form of photons (e.g., described as particles or waves). In some embodiments, a radiation source is a linear accelerator ("linac") that produces x-rays or electrons to treat a cancer patient by contacting a tumor with the x-ray or electron beam. In some embodiments, the source produces particles (e.g., photons, electrons, neutrons, hadrons, ions (e.g., protons, carbon ions, other heavy ions)). In some embodiments, the source produces electromagnetic waves (e.g., x-rays and gamma rays having a wavelength in the range of approximately 1 pm to approximately 1 nm). While it is understood that radiation can be described as having both wave-like and particle-like aspects, it is sometimes convenient to refer to radiation in terms of waves and sometimes convenient to refer to radiation in terms of particles. Accordingly, both descriptions are used throughout without limiting the technology and with an understanding that the laws of quantum mechanics provide that every particle or quantum entity is described as either a particle or a wave.

As used herein, the term "static source" refers to a source that does not revolve around a patient during use of the source for imaging or therapy. In particular, a "static source" remains fixed with respect to an axis passing through the patient while the patient is being imaged or treated. While the patient may rotate around said axis to produce relative motion between the static source and rotating patient that is equivalent to the relative motion of a source revolving around a static patient, a static source does not move with reference to a third object, frame of reference (e.g., a treatment room in which a patient is positioned), or patient axis of rotation during imaging or treatment, while the patient is rotated with respect to said third object, said frame of reference (e.g., said treatment room in which said patient is positioned), or patient axis of rotation through the patient during imaging or treatment. Thus, a static source is installed on a mobile platform and thus the static source may move with respect to the Earth and fixtures on the Earth as the mobile platform moves to transport the static source. Thus, the term "static source" may refer to a mobile "static source" provided that the mobile "static source" does not revolve around an axis of rotation through the patient during imaging or treatment of the patient. Further, the static source may translate and/or revolve around the patient to position the static source prior to imaging or treatment of the patient or after imaging or treatment of the patient. Thus, the term "static source" may refer to a source that translates or revolves around the patient in non-imaging and non-treatment use, e.g., to position the source relative to the patient when the patient is not being imaged and/or treated. In some embodiments, the "static source" is a photon source and thus is referred to as a "static photon source".

Embodiments of the technology described herein relate to translations along axes and/or rotations around axes. In some embodiments, a coordinate system is used that comprises an X axis, a Y axis, and a Z axis defined with respect to a patient support and/or a patient. See FIG. 1. As shown in FIG. 1, embodiments use a coordinate system in which the X axis and Y axis together are in and/or define a horizontal plane and the Z axis is and/or defines a vertical axis. With respect to a patient positioned on the patient support (e.g., the patient positioning apparatus), the X axis is a left-right, horizontal, or frontal axis; the Y axis is an anteroposterior, dorsoventral, or sagittal axis; and the Z axis is a sagittal or longitudinal axis. The X axis and the Y axis together are in and/or define a horizontal, transverse, and/or axial plane. The Y axis and the Z axis together are in and/or define a sagittal or longitudinal plane. The X axis and the Z axis together are in and/or define a frontal or coronal plane.

Accordingly, in some embodiments, descriptions of movements as "forward" or "backward" are movements along the Y axis; descriptions of movements as "left" or "right" are movements along the X axis; and descriptions of movements as "up" and "down" are movements along the Z axis. Furthermore, a rotation described as "roll" is rotation around the Y axis; a rotation described as "pitch" is rotation around the X axis; and a rotation described as "yaw" is rotation around the Z axis. Thus, in some embodiments, technologies are described as having six degrees of freedom, e.g., translations along one or more of the X, Y, and/or Z axes and rotations around one or more of the X, Y, and/or Z axes.

Description

Although the disclosure herein refers to certain illustrated embodiments, it is to be understood that these embodiments are presented by way of example and not by way of limitation.

Patient Positioning System

The technology described herein relates to a system and related methods for positioning a patient with respect to a radiation source (e.g., a therapeutic treatment beam or a medical imaging beam). In some embodiments, the technology relates to a patient positioning system 10 for positioning a patient in a generally upright position with a torso aligned in a vertical direction (e.g., standing, kneeling, sitting, etc.). In some embodiments, the radiation source is a static source. In some embodiments, the radiation source is movably mounted and is moved to change the orientation of the radiation source.

In some embodiments, the patient positioning system 10 comprises a translatable member that is vertically translatable such that the translatable member articulates towards and away from a surface on which the patient positioning system is supported. The translatable member is in the form of a carriage that is oriented in a vertical direction and comprises a main body portion. In some embodiments, the translatable member is mounted to a supporting structure that is in turn mounted to the surface. In some embodiments, the supporting structure provides stability to the patient positioning system and houses a drive mechanism to affect the vertical movement of the translatable member.

In some embodiments, the patient positioning system 10 comprises a configurable patient support 110 (e.g., patient support, patient support assembly, etc.). In some embodiments, the patient support 110 comprises a generally elongate structure. The patient support 110 is configured to receive and secure a patient in a generally upright position. The patient support 110 is rotatably mounted to the translatable member such that the patient support is rotatable about a vertical axis (e.g., an essentially vertical and/or substantially vertical axis) relative to the translatable member. A lower end of the patient support is mounted to a rotating disc. In some embodiments, an upper end of the patient support is mounted to another rotating disc. By this arrangement, the patient support is rotatably mounted to the translatable member such that the patient support is rotatable about a vertical axis. Also, as the translatable member is able to articulate vertically, the patient support mounted to the translatable member may similarly articulate vertically.

The patient support 110 is adapted to receive a patient requiring exposure to a treatment beam and/or to an imaging beam. The patient support is offset from the vertical axis of rotation such that the torso of a patient secured to the patient support is aligned with the vertical axis of rotation (e.g., a vertical axis of the patient is aligned with the vertical axis of rotation). Accordingly, in some embodiments, the position of a patient supported by the patient support may be adjusted by the rotational coupling of the patient support to the translatable member and/or by the vertical translation of the translatable member. By this arrangement, the position of a patient may be adjusted with respect to a treatment beam or an imaging beam so that the treatment beam or imaging beam may target the area of the patient requiring treatment or imaging.

In some embodiments, a patient is in a sitting position with the patient torso in a vertical upright position centered about the vertical axis of rotation. In some embodiments, a fixed treatment beam source is supported by the same surface as the supporting structure and is thus fixed in position to provide a static source. The treatment beam source is configured to direct a fixed treatment beam towards a patient positioned on the patient support. In some embodiments, the treatment beam source is a linac and the beam is shaped by a multi-leaf collimator. The source is positioned to direct a beam along a horizontal direction (e.g., an essentially horizontal and/or substantially horizontal direction). A detection panel is mounted to the supporting structure such that the detection panel is locatable in the path of the treatment beam. In some embodiments, the detection panel is adjustably mounted to an adjustable mounting so that the position of the detection panel may be altered to facilitate patient access to the patient support for ingress to the patient positioning system and egress from the patient positioning system. The adjustable mounting is a pivotable mounting so that the detection panel is swung away from its position in alignment with the treatment beam. In some embodiments, an additional detection panel is mounted to the housing of the treatment beam source for use in conjunction with an imaging beam source (e.g., mounted to the supporting structure). In some embodiments, the additional detection panel is adjustably mounted so that it can be moved to facilitate patient access to the patient support. In some embodiments, the imaging beam source is positioned in a horizontally orthogonal orientation to the treatment beam source such that the beam paths intersect at the region of a patient located on the patient support, though other orientations of the imaging beam source and/or treatment beam source are included in embodiments of the technology. Both the treatment beam and the imaging beam are oriented to intersect with the vertical axis of rotation.

In some embodiments, the translatable member is in a vertically downwards position termed the first position. In some embodiments, the first position positions the translatable member and the patient support mounted thereto near to the surface supporting the patient positioning system. Accordingly, the first position may allow for patient ingress to the patient positioning system such that the patient can be secured to the patient support. In some embodiments, when the translatable member is in the first position it is partially recessed into the surface so that the rotating disc is substantially level with the surface, thus facilitating patient access to the patient support without the patient having to negotiate uneven surfaces. In some embodiments, the first position is configured so that the fixed treatment beam is directed towards the head of a patient (e.g., a patient having a height of approximately 1900 mm) when that patient is secured to the patient support in a seated position. This height corresponds to that of an American male patient of the 95th height percentile, making the patient positioning system adaptable for used with a large portion of the population, though embodiments of the technology include other arrangements and are appropriate for patients at the upper and lower limits of height and/or weight.

In exemplary embodiments, securing a patient to the patient support in a seated position allows for the fixed treatment beam to target a patient in an area from the top of a patient head to the general region of the patient abdomen (e.g., near the hips and/or navel). For example, the treatment beam is configured to align with the head of a seated patient (e.g., the head of a seated patient having a height of approximately 1900 mm). If a patient is shorter than about 1900 mm, the treatment beam would be directed over the head of the seated patient in the first position. Thus, embodiments provide aligning a head of a patient less than about 1900 mm in height with the treatment beam by translating the translatable member vertically upwards away from the surface supporting the patient positioning system. Similarly, the patient is positioned vertically upwards by the translation of the translatable member to align the fixed treatment beam with any part of the torso up to the general region of the patient navel. Embodiments further provide targeting a part of the patient lower than the navel (e.g., buttocks, legs, and/or feet) with the fixed treatment beam by providing the patient in a standing position by configuring the patient support to support the patient in a standing position.

For example, in some embodiments, a standing patient is supported by the patient support when the translatable member is in the first position. The vertical height of the patient support is configured to accommodate a patient with a height of about 1900 mm. Further, in some embodiments, a standing patient is supported by the patient support when the translatable member is in a vertically upwards position termed the second position. When the translatable member is in the second position, the fixed treatment beam may, in some embodiments, be directed towards the feet and/or ankles of the patient, thus providing treatment of the feet and/or ankles. In some embodiments, the translatable member is moved to an appropriate vertical position between the first position and the second position to align the fixed treatment beam with a section of the patient between the patient feet and navel. Accordingly, the technology provides for the fixed treatment beam to target any part of a patient, e.g., from the top of the head to the feet, while minimizing the vertical travel of the translatable member. Accordingly, the patient positioning system provides a patient support appropriate for standing and sitting patients of all heights, e.g., a range of heights from a patient in the 95th height percentile of an American male to a patient in the 5th height percentile of a Japanese female. In some embodiments, the translatable member vertically translates approximately 3000 to 4000 mm (e.g., 3000, 3050, 3100, 3150, 3200, 3250, 3300, 3350, 3400, 3450, 3500, 3550, 3600, 3650, 3700, 3750, 3800, 3850, 3900, 3950, or 4000 mm) to target any portion from head to foot of a 95th height percentile American male patient. One advantage of minimizing the vertical travel of the translatable member is that the vertical space required by the patient positioning system is minimized, thus allowing the patient positioning system to be located in a space smaller than conventional treatment bunkers and reducing the costs of installation and assembly.

When the part of a patient requiring treatment may be targeted in either of the standing or seated positions, the position in which the patient is supported by the patient support is selectable (e.g., based on patient comfort, patient condition, and/or treatment protocol). In addition, in some embodiments, translation of the translatable member provides for the treatment of a patient in a sitting or standing position from the top of the patient head to the patient feet. In addition, in some embodiments, translation of the translatable member provides for the treatment of a patient in a sitting or standing position from the top of the patient head to the patient abdomen and genital area.

In some embodiments, the translatable member is adapted to move between a vertically upwards second position and a vertically downwards first position wherein the translatable member is located in a recessed potion of the surface supporting the patient positioning system, such that part of the patient positioned on the translatable member is similarly located in the recess. In some embodiments, the patient positioning system is arranged so that the fixed treatment beam is directed towards the head of an American male of the 95th height percentile when that patient is secured to the patient support in a first position and locating part of the patient in the recess. In some embodiments, the patient positioning system is arranged so that the fixed treatment beam is directed towards the feet and/or ankles of a patient secured to the patient support in the second position. In some exemplary embodiments, this arrangement reduces the vertical height of the patient support by configuring a portion of the vertical travel of the translatable member between the first and second positions into the surface supporting the patient support.

Thus, in some embodiments, translation of the translatable member provides for the treatment of a patient in a sitting or standing position at a region of the patient body that is anywhere from the top of the patient head to the patient feet. Further, in some embodiments, translation of the translatable member provides for the treatment of a patient in a sitting or standing position at a region of the patient body that is anywhere from the top of the patient head to the patient abdomen and genital area. Accordingly, embodiments of the technology provide for treatment of, e.g., a patient head, neck, chest, breast, upper arm, elbow, lower arm, hands, abdomen, internal organs, genitals, anus, upper leg, knee, lower leg, ankle, and feet. This list is exemplary and not limiting; thus, other body parts and areas between the patient head and feet and/or between the patient head and genitals are all possible areas that may be treated by the technology.

In some embodiments, the technology provides an imaging system (e.g., a CT scanner) that comprises a horizontal ring located vertically above the patient positioning system. See, e.g., U.S. Pat. App. Pub. No. 20220183641, incorporated herein by reference. By locating the patient positioning system vertically adjacent with the imaging system, the patient positioning system orients the patient with respect to both the fixed treatment beam and the imaging system. Embodiments comprising this arrangement provide the patient in a position to be imaged by the imaging system in an upright position, thus providing medical professionals with images of the patient anatomy in the same upright position in which they will also be subjected to the fixed treatment beam. Accordingly, the technology reduces uncertainties that may arise from the gravitational shifting of patient anatomy when imaging is performed in a different patient position with respect to treatment.

In some embodiments, e.g., as described above, the radiation source (e.g., a treatment beam) is fixed in position such that the relative movement between the patient and the treatment beam is affected by the movement of the patient positioning system. In an alternative embodiment, the position of the treatment beam is adjustable such that the relative movement between the patient and the treatment beam is effected by the movement of the patient positioning system and by adjusting the position of the treatment beam. For example, in some embodiments, the position of the treatment beam is adjustable between two vertically displaced positions such that the vertical travel required by the patient support is reduced and instead accounted for by the vertical adjustment of the treatment beam. Furthermore, the technology provides an advantage of decreasing and/or minimizing the amount of shielding required because the degree of adjustment of the treatment beam is relatively small.

In some embodiments, the technology described herein comprises a radiation source that is a treatment beam source, e.g., a linac that produced a beam shaped by a multi-leaf collimator. However, the technology is not limited to embodiments comprising a treatment beam source, e.g., a linac that produced a beam shaped by a multi-leaf collimator and includes embodiments comprising a patient positioning system used with other forms of radiation sources, e.g., with imaging technologies such as CT or MRI.

In some embodiments, the patient support 110 comprises a patient immobilization system. In some embodiments, the patient immobilization system is mounted to the patient support to immobilize the patient securely and comfortably to the patient support. In some embodiments, the patient immobilization system is configurable into a first orientation to secure the patient to the patient support in a seated position and is configurable into a second orientation to secure the patient to the patient support in a standing, or in a substantially standing, position.

As described herein, embodiments provide a patient positioning system comprising a patient support assembly. In some embodiments, the patient support assembly comprises a back rest, a seat member, a shin rest, an arm rest, a head rest, and/or foot braces. In some embodiments, the foot braces comprise a heel stop. Embodiments provide that the back rest, seat member, shin rest, arm rest, a head rest, and/or foot braces (e.g., heel stop) is/are configurable among a number of positions to accommodate patient ingress and/or egress from the patient support system (e.g., from the patient support assembly) and/or to support a patient in a number of positions for imaging or treatment.

For example, in some embodiments, the patient support assembly 110 is configurable to receive and support a patient with a torso tilted at an angle to the vertical axis. By this arrangement, the effect of gravity acting on the tilted orientation of the patient relative to a vertical axis may aid in stabilizing the patient received by the patient support assembly. Embodiments provide that the patient torso is tilted anteriorly or is tilted posteriorly. See, e.g., U.S. Pat. App. Pub. No. 20200268327, which is incorporated herein by reference.

In some exemplary embodiments, the patient support 110 provides a patient with the torso angled with respect to a vertical axis in an anterior direction to facilitate targeting of a patient breasts by a radiation source. In some embodiments, the angle by which the patient torso is configured to tilt is between about ±0° to about 20°, between about ±5° to about 15°, or about ±10°. The configurable patient support 110 is configured to receive a patient with a torso tilted at an angle in both a first orientation, or a first configuration, wherein the patient is in a generally seated position, and a second orientation, or a second configuration, wherein the patient is in a generally standing, or substantially standing, position. In some embodiments, the patient support assembly provides a patient in a "perched position". As used herein, the term "perched position" refers to a patient in a generally standing position with a torso angled posteriorly with respect to a vertical axis, optionally also having bent knees.

In some embodiments, the patient support 110 is configured in a first orientation to receive a patient in a generally seated position. In some embodiments, the patient support assembly is configurable to support a wide range of the patient population in a seated position, e.g., patients having a range of heights from a height equivalent to the 95th percentile of an American male to a height equivalent to the 5th percentile of a Japanese female.

In some embodiments, the patient support 110 comprises a back rest 12. In some embodiments, the back rest 12 is aligned or substantially or effectively aligned with the vertical axis. In some embodiments, the back rest 12 is angled with respect to a vertical axis such that a patient resting against the back rest is similarly angled with respect to a vertical axis (e.g., the patient torso is angled with respect to the vertical axis). Additionally, in some embodiments, the patient support 110 in the first orientation comprises a seat member 511 extending orthogonally from a plane generally aligned with the back rest 12 for accommodating the buttocks, or posterior, of a patient in a seated position. In some embodiments, the patient support 110 in the first orientation comprises a shin rest positioned toward the back rest so as to be located posterior to the patient ankles and thereby not contacting any part of the patient in the seated position. In some embodiments, the shin rest 13 is located below the seat member 12 when the patient support 110 is in the first orientation. In some embodiments, the patent support 110 comprises arm rests that are adjustable in location along the axis of the back rest. Adjusting the vertical position of the arm rests along the axis of the back rest may allow patients with varying anthropometric variation to rest the arms in a number of positions to facilitate specific target areas being targeted by a radiation source.

In some embodiments, the patient support 110 in a second orientation is configured to receive a patient in a generally standing position. In some embodiments, the second orientation comprises the back rest 12 angled posteriorly and displaced vertically upwards to receive the back of a patient in a generally standing position and having bent knees (e.g., a patient in the perched position). Accordingly, in some embodiments, configuring the patient support 110 in the second orientation comprises displacing and/or removing the seat member from the assembly, e.g., by rotating the seat member downwards to a position aligned with the plane of the back rest or otherwise displacing the seat member from its position in the first orientation, to locate the seat member where it does not provide an obstacle to patient ingress into the patient support assembly in the second position and/or does not provide an obstacle to a patient received by the patient support in the second position. Further, in some embodiments, the patient support 110 in a second orientation comprises a foot brace (e.g., a heel stop) positioned to contact the heels of a patient and support the patient in a generally standing position. In some embodiments, the foot brace (e.g., heel stop) is adjustably mounted to the rotatable disc. In some embodiments, the foot brace (e.g., heel stop) is adjustable by translating the foot brace (e.g., heel stop).

In some embodiments, the seat member 511 is located posteriorly of the patient thighs to provide support for the patient upper legs when the patient is in a generally standing position with bent knees (e.g., a patient in the perched position). In some embodiments, the patient support 110 in the second orientation comprises a shin rest 13 anterior of the patient ankles, e.g., to contact the patient shins when the patient is in the generally standing position. In this arrangement, the patient is supported by the shin rest 13 and by the back rest 12. In some embodiments, the shin rest receives the patient shins with the ankles in a generally vertical alignment, though other arrangements are possible. In some embodiments, the shin rest is positioned such that a patient in a generally standing position (e.g., with a torso inclined approximately 10° with respect to a vertical axis) is positioned with hips bent at an angle of approximately 150° as measured between the torso and the thighs. Such a configuration maintains a patient in a stable and comfortable position, e.g., a position that allows a patient to remain still and comfortable in a generally standing position with bent hips and knees while having their weight supported by the back rest and the shin rest. In some embodiments, the hips are bent at an angle of between about 135° to about 165°, between about 145° to about 155°, or at another suitable angle, as measured between the torso and the thighs. In some embodiments, selection of the hip angle depends on factors including the size of the patient, the angle of posterior incline of the patient torso, and/or patient comfort and/or range of mobility. In some embodiments, the position of the adjustable arm rests is selected such that the patient upper arms are at an angle of about 25° relative to a horizontal plane orthogonal to the vertical axis of rotation. Such a position provides comfortable and stable support to a patient having the arms in a position above the chest, e.g., to allow the chest area to be targeted by a radiation source.

In some embodiments, the patient support 110 in the second orientation comprises a shin rest 13 anterior of the patient ankles, e.g., to contact the patient shins when the patient is in the generally standing position, and a foot brace 14 (e.g., a heel stop) posterior of the patient feet, e.g., to contact the patient heels when the patient is in the generally standing position. In this arrangement, the patient is supported by the shin rest 13, foot brace 14 (e.g., heel stop), and the back rest 12. In some embodiments, the shin rest receives the patient shins with the ankles in a generally vertical alignment, though other arrangements are possible. In some embodiments, the shin rest is positioned such that a patient in a generally standing position (e.g., with a torso inclined approximately 10° with respect to a vertical axis) is positioned with hips bent at an angle of approximately 150° as measured between the torso and the thighs. Such a configuration maintains a patient in a stable and comfortable position, e.g., a position that allows a patient to remain still and comfortable in a generally standing position with bent hips and knees while having their weight supported by the back rest, shin rest, and foot brace (e.g., heel stop). In some embodiments, the hips are bent at an angle of between about 135° to about 165°, between about 145° to about 155°, or at another suitable angle, as measured between the torso and the thighs. In some embodiments, selection of the hip angle depends on factors including the size of the patient, the angle of posterior incline of the patient torso, and/or patient comfort and/or range of mobility. In some embodiments, the position of the adjustable arm rests is selected such that the patient upper arms are at an angle of about 25° relative to a horizontal plane orthogonal to the vertical axis of rotation. Such a position provides comfortable and stable support to a patient having the arms in a position above the chest, e.g., to allow the chest area to be targeted by a radiation source.

In some embodiments, the configurable patient support 110 comprises a generally elongate upright structure with an integrated back rest comprising a padded material that is contoured to conform with the patient anatomy, for example, the curvature of a patient back. In some embodiments, the integrated back rest comprises a contoured component provided by a rigid or semi-rigid cushion specifically molded to complement the shape of the patient body, e.g., the patient back. In some embodiments, the contoured component is a cushion configured to mold to the patient body and retain the molded shape when gas inside the cushion is removed (e.g., by providing a vacuum drawn through a self-sealing quick-release valve of the cushion). After removing gas from the cushion, the cushion retains its shape (e.g., for 1 to 6 weeks or more). In some exemplary embodiments, the contoured component is provided by a VAC-LOK cushion commercially available from CIVCO Radiotherapy. Similar products are commercially available from other vendors.

In some embodiments, the technology provides a patient support assembly comprising an integrated patient support (and, optionally, a patient immobilization system). In some embodiments, the back rest is adapted to sustain a back of the patient at an angle relative to the vertical axis. A patient-receiving side of the back rest is angled posteriorly to the vertical axis and the patient-receiving side faces the vertical axis. The back rest is vertically adjustable to receive a patient back in either the first orientation or the second orientation. In some embodiments, the back rest is configured to slide along an axis slanted at an angle relative to the vertical axis. In some embodiments, the back rest is vertically adjustable by about 400 mm between the first orientation and the second orientation to accommodate patients with a height between that of a 95th percentile American male and a 5th percentile American female. Furthermore, the patient support assembly is mounted to a rotatable structure (e.g., a rotatable disc, a rotatable platform) to provide rotation of the patient support assembly (and, when the patient support assembly is supporting a patient, to provide rotation of a patient) about a vertical axis.

In some embodiments, the back rest 12 is attached to the patient support 110 by a locking interface as further described below.

In some embodiments, the vertical location of the back rest is adjustable independently of a vertical translation of the patient. For example, in some embodiments, vertical translation of the patient is effected by the translatable member or by a vertical translation of the patient support assembly relative to the translatable member (e.g., the patient support assembly is moveably mounted to the translatable member such that the patient support assembly is adapted to rotate and/or to move in a vertical direction, relative to the translatable member). Accordingly, the vertical location of the patient may be adjusted without affecting the patient position with respect to the patient support assembly.

Adjusting the vertical location of the back rest may affect the patient position and cause unwanted movement (e.g., changing an extent of the patient legs) and thus cause unwanted movement of the patient organs. Furthermore, when a treatment or imaging plan comprises contacting a patient with a beam impinging on the patient in a helical pattern, the patient is vertically translated and rotated during treatment or imaging while the patient position on the patient support assembly remains constant or unchanged. Therefore, embodiments provide for independently adjusting the patient position with respect to the patient support assembly and vertical location with respect to the patient support system and/or beam line. Accordingly, in some embodiments, a first actuator or a first set of actuators is provided to adjust the patient position with respect to the patient support assembly by adjusting a vertical location of the back rest. In some embodiments, such movement is effectuated while the radiation source is off (e.g., to adjust the patient position for a treatment or imaging or to improve the patient comfort). Furthermore, in some embodiments, a second actuator or a second set of actuators is provided to adjust the patient vertical location with respect to the patient support system and/or beam line, for example, to translate the patient while the radiation source is on or for moving the patient to align with the treatment or imaging plan, isocenter, or beam line.

In some embodiments, the first and second actuators, or first set and second set of actuators, operate (e.g., independently or simultaneously) to facilitate ingress or egress of patient from the patient positioning system, e.g., by moving components into static configurations that facilitate ingress and/or egress and/or by operatively engaging the patient to facilitate ingress and/or egress by applying a force to the patient, e.g., as further described herein. In some embodiments, other elements of the patient positioning system are adjustable independently of a vertical translation of the patient. For example, in some embodiments, a third actuator or a third set of actuators, is provided for adjusting a tilt, orientation, or vertical location of the seat member, e.g., as further described below. For example, the seat member may be used to assist in positioning a non-ambulatory patient from a wheelchair into the patient positioning system. As a further example, adjusting the seat member may aid in adjusting the vertical location of the patient.

In some embodiments, the shin rest is adjustably mounted to the rotatable disc and is thus configurable between a first position and a second position when the patient support assembly is in the first orientation and the second orientation, respectively. In some embodiments, the shin rest comprises a padded member in a generally vertical alignment for receiving the shins of a patient. In some embodiments, the shin rest is adjustable to vary the width between a shin support for a left leg and a shin support for a right leg. For example, in some embodiments, the shin rest has an adjustable width to accommodate and comfortably and stably support a range of patients having a range of widths between the lower legs and/or shins. In some embodiments, the patient support comprises interchangeable shin rests of different sizes to accommodate and comfortably and stably support patients having a range of widths between the lower legs and/or shins. In some embodiments, a hand rail (e.g., a stabilization bar) is attached to the patient support (e.g., to the shin rest) to provide support for a patient, e.g., to support the ingress of the patient into the patient support, to assist positioning the patient on the patient support, and/or to support the egress of the patient from the patient support.

In some embodiments, the shin rest is adjustably mounted to the rotating disc, e.g., to provide an adjustable position relative to the back rest. In some embodiments, in the first orientation, the shin rest is located underneath the seat member so as not to contact with a seated patient supported by the patient support assembly. In some embodiments, in the second orientation, the shin rest is located forward of the back rest to support the patient shins when the patient back locates against the back rest. Alternatively, embodiments provide that the shin rest is adjustable and may be located against the shins of patient, and thus support patient shins, in both the first orientation and the second orientation. In some embodiments, the shin rest is slidably mounted with respect to the rotating disc and may be locked into position. In some embodiments, the shin rest further stabilizes the patient by providing a supporting surface to brace the patient. While the rotation speed of the patient support is sufficiently low such that centrifugal forces are negligible and do not destabilize the patient during imaging, in some embodiments, the shin rest may provide stabilization of the patient during rotation.

In some embodiments, the patient support 110 comprises a foot rest 14 (e.g., a heel stop) for sustaining the feet of patient in the second orientation. In some embodiments, the foot rest further sustains the feet of patient in both the first and second orientations of patient support assembly. In some embodiments, the rotating disc, onto which the patient support assembly is mounted, is also the foot rest. In some embodiments, a foot rest (e.g., a raised foot rest and/or a heel stop) is provided as a separate component and is distinct from the rotating disc.

In some embodiments, the foot rest 14 is a heel stop. In some embodiments, the heel stop is adjustably mounted to the rotatable disc. In some embodiments, the heel stop comprises a padded member for receiving the heels of a patient. In some embodiments, the heel stop is adjustable by translating the heel stop. In some embodiments, the heel stop is slidably mounted with respect to the rotating disc and may be locked into position. In some embodiments, a fourth actuator or a fourth set of actuators is provided for adjusting the position of the heel stop. In some embodiments, the heel stop is adjusted to be in a position that facilitates ingress or egress of patient from the patient positioning system, e.g., by positioning the heel stop under the seat member.

In some embodiments, the patient support assembly described herein provides three points of contact with the patient: the seat member, the back rest, and the shin rest. In some embodiments, the patient support assembly in the first (e.g., seated) orientation described herein provides three points of contact with the patient: the seat member, the back rest, and the shin rest. In some embodiments, the patient support assembly in the second (e.g., standing or perched) orientation described herein provides three points of contact with the patient: the seat member, the back rest, and the shin rest. In some embodiments, the patient support assembly in the second (e.g., standing or perched) orientation described herein provides three points of contact with the patient: the back rest, the shin rest, and the foot brace (e.g., heel stop).

In some embodiments, the patient support assembly described herein provides four points of contact with the patient: the foot rest (e.g., as provided by the rotating disc), the seat member, the back rest, and the shin rest. In some embodiments, the patient support assembly in the first (e.g., seated) orientation described herein provides four points of contact with the patient: the foot rest (e.g., as provided by the rotating disc), the seat member, the back rest, and the shin rest. In some embodiments, the patient support assembly in the second (e.g., standing or perched) orientation described herein provides four points of contact with the patient: the foot rest (e.g., as provided by the rotating disc), the seat member, the back rest, and the shin rest. In some embodiments, the patient support assembly described herein provides four points of contact with the patient: the heel stop, the seat member, the back rest, and the shin rest. In some embodiments, the patient support assembly in the first (e.g., seated) orientation described herein provides four points of contact with the patient: the heel stop, the seat member, the back rest, and the shin rest. In some embodiments, the patient support assembly in the second (e.g., standing or perched) orientation described herein provides four points of contact with the patient: the heel stop, the seat member, the back rest, and the shin rest. While all four contact points contact the patient in the first and second orientations of the patient support assembly and provide support to the patient, in some embodiments the shin rest is less important for patient stabilization in the first (e.g., seated) orientation and the seat member is less important for patient stabilization in the second (e.g., standing or perched) orientation. Nevertheless, the shin rest in the first (e.g., seated) orientation helps reproduce the patient and prevent the patient from slouching (e.g., due to fatigue) over time and the seat member in the second (e.g., standing or perched) orientation helps prevent lateral movement of the hips and indexes the patient (as well as supporting some of the load).

Accordingly, the patient support assembly described herein provides at least three main points of contact with a patient to support the patient, e.g., at least three of the foot rest (e.g., as provided by the rotating disc and/or by a heel stop), the seat member, the back rest, and/or the shin rest. The at least three points of contact improve patient comfort by supporting or sustaining the patient by contacting three different regions of the patient body. The patient is thus maintained in a comfortable position for long, uninterrupted time periods during imaging and/or therapy. Further, the at least three points of contact improve patient stability by minimizing and/or eliminating patient movement, e.g., compared to configurations with fewer than three points of contact. For example, in some conventional patient positioning technologies, fewer than three points of contact might require the patient to exert a force to maintain a position, particularly when in the second orientation. The reproducibility of the patient position may also be improved by providing at least three points of contact as described herein.

However, in some patient positions, it may not be necessary for one or more components of the patient support assembly (e.g., the back rest, the seat member, the shin rest, the foot braces (e.g., heel stop), and/or the arm rests) to sustain or support the patient (e.g., in either the first or second configuration). For example, in some embodiments, the patient support assembly sustains the patient at three or more different points along the patient body. In some embodiments, the at least three supported regions of the patient comprise one or more end points of the patient (e.g., the patient feet) or regions near moveable joints of the patient (e.g., knees, shoulders, hips). In this way, the patient support assembly may aid the patient in maintaining a predetermined position.

In some embodiments, the seat member is attached to the patient support assembly by a pivotal mount. By this arrangement, the seat member is positioned to extend outwardly from the back rest when the patient support assembly is in a first orientation to thereby offer support for a seated patient buttocks when that patient back is located against the back rest. Also by this arrangement, the seat member is positioned downward about the pivot to locate toward the same plane as the back rest and thus be positioned away from the patient received by the patient support assembly in a second position.

In some embodiments, the arm rests are adjustably mounted to the patient support assembly so that their position may be adjusted relative to the back rest to accommodate patients of differing size. The adjustability of the arm rests may also facilitate the patient arms being supported in various positions to allow a radiation source to target particular parts of the patient anatomy. For example, in some embodiments, positioning the arm rests at a high vertical location relative to the back rest allows the arm rests to receive the patient arms above the level of the chest and may aid to maintain the patient in a stable position by offering comfortable support. In some embodiments, the arm rests support the weight of the upper arms of the patient and aid in maintaining and reproducing a specific positional arrangement of the patient upper body. In some embodiments, the arm rests further stabilize the patient during movement (translation and/or rotation) of the patient support assembly. In some embodiments, the arm rests support the patient arms in a position where they do not interfere with the imaging and/or treatment beam. For example, in some embodiments, the arm rests position the arms in a comfortable position where there are not between the source and the treatment region. In some embodiments (e.g., relating to treatment of the chest (e.g., relating to treatment of the breast)), one or both arms of a patient is/are at an angle greater than 90 degrees with respect to the torso (e.g., placing one or both arms at shoulder level or above the shoulder) so that the beam contacts the treatment region without contacting the arm(s) of the patient. In other words, embodiments provide arm rests that support the arms of a patient in a comfortable and stable position where they do not interfere with the treatment and/or imaging beam (e.g., over the patient's head) and thus introduce minimal or no additional beam scatter.

In some embodiments, the patient positioning system comprises a head rest that is vertically adjustable in position to accommodate patients of varying size. In some embodiments, the head rest is slidably connected with the back rest to effect the vertical position of the head rest relative to the back rest, e.g., to receive patients of varying size and provide comfortable support. In some embodiments, the patient positioning system in the first orientation is suitable for targeting the head, neck, breast, and/or lungs of a patient with a radiation source.

In some embodiments, the second orientation comprises the seat member folded downwardly about its pivotable connection toward alignment with the plane of the back rest, the back rest adjusted vertically upwards along the slanted axis of the back rest, the shin rest adjusted horizontally away from the back rest, and the arm rests adjusted vertically with respect to the back rest. In some embodiments, the second orientation further comprises a heel stop adjusted horizontally (e.g., by translation of the heel stop in the plane of the rotatable disc). In some embodiments, the heel stop is positioned to contact the patient heels. In some embodiments, the second orientation further comprises the arm rests in various positions rotated along a generally transverse patient axis to comfortably accommodate the patient in a variety of treatment positions.

The patient positioning system adapted to receive a patient in the second orientation, e.g., with a torso angled posteriorly with respect to the vertical axis and having the ankles supported by a shin rest (and, in some embodiments, by a foot brace (e.g., a heel stop)), is advantageous because the patient position is largely self-supporting and comfortable. Accordingly, the patient is able to maintain the required treatment position using this assembly in a comfortable manner for appreciable lengths of time. Nonetheless, in addition to the primary components of the patient support assembly (e.g., the back rest, shin rest, seat member, arm rests, foot brace (e.g., heel stop), and head rest), some embodiments further comprise additional components (e.g., harnesses, inflatable elements, elongate straps, and the like) to provide supplemental support, stability, and/or immobilization.

In some exemplary embodiments, the back rest (e.g., for sustaining or supporting a back of the patient) is mounted to a pillar or post to provide support to the back rest. The pillar is itself mounted to a platform, base, or surface. The patient support assembly further comprises a seat member for sustaining or supporting a posterior, buttocks, or thighs of the patient. The seat member is mounted to the pillar in close proximity to the back rest. In other examples, the seat member is mounted to the back rest. The back rest and the seat member are pivotally mounted to the pillar for adjusting their respective inclinations. Furthermore, vertical height of the pillar is adjustable for adjusting the vertical height of the back rest and seat member.

In some exemplary embodiments, the patient support assembly further comprises a shin rest for sustaining or supporting shins of the patient (e.g., a front part of the patient legs, e.g., between the knees and the ankles). The shin rest is mounted to the platform in front of the back rest and the seat member. The shin rest is offset from the back rest such that it faces the shins of the patient when the patient has a back positioned against the back rest. In some embodiments, the platform comprises a plurality of holes for receiving a complementary mating member of the shin rest mounting base. The holes are provided at several horizontal offsets relative to the back rest, such that the horizontal distance between the back rest and the shin rest is adjusted by mounting the shin rest to a different hole. In some embodiments, mechanisms are provided to provide a continuous adjustment of the horizontal distance between the shin rest and the back rest, e.g., using a rail along which the shin rest may be moved and corresponding locking mechanisms for fixing the shin rest at a specific location along the rail.

The back rest, the seat member, and the shin rest comprise substantially flat surfaces and may further comprise padding for accommodating a respective area of the patient body.

In some embodiments, the patient support assembly further comprises a pair of foot braces (e.g., heel stops) for securing feet of the patient. In some embodiments, the foot braces (e.g., heel stops) are mounted to the platform between the back rest and the shin rest. In some embodiments, the foot braces (e.g., heel stops) are mounted to the rotatable disc between the back rest and the shin rest.

In some embodiments, the foot braces comprise heel stops. In some embodiments, the heel stops are provided such that it provides a surface contacting the heels of the patient when the patient has a back positioned against the back rest. In some embodiments, the platform comprises a plurality of holes for receiving a complementary mating member of the heel stops. The holes are provided at several horizontal offsets relative to the back rest, such that the horizontal distance between the back rest and the heel stops is adjusted by mounting the heel stops to a different hole. In some embodiments, mechanisms are provided to provide a continuous adjustment of the horizontal distance between the heel stops and the back rest, e.g., using a rail along which the heel stops may be moved and corresponding locking mechanisms for fixing the heel stops at a specific location along the rail. In some embodiments, the foot braces comprise straps, clasps, or other arching pieces adapted to fasten over a top side of the patient feet for securing them to the platform. In other examples, a means other than foot braces is provided for securing the patient feet to the platform, such as foot-shaped indentations or raised foot stops.

In some embodiments, the patient support assembly further comprises one or two arm rests or arm supports for sustaining one or both arms of the patient. One or both arm rests are mounted to the back rest at a left and right side of the back rest to receive one or both left and/or right arms of the patient, respectively. The vertical height of the arm rests, as well as their location relative to the back rest, is adjusted for accommodating patients of different sizes and different patient positions. Each arm rest comprises a bent portion for receiving a portion of the upper arm of the patient extending between the shoulder and the elbow. The bent portion is pivotally mounted to arm, which is connected to the back rest, for orientating the bent portion to suit the patient physical dimensions. The arm rests may sustain the arms of the patient in a predetermined position, such as an overhead position as shown, or a downwards, lateral position such that the arms are positioned at respective left and right sides of the patient.

In some embodiments, the patient support assembly in the second configuration supports a patient in a substantially standing position and, furthermore, the arm rests engage the patient upper arms and sustain the arms in an overhead position with the arms being angled vertically upwards and extending above a head of the patient.

In an exemplary embodiment, the second configuration of the patient support assembly sustains a patient in a substantially standing position with the patient thighs at least partly extending along a vertical direction and the patient knees bent relative to the thighs. Furthermore, in some embodiments, the patient back is sustained by the back rest, the patient posterior is sustained by the seat member, and the patient shins are sustained by the shin rest. In some embodiments, the patient back is sustained by the back rest, the patient shins are sustained by the shin rest, and the patient feet (e.g., heels) are supported by the foot braces (e.g., heel stop). In some embodiments, the patient feet are not secured by foot braces, which are positioned behind the patient ankles. In some embodiments, the patient feet (e.g., heels) are secured by foot braces (e.g., heel stop) and the patient shins are not sustained by the shin rest, which is moved apart from the patient shins. In some embodiments, the patient arms are sustained in an overhead position by the arm rests. Alternatively, in some embodiments, the patient arms are positioned to extend downwardly at the lateral sides of the patient.

In exemplary embodiments, the first configuration of the patient support assembly sustains a patient in a seated position with the patient thighs extending along a substantially horizontal direction and the patient knees bent approximately perpendicularly relative to the thighs. Furthermore, in some embodiments, the patient back is sustained by the back rest, the patient posterior is sustained by the seat member, and the patient shins are sustained by the shin rest, thus minimizing and/or eliminating movement that may cause the patient from sliding forwards along the seat member. In some embodiments, the patient feet (e.g., heels) are also sustained by the foot braces (e.g., heel stops). In some embodiments, the patient feet are not secured by foot braces, which are positioned behind the patient ankles. In some embodiments, the patient feet (e.g., heels) are secured by foot braces (e.g., heel stops) and the shin rest is moved apart from the patient shins. In some embodiments, the patient arms are positioned to extend downwardly at the lateral sides of the patient. In some embodiments, the patient arms are sustained in an overhead position by the arm rests.

As described herein, embodiments provide that the patient support 110 is mounted to a rotatable structure, e.g., a rotating disc of a translatable member, to provide rotation of the patient support assembly about a vertical axis. For example, in some embodiments, a platform is mounted to the rotating disc. In some embodiments, the platform is integrally formed with the rotating disc and forms part of the rotating disc.

In some embodiments, the patient support assembly is configured to move or translate along a vertical direction. For example, in some embodiments, the patient support assembly is mounted to and above a scissor-lift mechanism 310, e.g., as described herein. Accordingly, the vertical location of the patient support assembly and of the patient may be adjusted without affecting the configuration of the patient support assembly or the position of the patient relative to the patient support assembly. In some embodiments, the patient support assembly and the translatable member share the same vertical axis.

As described herein, the technology provides a back rest having an adjustable inclination with respect to the vertical axis. In some embodiments, the plane of the back rest is parallel to a vertical axis of the patient support assembly, e.g., to provide a torso of the patient in position that is substantially vertically oriented. In some embodiments, the plane of the back rest is tilted clockwise relative to the vertical axis (e.g., the back rest is inclined posteriorly to the vertical axis), e.g., to provide the patient torso in a position that is tilted posteriorly relative to the vertical axis. In some embodiments, the plane of the back rest is tilted counter-clockwise relative to the vertical axis (e.g., the back rest is inclined anteriorly to the vertical axis), e.g., to provide the patient torso in a position that is tilted anteriorly relative to the vertical axis.

In some embodiments, the configurable patient support 110 is adapted to tilt or pivot relative to a horizontal plane of the translatable member or any other fixed horizontal surface. In some embodiments, the platform 11 is pivotally mounted to the translatable member such that the patient support 110 is tilted, or pivoted, about a point of the platform and the point of tilting is a center point of the platform or any other point located within an area defined by the platform. For example, in some embodiments, the platform is mounted onto a rounded member (e.g., comprising a shape of a sphere, a hemisphere, a portion of a sphere, or other rounded surface) and the platform is able to tilt and rotate relative to the rounded member. Accordingly, pivoting of the platform 11 about the rounded member provides two degrees of freedom in the pitch and roll of the platform relative to the rounded member. In some embodiments, this freedom of movement is used to tilt the patient support 110 and the patient), for example, to adjust the angular position of the patient for alignment to a treatment or imaging plan or to avoid irradiating areas of the patient not intended for radiation treatment or imaging. The mounting of the platform to a rounded member (e.g., coupled to the front of the platform), such as a ball joint, or other rounded joint, provides a fixed point of reference in space around which the angular movements are oriented. In some embodiments, a number of actuators is/are provided for controlling the orientation and magnitude of tilt of the base relative to the rounded member to improve stability of the base. For example, in some embodiments, two actuators are provided at the back of the base—moving both of the rear actuators together pitches the base and moving the rear actuators differently rolls the base. The base moves about the spherical joint at the center of the base and a rounded member coupled to the front of the base allows pitch and roll movement but prevents yaw movement.

In some embodiments, the patient support 110 comprises a pivotable base. In some embodiments, the pivotable base further comprises a platform onto which the patient support assembly is mounted and the platform is pivotally connected by a spherical joint to a stand. The stand is attached to a fixed surface or to the rotating disc of the translatable member. In some embodiments, the pivotable base further comprises a number of actuators (e.g., 1, 2, 3, 4, 5, 6, 7, 8, 9, 10, or more actuators).

For example, in some embodiments, the pivotable base comprises three actuators connected between platform and stand, e.g., to pivot the platform about the spherical joint relative to the stand. In an exemplary embodiment, the three actuators comprise one front actuator located in proximity to the spherical joint and engaging a first side of the platform and two rear actuators located distally to the spherical joint and engaging a second side of the platform opposite the first side. In some embodiments, the actuators produce a pitch movement of the platform, wherein the front actuator provides a push-pull arrangement with the rear actuators, e.g., when the rear actuators expand, the front actuator contracts, and vice versa. In some embodiments, the actuators produce a roll movement of the platform, wherein the rear actuators are in a push-pull arrangement with each other without significant movement in the front actuator. The spherical joint (and thus, the pivot point of the pivotable base) is located offset from a geometrical center of the platform. In some embodiments, the pivot point of the pivotable base is displaced, or offset, from the center of the base and from the isocenter of the treatment or imaging system. In particular embodiments, the actuators are arranged with three actuators in a triangular configuration with the pivot point located in proximity to one of the actuators, which reduces yaw movement arising from a combination of pitch and roll relative to a configuration in which the pivot point is equidistant or substantially equidistant from all the actuators. In some embodiments, the arrangement of the pivot point and the actuators is such that the majority of the load of the patient support assembly and the patient is located between the spherical joint and the rear actuators.

For example, in some embodiments, the pivotable base comprises two actuators connected between platform and stand, e.g., to pivot the platform about the spherical joint at the center of the base and a rounded member (e.g., second spherical joint) coupled to the front of the base prevents yaw movement. In an exemplary embodiment, the front rounded member is located in proximity to the center spherical joint and engages a first side of the platform and two rear actuators are located distally to the spherical joint and engage a second side of the platform opposite the first side. In some embodiments, the rear actuators produce a pitch movement of the platform, wherein the rear actuators provide a push-push or pull-pull arrangement, e.g., both rear actuators expand or both rear actuators contract. In some embodiments, the rear actuators produce a roll movement of the platform, wherein the rear actuators are in a push-pull arrangement with each other, e.g., a first rear actuator expands and a second rear actuator contracts. The spherical joint (and thus, the pivot point of the pivotable base) is located offset from a geometrical center of the platform. In some embodiments, the pivot point of the pivotable base is displaced, or offset, from the center of the base and from the isocenter of the treatment or imaging system. In particular embodiments, the two rear actuators are arranged with the front rounded member in a triangular configuration with the pivot point located in proximity to the rounded member, which reduces and/or eliminates yaw movement arising from a combination of pitch and roll relative to a configuration in which the pivot point is equidistant or substantially equidistant from all the points of the triangle (e.g., comprising the two rear actuators and the rounded member). In some embodiments, the arrangement of the pivot point and the actuators is such that the majority of the load of the patient support assembly and the patient is located between the spherical joint and the rear actuators.

In some embodiments, the patient support 110 is translatable in a horizontal plane, e.g., in addition to being rotatable about a vertical axis. In some embodiments, the patient support 110 is translatable in a horizontal plane orthogonal to the vertical axis of rotation. In some embodiments, the patient support 110 comprises two pairs of parallel rails in orthogonal relation, the patient support 110 being slidably connected to a first pair of rails for translation in a first orthogonal direction and the first set of rails being slidably connected to a second pair of rails for translation in a second orthogonal direction.

Configurable Patent Support

In some embodiments, the technology provides a configurable patient support 110 comprising one or more configurable and movable components, e.g., a back rest 12 (e.g., a configurable and movable back rest), a head rest (e.g., a configurable and movable head rest), an arm rest (e.g., a configurable and movable arm rest), a seat member 511 (e.g., a configurable and movable seat member), a shin rest 13 (e.g., a configurable and movable shin rest), and/or a foot brace 14 (e.g., a configurable and movable foot brace). In some embodiments, the foot brace 14 is a heel stop. In some embodiments, one or more configurable and movable components of the configurable patient support 110 comprises one or more motorized components, e.g., a motorized back rest (e.g., a back rest operatively engaged with a back rest motor), a motorized head rest (e.g., a head rest operatively engaged with a head rest motor), a motorized arm rest (e.g., an arm rest operatively engaged with an arm rest motor), a motorized seat member (e.g., a seat member operatively engaged with a seat member motor), a motorized shin rest (e.g., a shin rest operatively engaged with a shin rest motor), and/or a motorized foot brace (e.g., a foot brace operatively engaged with a foot brace motor). In some embodiments, the motorized foot brace is a motorized heel stop (e.g., a heel stop operatively engaged with a heel stop motor).

In some embodiments, the back rest motor is structured to move (e.g., translate and/or rotate) the back rest, the head rest motor is structured to move (e.g., translate and/or rotate) the head rest, the arm rest motor is structured to move (e.g., translate and/or rotate) the arm rest, the seat member motor is structured to move (e.g., translate and/or rotate) the seam member, the shin rest motor is structured to move (e.g., translate and/or rotate) the shin rest, and/or the foot brace motor (e.g., heel stop motor) is structured to move (e.g., translate and/or rotate) the foot brace (e.g., heel stop). In some embodiments, the technology provides a configurable patient support 110 that is configured in a static configuration. In some embodiments, the technology provides a configurable patient support 110 that is configured in a dynamic configuration (e.g., a configuration that moves to assist patient movement, e.g., for patient ingress and/or for patient egress).

In some embodiments, the technology provides a component (e.g., a computer, a microcontroller, and/or a microprocessor) configured to coordinate control and/or movement of one or more of the motorized components, e.g., the motorized back rest, the motorized head rest, the motorized arm rest, the motorized seat member, the motorized shin rest, and/or the motorized foot brace (e.g., motorized heel stop), to provide the configurable patient support into one or more specific configurations comprising the motorized back rest, the motorized head rest, the motorized arm rest, the motorized seat member, the motorized shin rest, and/or the motorized foot brace (e.g., motorized heel stop) in specified positions. In some embodiments, the configurable patient support 110 may be configured in specific configurations including, e.g., a patient ingress state configured for patient ingress into the patient support; a patient standby state configured to support a patient after the patient has ingressed and while the patient is waiting to be imaged and/or treated (e.g., prior to patient imaging and/or patient treatment); a patient imaging/treatment state configured to support a patient while the patient is being imaged and/or treated; and/or a patient egress state configured for patient egress from the patient support.

In some embodiments, the component (e.g., the computer, the microcontroller, and/or the microprocessor) configured to coordinate control and/or movement of the motorized components (e.g., the motorized back rest, the motorized head rest, the motorized arm rest, the motorized seat member, the motorized shin rest, and/or the motorized foot brace (e.g., motorized heel stop)) to provide the configurable patient support 110 into one or more specific configurations is configured to actuate and/or control the back rest motor, the head rest motor, the arm rest motor, the seat member motor, the shin rest motor, and/or the foot brace motor (e.g., heel stop motor). In some embodiments, actuating one or more of the motorized components (e.g., the motorized back rest, the motorized head rest, the motorized arm rest, the motorized seat member, the motorized shin rest, and/or the motorized foot brace (e.g., motorized heel stop)) comprises setting one or more of the motorized components into an "on" state (e.g., by providing electric current and/or electric voltage to the one or more motorized components (e.g., to a motor operatively coupled to a motorized component)) or into an "off" state (e.g., by eliminating electric current and/or electric voltage to the one or more motorized components (e.g., to a motor operatively coupled to a motorized component)). In some embodiments, actuating one or more of the motorized components (e.g., the motorized back rest, the motorized head rest, the motorized arm rest, the motorized seat member, the motorized shin rest, and/or the motorized foot brace (e.g., motorized heel stop)) comprises controlling the linear and/or rotational speed; and/or controlling the linear and/or rotational acceleration of the one or more motorized components (e.g., by controlling the linear and/or rotational speed; and/or controlling the linear and/or rotational acceleration of a motor operatively coupled to a motorized component).

In some embodiments, the technology comprises software (e.g., a software object) comprising instructions for a specified position and/or specified movement (e.g., coordinated movement) of one or more of the motorized components, e.g., the motorized back rest, the motorized head rest, the motorized arm rest, the motorized seat member, the motorized shin rest, and/or the motorized foot brace (e.g., motorized heel stop); and associated computer memory to store the software and/or to store data describing one or more positions of the configurable patient support and/or one or more positions of the motorized components of the configurable patient support. In some embodiments, a method to move one or more of the motorized components is provided as an object method. In some embodiments, data and/or a data structure describing a position and/or specified movements of the motorized components is provided as an object data structure. Some embodiments provide an object-oriented pipeline for moving one or more of the motorized components, e.g., comprising one or more software objects, to move one or more of the motorized components.

In some embodiments, a position of the configurable patient support 110 and/or a position of the motorized components of the configurable patient support is specific for an individual patient; is specific for an individual imaging and/or treatment plan; and/or is specific for an individual imaging and/or treatment plan for an individual patient. In some embodiments, data and/or a data structure describing a position of the motorized components of the configurable patient support is provided as an object data structure.

In some embodiments, the configurable patient support 110 is configured for ingress of a patient to the patient support, e.g., the configurable patient support is configured to move to a patient ingress state, e.g., to provide a static configuration that is a patient ingress state. The patient support configured in the patient ingress state comprises the back rest, the head rest, the arm rest, the seat member, the shin rest, and/or the foot brace (e.g., heel stop) in positions that facilitate ingress of the patient to the patient support. For example, the back rest, the head rest, the arm rest, the seat member, the shin rest, and/or the foot brace (e.g., heel stop) are in positions that allow easy access of the patient to the patient support and do not hinder ingress of the patient to the patient support. In some embodiments, the patient ingress state is configured to facilitate ingress of a patient to a standing position. In some embodiments, the patient ingress state is configured to facilitate ingress of a patient to a sitting position.

In some embodiments, the configurable patient support 110 is configured to provide a dynamic configuration that assists ingress of a patient to the patient support, e.g., by supporting the patient and/or by applying a force to the patient to guide, push, or pull the patient into a position on the configurable patient support. For example, in some embodiments, the configurable patient support 110 is configured to contact the patient, operatively engage the patient, and apply a force to at least a portion of the patient (e.g., an arm, a leg, a torso, a head, a foot, a hand, a buttocks, a knee, an elbow) to facilitate ingress into the patient support. In some embodiments, one or more of the back rest, the head rest, the arm rest, the seat member, the shin rest, and/or the foot brace (e.g., heel stop) contacts the patient, operatively engages the patient, and applies a force to at least a portion of the patient (e.g., an arm, a leg, a torso, a head, a foot, a hand, a buttocks, a knee, an elbow) to facilitate ingress of the patient into the patient support. In some embodiments, one or more of the back rest, the head rest, the arm rest, the seat member, the shin rest, and/or the foot brace (e.g., heel stop) moves to guide the patient to facilitate ingress of the patient into the patient support.

In some embodiments, the configurable patient support 110 is configured to move to a static configuration that is a patient standby state, e.g., to provide a patient standby state that is a stable and comfortable support for a patient who has ingressed into the patient support and who is waiting to be imaged and/or treated (e.g., the patient has ingressed into the patient support but is not yet in a final position for being imaged or treated). The patient standby state may be the same or similar to the patient imaging/treatment state and, in some embodiments, the patient standby state is different than the patient imaging/treatment state. The patient standby state may comprise one or more of the back rest, the head rest, the arm rest, the seat member, the shin rest, and/or the foot brace (e.g., heel stop) in standby positions that are different than the positions of the back rest, the head rest, the arm rest, the seat member, the shin rest, and/or the foot brace (e.g., heel stop) positions in the patient ingress state. In some embodiments, the patient support configured in the patient standby state comprises the back rest, the head rest, the arm rest, the seat member, the shin rest, and/or the foot brace (e.g., heel stop) in positions that provide comfortable support to the patient after ingress of the patient and before imaging and/or treatment of the patient. For example, the back rest, the head rest, the arm rest, the seat member, the shin rest, and/or the foot brace (e.g., heel stop) are in positions that provide a comfortable seated and/or standing position that supports the body of a patient and that imposes minimal restriction of movement on the patient prior to imaging and/or treatment. In some embodiments, the patient standby state comprises one or more of the back rest, the head rest, the arm rest, the seat member, the shin rest, and/or the foot brace (e.g., heel stop) in standby positions that hinder egress from the patient support, though such hindrance is a consequence of the patient standby configuration and not necessarily required for the patient standby configuration.

Figure 5A:
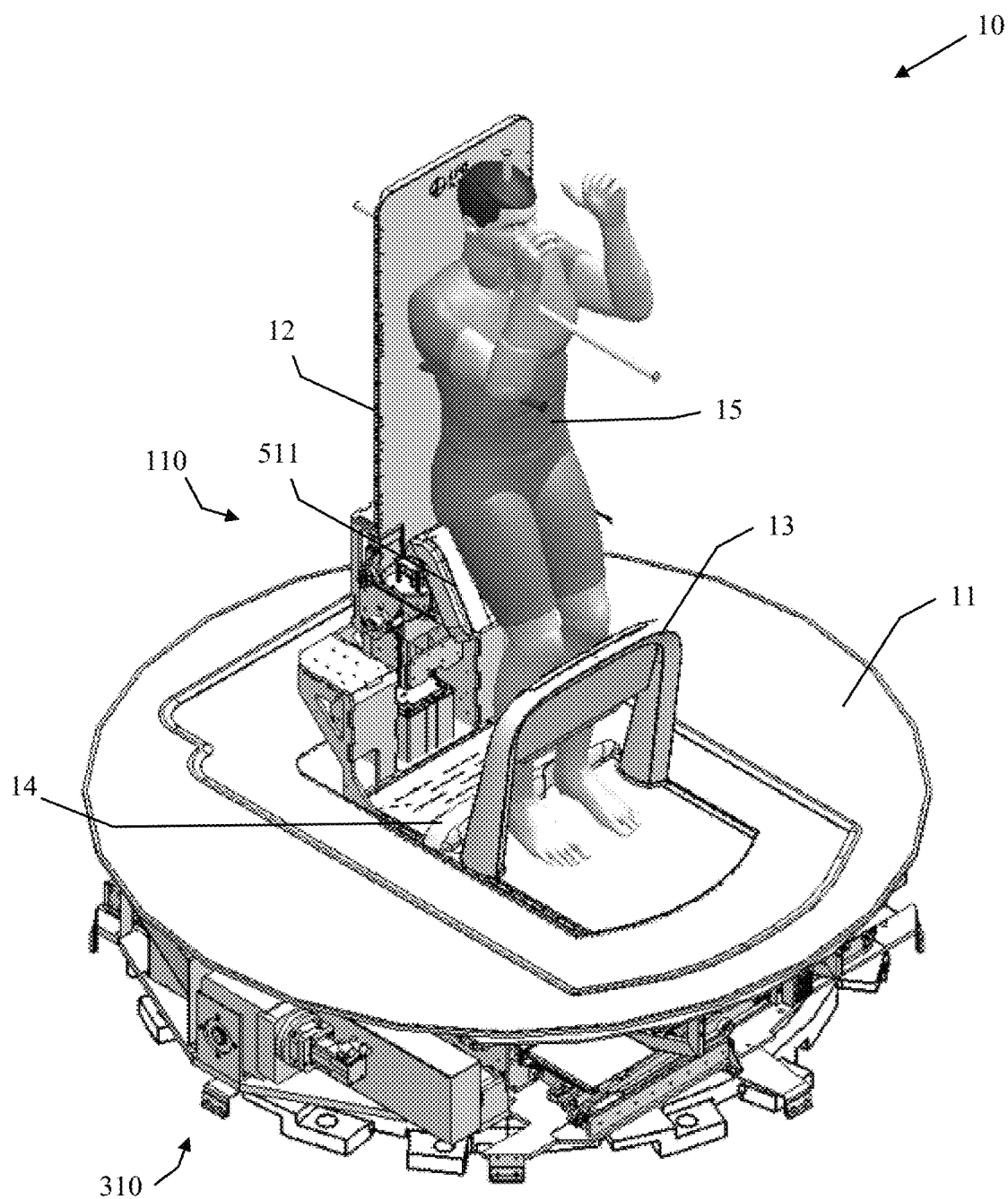
FIG. 5A is a perspective view of a patient in the patient positioning system of FIG. 1.
Figure 5B:
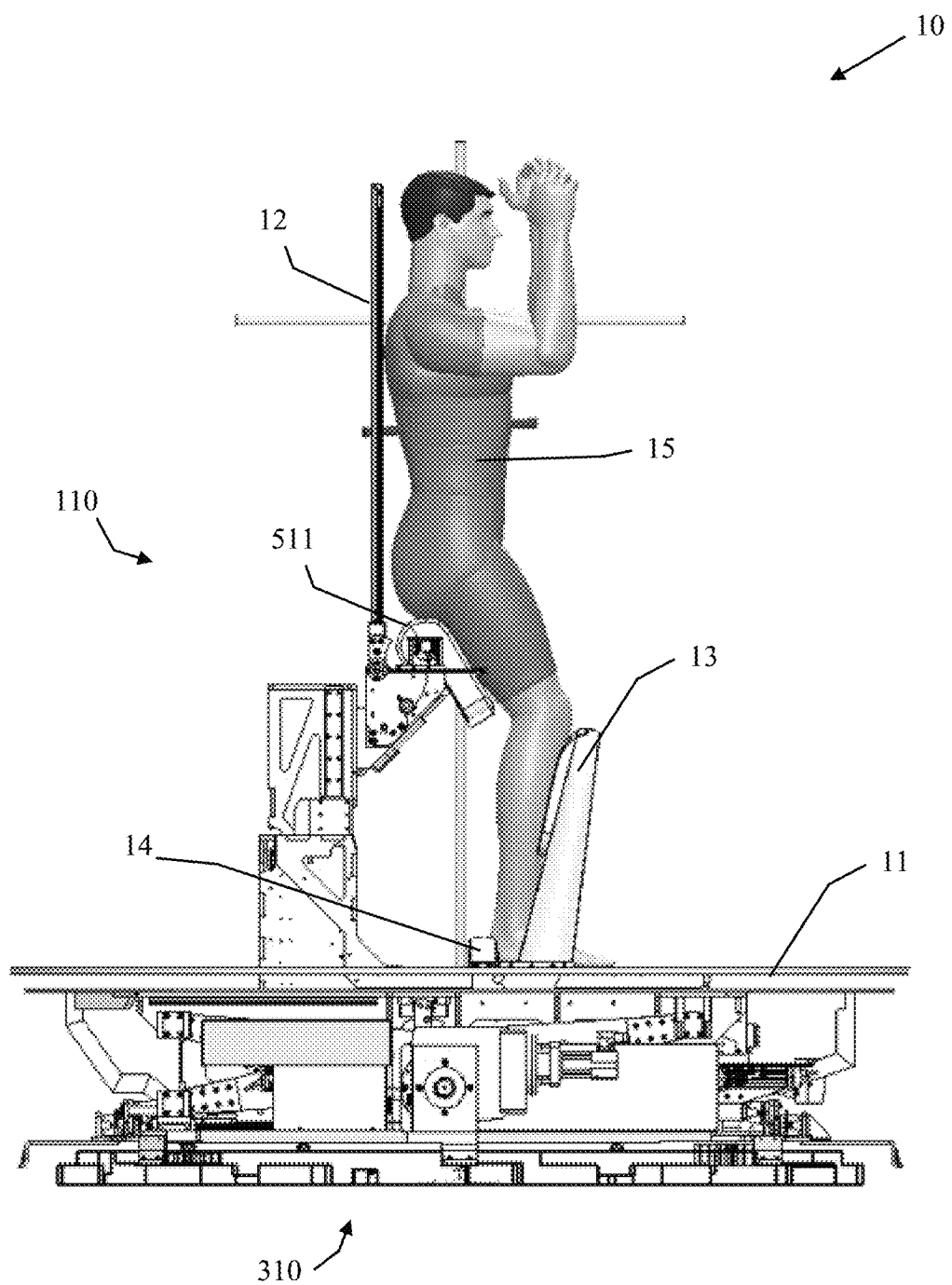
FIG. 5B is a side view of the patient in the patient positioning system of FIG. 5A.
Figure 5C:
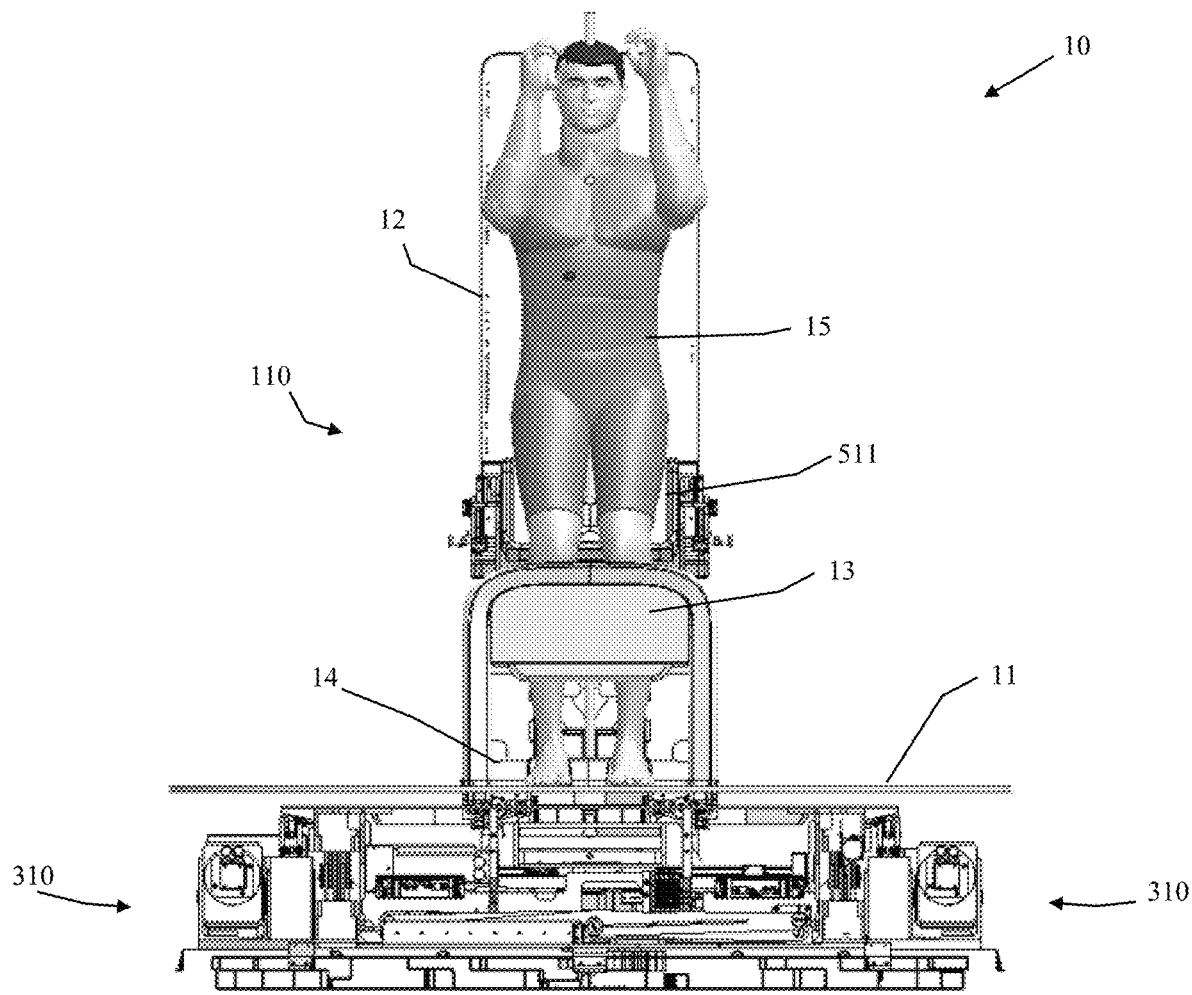
FIG. 5C is a front view of the patient in the patient positioning system of FIG. 5A.

In some embodiments, the configurable patient support 110 is configured to move to a static configuration that is a patient imaging/treatment state (FIGS. 5A-5B), e.g., to provide a patient imaging/treatment state that is a stable and comfortable support for maintaining the patient 15 in an imaging position and/or a treatment position (e.g., a motionless, substantially motionless, and/or effectively motionless position) for imaging and/or for treatment.

In some embodiments described herein, the radiation source (e.g., an imaging beam and/or a treatment beam) is fixed in position such that the relative movement between the patient and the treatment or imaging beam is effected by the movement of the patient positioning system and/or the patient support. One of ordinary skill in the art of medical imaging and radiotherapy understands that some motion of the patient may negatively affect image quality and that some motion of the patient is included as a part of the imaging process. Accordingly, as used herein, a "motionless position" (e.g., a "substantially motionless" and/or an "effectively motionless position") of a patient refers to a position of the patient in which the patient is motionless with respect to the patient positioning system and/or with respect to the patient support. A patient in a "motionless position" (e.g., a "substantially motionless" and/or an "effectively motionless position") may be but is not necessarily motionless with respect to a treatment or imaging beam, e.g., as the patient and patient support are rotated and/or translated with respect to the treatment or imaging beam.

In some embodiments, the configurable patient support 110 moves from a patient ingress state to the patient imaging/treatment state. In some embodiments, the configurable patient support 110 moves from a patient standby state to the patient imaging/treatment state. The patient imaging/treatment state may be the same or similar to the patient standby state and, in some embodiments, the patient imaging/treatment state is different than the patient standby state. The patient imaging/treatment state may comprise one or more of the back rest, the head rest, the arm rest, the seat member, the shin rest, and/or the foot brace (e.g., heel stop) in imaging/treatment positions that are different than the positions of the back rest, the head rest, the arm rest, the seat member, the shin rest, and/or the foot brace (e.g., heel stop) positions in the patient ingress state and/or in the patient standby state. In some embodiments, the patient support configured in the patient imaging/treatment state comprises the back rest, the head rest, the arm rest, the seat member, the shin rest, and/or the foot brace (e.g., heel stop) in positions that provide stable and comfortable support for maintaining the patient in an imaging position and/or a treatment position (e.g., a motionless, substantially motionless, and/or effectively motionless position) for imaging and/or for treatment of the patient. For example, the back rest, the head rest, the arm rest, the seat member, the shin rest, and/or the foot brace (e.g., heel stop) in the patient imaging/treatment state are in positions that provide a comfortable seated and/or standing position that supports the body of a patient and that minimizes and/or eliminates patient motion during imaging and/or treatment.

In some embodiments, the configurable patient support 110 is configured to move to a static configuration that is a patient pre-egress state, e.g., to provide a patient pre-egress state that is a stable and comfortable support for a patient who has been imaged and/or treated and who is waiting to egress from the patient support. The patient pre-egress state may be the same or similar to the patient imaging/treatment state and, in some embodiments, the patient pre-egress state is different than the patient imaging/treatment state. In some embodiments, the patient pre-egress state is the same or similar to the patient standby state. The patient pre-egress state may comprise one or more of the back rest, the head rest, the arm rest, the seat member, the shin rest, and/or the foot brace (e.g., heel stop) in pre-egress positions that are different than the positions of the back rest, the head rest, the arm rest, the seat member, the shin rest, and/or the foot brace (e.g., heel stop) positions in the patient imaging/treatment state. The patient pre-egress state may comprise one or more of the back rest, the head rest, the arm rest, the seat member, the shin rest, and/or the foot brace (e.g., heel stop) in pre-egress positions that are different than the positions of the back rest, the head rest, the arm rest, the seat member, the shin rest, and/or the foot brace (e.g., heel stop) positions in the patient egress state. In some embodiments, the patient support configured in the patient pre-egress state comprises the back rest, the head rest, the arm rest, the seat member, the shin rest, and/or the foot brace (e.g., heel stop) in positions that provide comfortable support to the patient after imaging and/or treatment of the patient and prior to egress of the patient from the patient support. For example, the back rest, the head rest, the arm rest, the seat member, the shin rest, and/or the foot brace (e.g., heel stop) are in positions that provide a comfortable seated and/or standing position that supports the body of a patient and that imposes minimal restriction of movement on the patient while the patient waits to egress. In some embodiments, the patient pre-egress state comprises one or more of the back rest, the head rest, the arm rest, the seat member, the shin rest, and/or the foot brace (e.g., heel stop) in pre-egress positions that hinder egress from the patient support, though such hindrance is a consequence of the patient pre-egress configuration and not necessarily required for the patient pre-egress configuration.

In some embodiments, the configurable patient support 110 is configured to provide a dynamic configuration that assists egress of a patient from the patient support, e.g., by providing support for the patient and/or by applying a force to the patient to guide, push, or pull the patient out of the patient support and/or away from the patient positioning assembly. For example, in some embodiments, the configurable patient support is configured to contact the patient, operatively engage the patient, and apply a force to at least a portion of the patient (e.g., an arm, a leg, a torso, a head, a foot, a hand, a buttocks, a knee, an elbow) to facilitate egress out of the patient support and/or away from the patient positioning assembly. In some embodiments, one or more of the back rest, the head rest, the arm rest, the seat member, the shin rest, and/or the foot brace (e.g., heel stop) contacts the patient, operatively engages the patient, and applies a force to at least a portion of the patient (e.g., an arm, a leg, a torso, a head, a foot, a hand, a buttocks, a knee, an elbow) to facilitate egress of the patient out of the patient support and/or away from the patient support assembly. In some embodiments, one or more of the back rest, the head rest, the arm rest, the seat member, the shin rest, and/or the foot brace (e.g., heel stop) moves to guide the patient to facilitate egress of the patient out of the patient support and/or away from the patient support assembly.

In some embodiments, the configurable patient support 110 is configured to move to a static configuration for egress of a patient out of the patient support and/or away from the patient support assembly, e.g., the configurable patient support is configured to move to a patient egress state, e.g., to provide a static configuration that is a patient egress state. The patient support configured in the patient egress state comprises the back rest, the head rest, the arm rest, the seat member, the shin rest, and/or the foot brace (e.g., heel stop) in positions that facilitate egress of the patient out of the patient support and/or away from the patient support assembly. For example, the back rest, the head rest, the arm rest, the seat member, the shin rest, and/or the foot brace (e.g., heel stop) are in positions that allow easy movement of the patient away from the patient support and do not hinder egress of the patient from the patient support. In some embodiments, the patient egress state is configured to facilitate egress of a patient in a standing position. In some embodiments, the patient egress state is configured to facilitate egress of a patient in a sitting position, e.g., by assisting a patient to stand and move out of the patient support and/or away from the patient support assembly.

As described above, embodiments of the technology comprise motorized components (e.g., a motorized back rest (e.g., a back rest operatively engaged with a back rest motor), a motorized head rest (e.g., a head rest operatively engaged with a head rest motor), a motorized arm rest (e.g., an arm rest operatively engaged with an arm rest motor), a motorized seat member (e.g., a seat member operatively engaged with a seat member motor), a motorized shin rest (e.g., a shin rest operatively engaged with a shin rest motor), and/or a motorized foot brace (e.g., a foot brace operatively engaged with a foot brace motor)); a component (e.g., a computer, a microcontroller, and/or a microprocessor) configured to coordinate control and/or movement of one or more of the motorized components; software comprising instructions for positions and/or movement (e.g., coordinated movement) of one or more of the motorized components; and associated computer memory (e.g., non-transitory computer readable medium) to store the software and/or to store data describing one or more positions of the configurable patient support and/or one or more positions of the motorized components of the configurable patient support. In some embodiments, the motorized foot brace is a motorized heel stop (e.g., a heel stop operatively engaged with a heel stop motor).

Accordingly, embodiments of the technology provide automated and reproducible setup of the configurable patient support (e.g., automated and reproducible setup of one or more of the back rest, the head rest, the arm rest, the seat member, the shin rest, and/or the foot brace (e.g., heel stop)). For example, embodiments of the technology provide customized configurations for individual patients, individual treatment plans, and/or individual imaging plans that are described by parameters that are stored in a computer memory and that can be recalled for reproducing an individualized configuration for any particular patient and/or treatment plan. The parameters describe the position, path of travel, speed, and/or acceleration of one or more of the back rest, the head rest, the arm rest, the seat member, the shin rest, and/or the foot brace (e.g., heel stop) to provide any of the static and/or dynamic configurations described herein (e.g., the patient ingress state, the dynamic configuration that assists ingress of a patient to the patient support, the patient standby state, the patient imaging/treatment state, the patient pre-egress state, the dynamic configuration that assists egress of a patient from the patient support, and/or the patient egress state). In some embodiments, pre-defined standardized configurations are provided for particular classes of patients (e.g., a demographic based on height, weight, imaging or treatment area, gender, race, or other demographic data). In some embodiments, the pre-defined standardized configurations provide a base configuration that is modified to accommodate the specific and individualized patient characteristics and/or specific and individualized imaging and/or treatment plan of the patient.

Accordingly, the technology provides advantages relative to previous technologies, e.g., by providing automated setup that reduces setup time and by providing reproducible setup that increases treatment effectiveness and safety.

Six Degrees-of-Freedom Movement and Compensation

In some embodiments, the patient support 110 is configured to move with six degrees-of-freedom and further includes active compensation in at least one degree-of-freedom while another degree-of-freedom is adjusted. In some embodiments, the active compensation is utilized to maintain a desired patient region (e.g., a treatment zone, an imaging zone) aligned with a treatment or imaging beam. In other words, the compensation ensures the patient treatment zone is aligned with the isocenter.

For example, when a patient 15 is positioned in the patient support 110 that moves to pitch (rotation about an X-axis) or roll (rotation about a Y-axis), the patient support also translates in an X-direction or a Y-direction to maintain the desired patient region aligned with a treatment or imaging beam. In other words, rotation of the patient support assembly may move portions of the patient away from an isocenter beam and such movement may be compensated by corresponding translation to realign. The amount of compensation depends on the amount of rotation and where the desired patient region is located. In some embodiments, a combination of X-direction and Y-direction translation compensates for a desired patient region moving in an arc trajectory away from the isocenter beam. In some embodiments, the technology provides a configurable patient support 110 that is movable with a multi-axis actuator system. See, e.g., U.S. patent application Ser. No. 16/649,337, published as U.S. Pat. App. Pub. No. 20200268327, incorporated herein by reference.

Figure 6A:
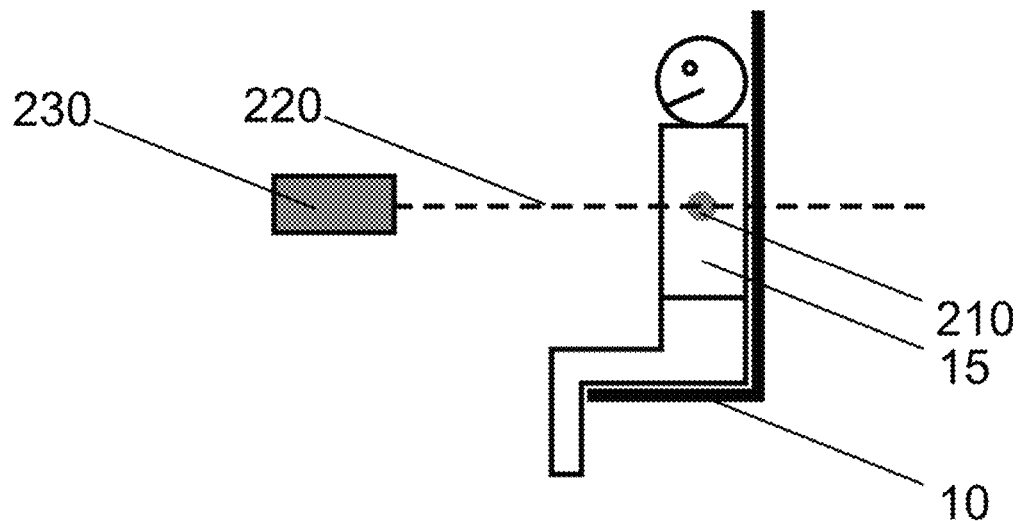
FIG. 6A is a side view of a patient in the patient positioning system of FIG. 1 in a first orientation in which a desired patient region is aligned with a treatment and/or imaging beam.
Figure 6B:
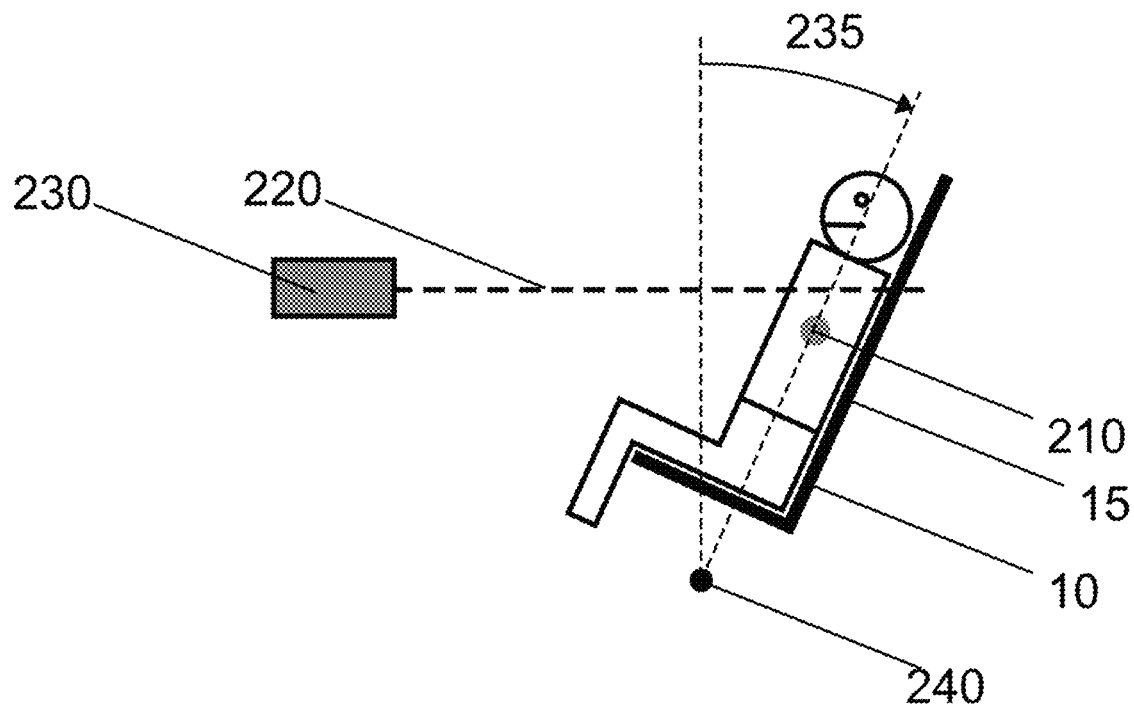
FIG. 6B is a side view of the patient and patient positioning system of FIG. 1 in a second orientation after the patient positioning system and the patient shown in FIG. 6A have been rotated about an axis, which causes the desired patient region to be misaligned with the treatment and/or imaging beam.
Figure 6C:
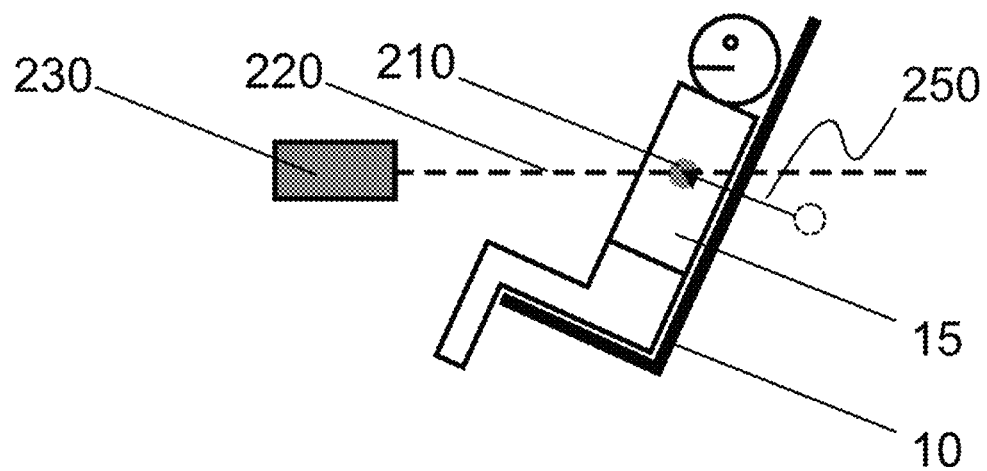
FIG. 6C is a side view of the patient and patient positioning system shown in FIG. 1 in a third orientation after the patient positioning system and the patient shown in FIG. 6B have been translated to realign the desired patient region with the treatment and/or imaging beam.

With reference to FIGS. 6A-6C, compensation is illustrated as sequential steps. FIG. 6A illustrates the patient 15 in the patient positioning system 10 in a first orientation. The imaging and/or treatment beam 220 produced by the source 230 is aligned with the desired patient region 210.

FIG. 6B illustrates the patient 15 in the patient positioning system 10 in a second orientation that has been rotated 235 about an axis 240 (e.g., to produce a pitch or roll of the patient positioning system and the patient). As a result of the rotation (e.g., pitch and/or roll) shown in FIG. 6B, a desired patient region 210 has moved out of alignment with the imaging and/or treatment beam 220 (e.g., the desired patient region 210 has moved out of alignment with an isocenter).

FIG. 6C illustrates the patient 15 in the patient positioning system 10 in a third orientation that has been compensated (e.g., by translating 250 the patient positioning system 10 and the patient 15). Specifically, the patient positioning system 10 is translated 250 to re-align the desired patient region 210 with the imaging and/or treatment beam 220 (e.g., to re-align the desired patient region 210 with the isocenter). In other words, the patient positioning system 10 and patient 15 positioned thereon are translated to compensate for the rotation (e.g., pitch and/or roll) and thus to maintain the desired patient region 210 in alignment with the imaging and/or treatment beam 220 (e.g., with the isocenter) when the patient positioning system 10 is rotated or pivoted.

The technology is not limited to the embodiment shown in FIGS. 6A-6C wherein the rotation is from a vertical position to a reclining position and the translation is forward and up. The technology comprises compensation for rotation about any axis or plurality of axes and appropriate compensation in one, two, and/or three dimensions. In some embodiments, a first rotation is compensated using a second rotation. In some embodiments, a first translation is compensated by a second translation. In some embodiments, a rotation is compensated by a translation. In some embodiments, a translation is compensated by a rotation. In some embodiments, the compensation (e.g., translation and/or rotation) occurs simultaneously or substantially simultaneously to the movement that is being compensated for (e.g., translation and/or rotation).

In some embodiments, the compensation is based on a known and fixed isocenter height. For example, for a shorter (e.g., sitting) patient on a low seat that is positioned by placing the platform high to lift them to the beam height, a small translation will be needed to compensate for the tilt of the platform because the radius of the circle from the isocenter to the platform is small. On the other hand, for a taller patient on a higher seat, the platform is lower to place the treatment site at the isocenter. Accordingly, the radius between the platform and the isocenter is larger and thus requires more compensation. The height of the platform is known and the height of the seat is known, which together define the amount of compensation needed for any measured pitch and/or roll.

Alignment of the patient positioning system, patient positioning apparatus, a patient support, a patient, a quality assurance device, etc. and technologies for compensation of rotations and translations are also discussed in U.S. Pat. App. Ser. No. 63/399,862, which is incorporated herein by reference.

Conventional adjustment systems require an iterative process to move various axes that are cross coupled to achieve the desired compensation. In other words, conventional approaches to compensation involve iterative trial and error.

Advantageously, the patient positioning system 10 has less mechanical flex compared to conventional systems. In conventional systems, mechanical flex of components can produce variation in the patient positioning with respect to the beam line and result in an inaccurate system isocenter. The flex in the systems typically depends on the positioning of the patient and the weight of the patient. Conventional systems (e.g., robotic arms) have large masses that overhang from a base. For example, in some conventional systems, a large gantry rotates about a patient and mechanical flex reduces the accuracy and/or precision of locating the isocenter. The further the patient is moved out and away from the base, the larger the resulting mechanical flex. In addition, the patient weight presents an additional variable in the amount of mechanical flexing occurring in conventional systems. Conventional approaches to align and compensate for mechanical flex include lasers that are not very accurate and portal imaging that presents additional radiation dose to the patient. The conventional approaches to compensate for mechanical flex must be repeated for each session and increase the setup complexity and time. In contrast, the technology provided herein comprising a patient positioning system defines (e.g., locates) the system isocenter much more precisely and/or accurately. For instance, sometimes treatment comprises relocating a tumor to the system isocenter, which is associated with moving the patient positioning system. The technology described herein provides a precise and accurate relocation because the accuracy of rotation and/or translation of the patient positioning system is increased relative to conventional technologies.

In the illustrated embodiment, the six degrees-of-freedom are designed such that the unsupported amount of overhang does not vary and remains constant regardless of the patient position. As such, the amount of mechanical flex in the patient positioning system disclosed herein is eliminated and/or minimized as a patient is repositioned within the patient positioning system. Embodiments of the technology minimize flex by minimizing the amount of unsupported overhang. In other words, the patient positioning system moves with the patient in a manner that decouples variable weight of different patients from the amount of mechanical flexing that occurs.

In some embodiments, the amount of mechanical flex occurring is characterized by a model that combines flex measurements for a range of positions (without a patient) and flex measurements with various loads. In some embodiments, a deflection correction table is created based on the model and automatically applied as the patient positioning system moves. In some embodiments, data for such a model is captured with an image guidance system or suitable quality assurance tool. See, e.g., U.S. Pat. App. Ser. No. 63/396,444, incorporated herein by reference.

Advantageously, the patient positioning system disclosed herein compensates for the mechanical flex automatically for a variety of patient weights in a variety of patient positions. Conventional designs require an image of the patient in the treatment position to account for mechanical flex, which increases patient imaging dose and setup time.

In conventional CT scanning, X-rays are generated by an X-ray tube and an X-ray detector is mounted opposite the X-ray tube. Acquiring CT image data comprises recording multiple radiographs as a gantry holding the tube and detector rotates through 360 degrees of rotation. Due to the mass of conventional gantries, gravity causes mechanical flex in the gantry support arms of the source and/or the detector and can move the gantry axis of rotation. Accordingly, conventional CT scanning systems often require correction of CT scan images to compensate for geometric nonidealities in the rotation of the gantry system caused by gravity. While the flex is less of an issue with CT scanners because they conventionally comprise a balanced ring, cone beam CT (CBCT) scanners remain problematic because they often have substantial flex caused by massive overhanging arms.

In some embodiments, the scanner does not move the imaging source or detector and does not produce mechanical flex that compromises image quality. In other words, by not having a rotating source or detectors, no complicated correction for mechanical flex of the source or detector is required.

Chain Drive and Scissor Lift

In some embodiments, the patient positioning system 10 comprises a scissor lift mechanism 310, e.g., to translate the patient support assembly 10 along a vertical direction. In some embodiments, the patient support assembly 10 is mounted to and above the scissor lift mechanism 310. In the illustrated embodiment, the patient positioning system 10 includes two scissor lift mechanisms 310 placed on opposite sides.

Figure 7A:
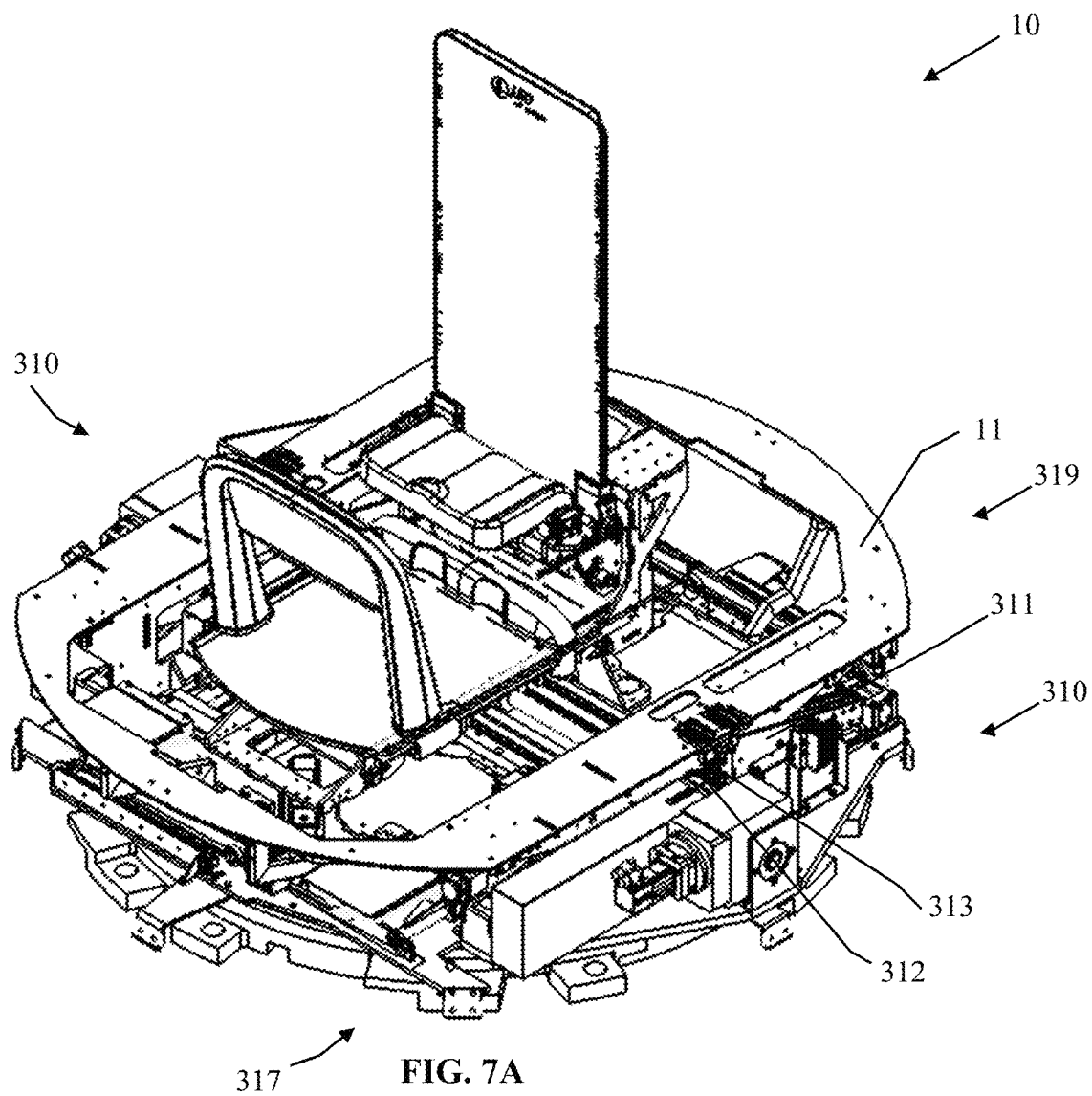
FIG. 7A is a perspective view of the patient positioning system of FIG. 1 in a collapsed vertical position.
Figure 7B:
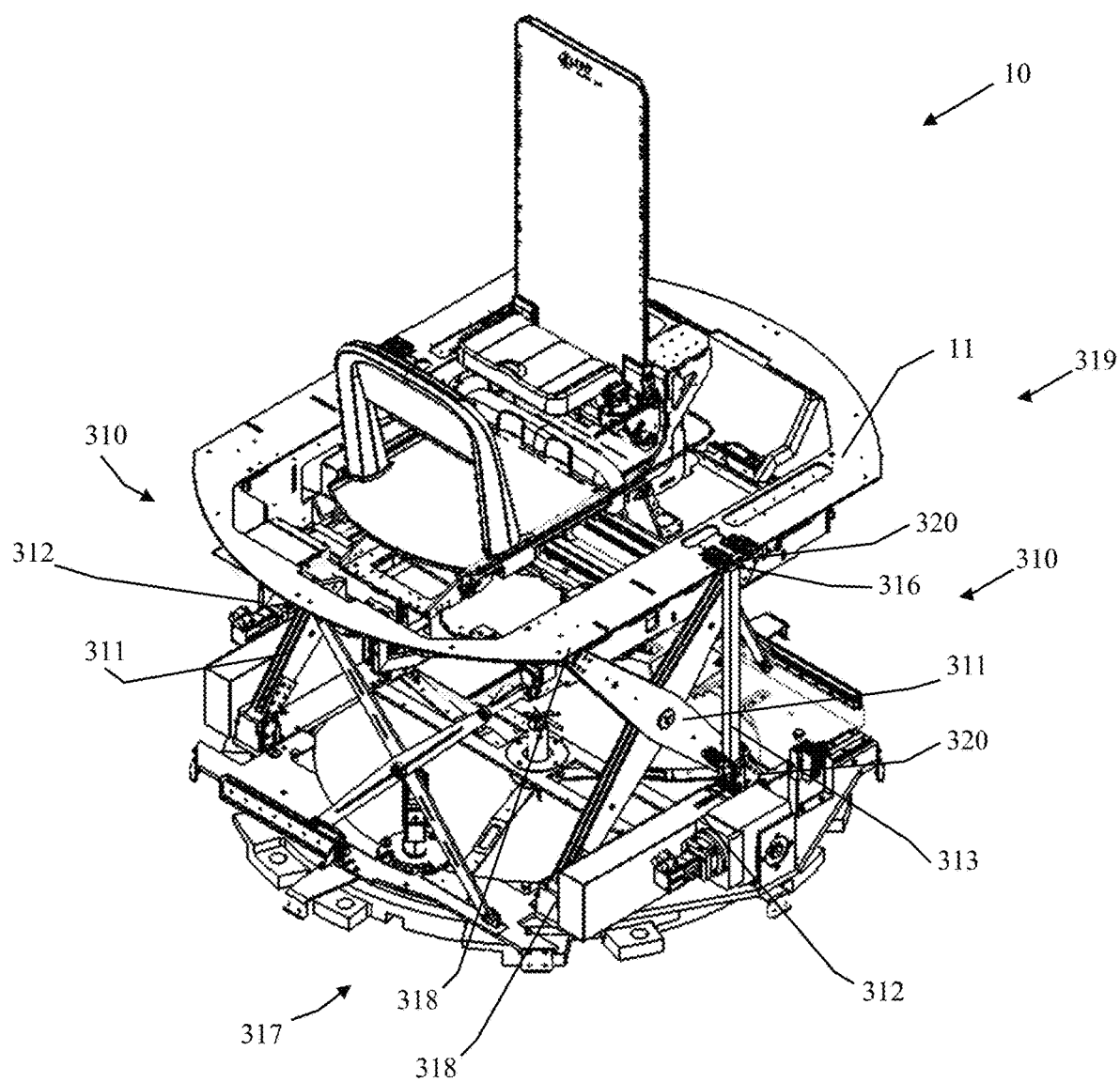
FIG. 7B is a perspective view of the patient positioning system of FIG. 1 in an extended vertical position.

With reference to FIGS. 7A and 7B, the scissor lift mechanisms 310 are illustrated in a fully retracted (collapsed) position (FIG. 7A) and in a fully extended position (FIG. 7B). The scissor lift mechanism 310 disclosed herein includes a scissor frame 311 and a chain drive actuator 312 configured to move the scissor lift mechanism 310 between the retracted and extended positions. In the illustrated embodiment, a front side 317 of the scissor frame 311 includes fixed ends 318 that are fixed with respect to the platform 11 and a rear side 319 of the scissor frame 311 includes movable ends 320 that are slidable with respect to the platform 11.

Figure 8:
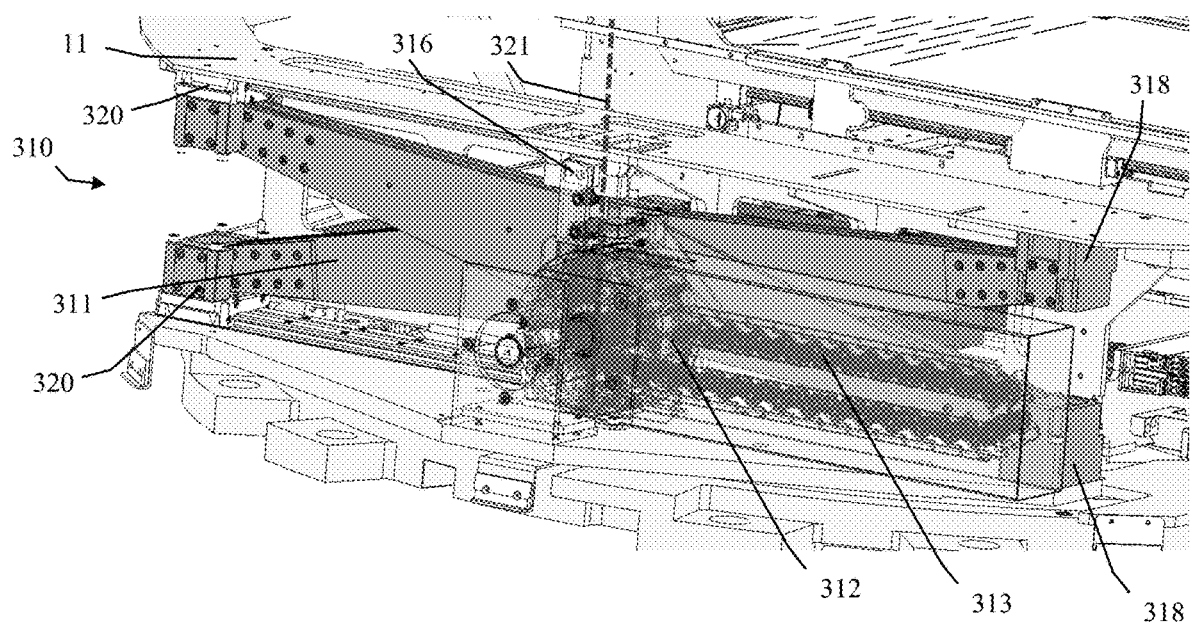
FIG. 8 is a perspective view of a scissor lift mechanism, with portions shown transparent.
Figure 9:
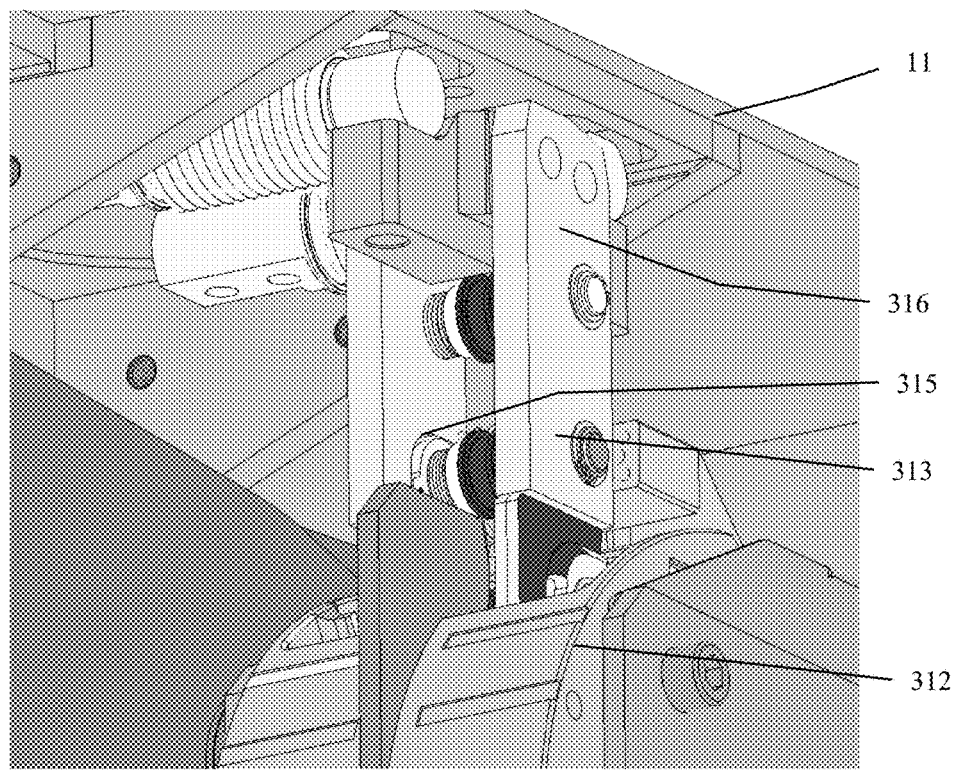
FIG. 9 is a partial perspective view of a chain drive actuator of the scissor lift mechanism of FIG. 8.

With reference to FIGS. 8 and 9, in some embodiments, the chain drive actuator 312 is a push chain drive including a housing 317 and a chain 313. The chain 313 includes individual links 314 with an interlocking profile 315 enabling the chain 313 to roll or fold-up in one direction to form a rigid thrust device. In particular, an end 316 of the chain 313 is coupled to the platform 11 and applies a vertical force to the platform 11 as the chain 313 is driven upwards from the housing 317.

Conventional scissor lifts include conventional actuators that are designed for peak loads that occur at the end of travel of the scissor frame. For example, the force required with the scissor frame in a collapsed configuration is larger than when the scissor frame is partially extended. Conventional actuator designs are either overdesigned to handle the peak load conditions (which is inefficient during other loading conditions) or struggle to lift the platform when the platform is at its lowest point and peak load.

With reference to FIG. 8, the chain drive actuator 312 is positioned at a midpoint 321 of the scissor frame 311 when the scissor frame 311 is in the collapsed position. As such, the force required by the chain drive actuator 312 is approximately constant throughout travel of the frame 311. In other words, there is a constant relationship between force required by the chain drive actuator 312 and distance of travel in the scissor frame 311. The weight distribution through the disclosed scissor assembly 310 is also improved when compared to conventional scissor lift mechanisms.

Advantageously, the disclosed scissor lift assembly 310 is compact. In particular, the chain drive actuator 312 is a compact actuator capable of the travel required between the fully collapsed and fully extended positions. Unlike conventional actuators that have a long overall package to provide the desired travel, the chain drive actuator 312 disclosed herein provides the required travel for the scissor frame 311 in a compact form. In some embodiments, the chain drive actuator 312 provides approximately 1 ton of force.

Weight Sensing

In some embodiments, the patient positioning system 10 includes a weight sensing assembly 410 having at least one load cell 411. In the illustrated embodiment, the weight sensing assembly 410 includes four load cells 411. In some embodiments, the load cells 411 are strain-based load cells. In some embodiments, the load cell is a SSM11 Load cell available from Variohm Eurosensor.

Figure 10:
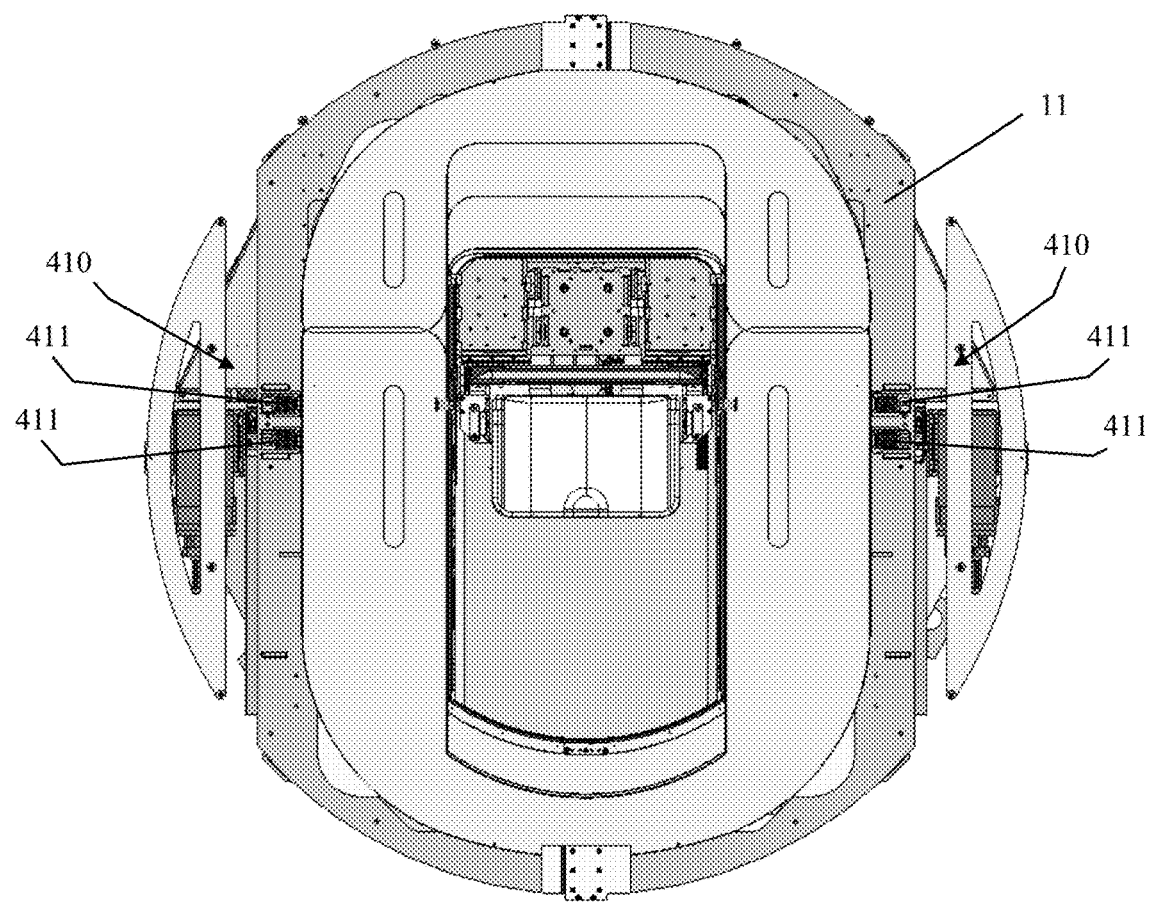
FIG. 10 is a top view of the patient positioning system of FIG. 1, illustrating a weight sensing assembly.
Figure 11:
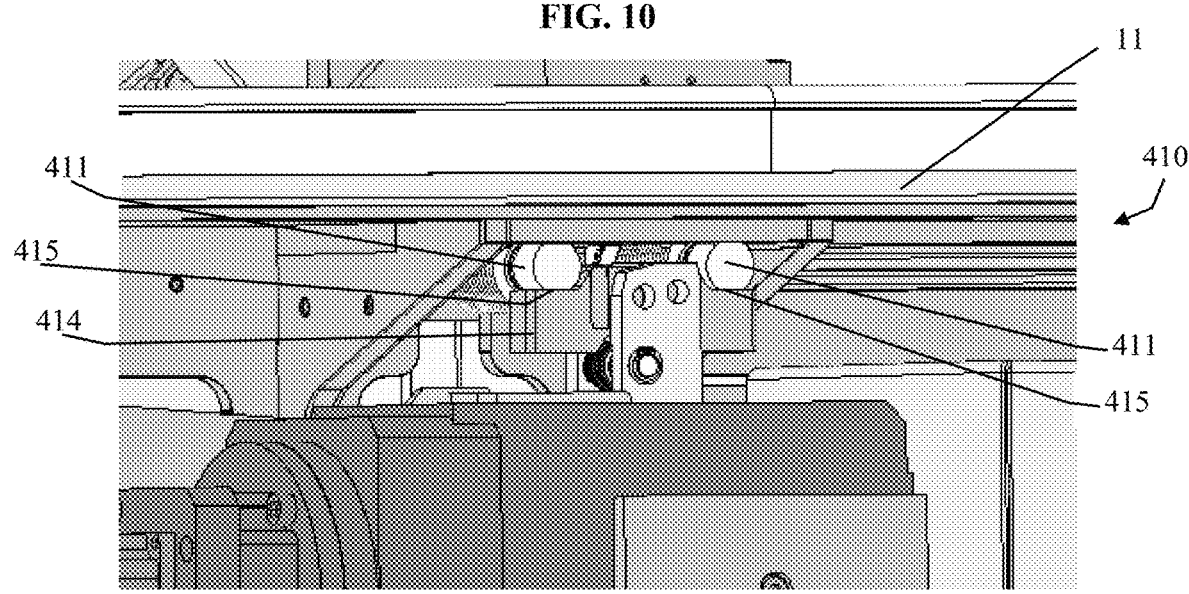
FIG. 11 is a partial perspective view of the weight sensing assembly.

With reference to FIGS. 10 and 11, the entire vertical load of the platform 11 and the configurable patient support 110 goes through and is detected by the load cells 411. Specifically, the load cells 411 are mounted between the platform 11 and the chain drive actuator 312. In other words, a first end 412 of the load cell 411 is coupled to the platform 11 and a second end 413 of the load cell 411 is coupled to the chain 313 of the chain drive actuator 312. The weight of the platform and positioning system and/or patient causes deflection of the load cells 411 and the strain in the load cells 411 is converted to an electrical output signal received by a processor, for example, to detect an amount of weight supported on the platform 11.

Figure 12:
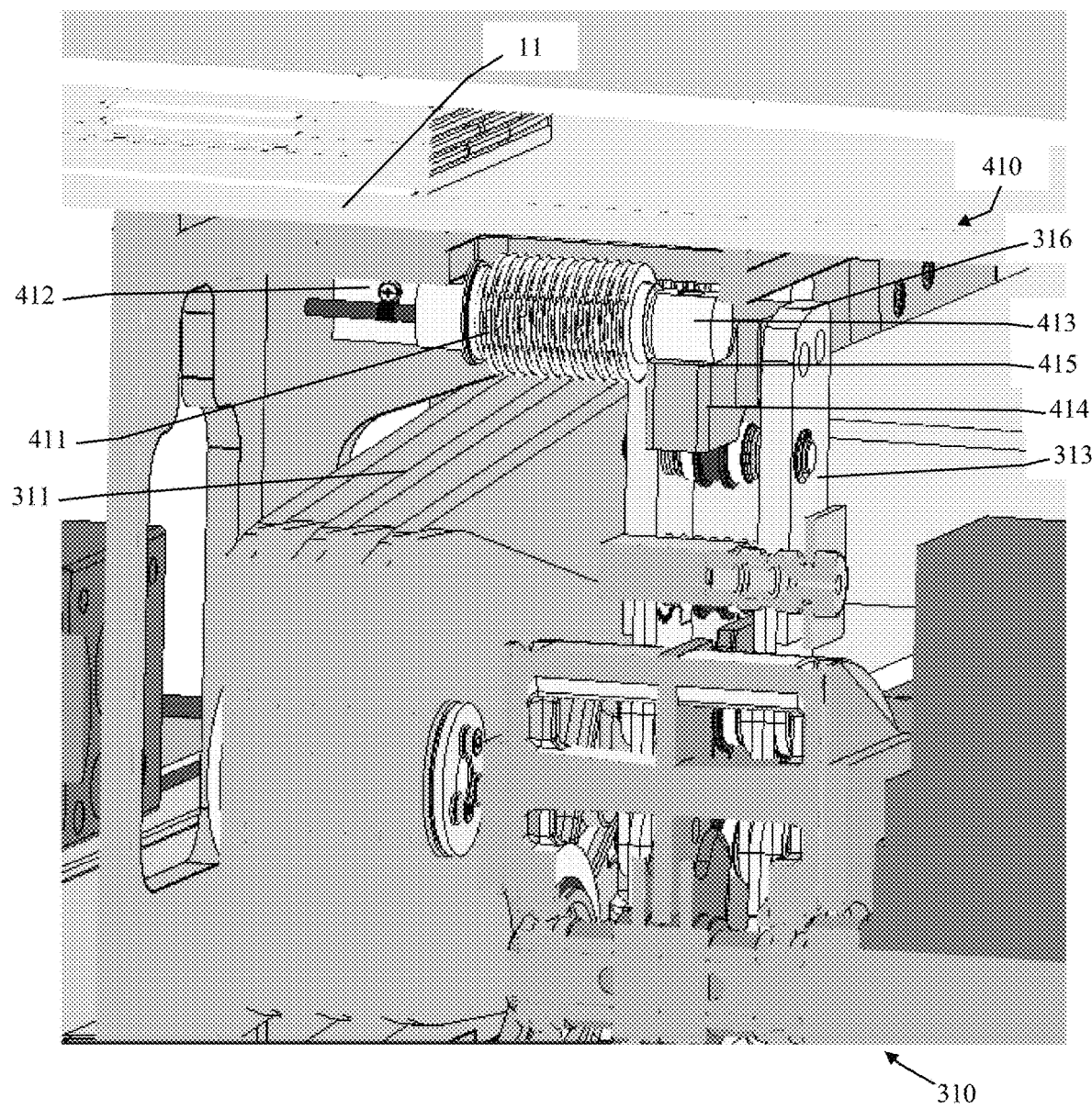
FIG. 12 is a partial cross-sectional view of the weight sensing assembly.

With reference to FIGS. 11 and 12, a support member 414 is coupled to the end 316 of the chain 313 and the load cells 411 are positioned on the support member 414. In the illustrated embodiment, the support member 414 is oriented approximately perpendicularly (e.g., horizontally) to the chain 313 extension direction (e.g., vertically). A notch 415 formed in the support member 414 receives the second end 413 of the corresponding load cell 411. In the illustrated embodiment, each support member 414 includes two notches 415 to receive two load cells 411.

The patient positioning system 10 utilizes information detected by the load cells 411 for various applications. For example, the detected weight can be monitored with respect to the amount of weight, the position of the weight, whether the weight should be present or should not be present, and whether the weight is changing or moving.

In some embodiments, when moving the seat, footrest (e.g., heel stop), backrest, etc. into one of the various positions/configurations and when the components are applying a force to a patient to aid ingress, egress, etc., the information from the load cells 411 is used to determine the weight of the patient, which can then be utilized to determine the amount of force desired or needed to push or pull the patient (e.g., by the dynamic configurations to aid ingress or egress of the patient from the patient support).

Figure 13A:
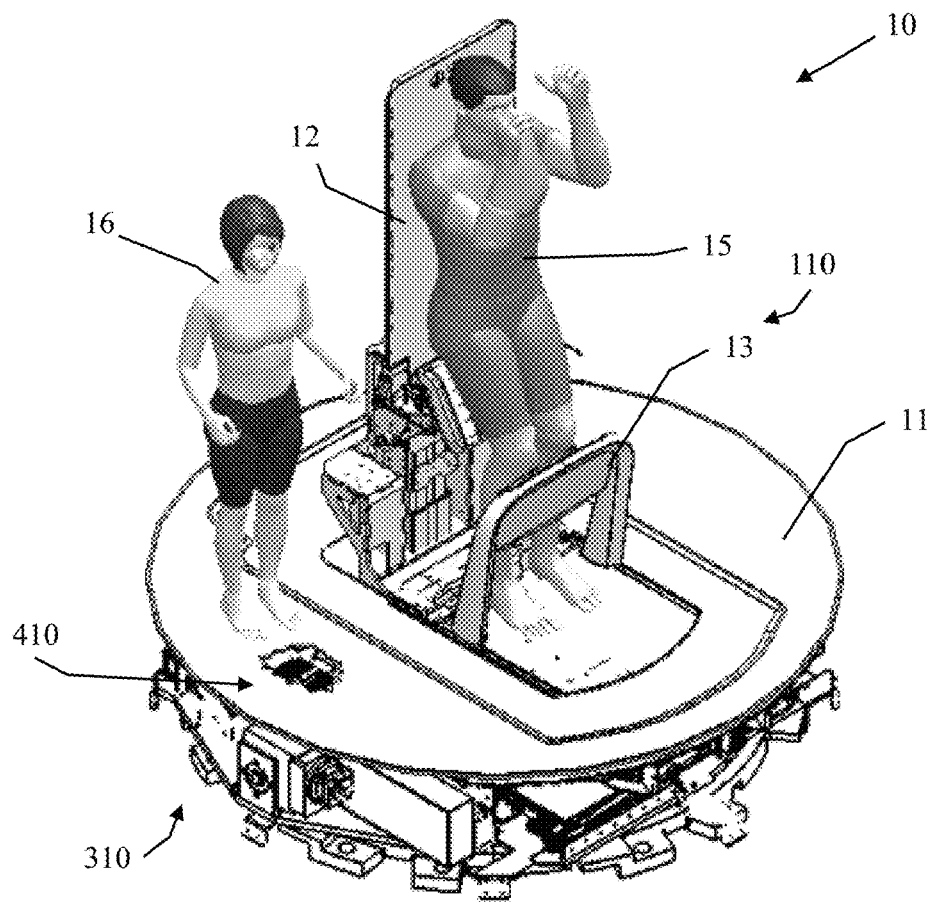
FIG. 13A is a perspective view of a scenario detected by the weight sensing assembly.
Figure 13B:
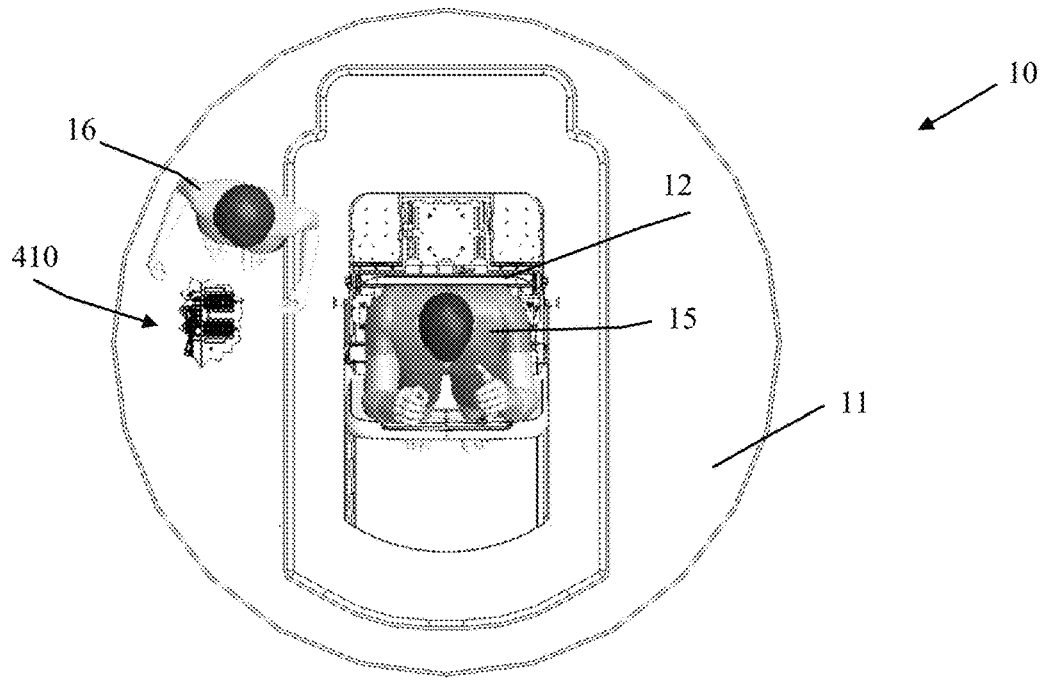
FIG. 13B is a top view of the scenario of FIG. 13A.

In some embodiments, the load cells 411 are used to determine the position and location of a patient and/or a technician. The location of the detected weight can be used to determine whether operation (e.g., energizing the beam, moving supports, translating and/or rotating the patient, etc.) is safe to occur. In other words, the output from the load cells 411 is monitored in some embodiments to provide a safety lockout and prevent operation if the detected weight is not consistent with an expected value of the weight. For example, if the weight of a technician 16 (FIGS. 13A and 13B) is detected on the platform 11, movement of the platform (e.g., movement in one or more of the six degrees-of-freedom axes of X, Y, Z, pitch, roll, and/or yaw) and/or energization of the imaging or treatment beam is locked-out until the technician is no longer detected on the platform. As another example, weight detected in a position other than on the patient support may indicate that an object is located on the platform and thus that the platform should not be moved until the object is removed.

In some embodiments, the load cells 411 are used to detect a sudden change in weight and/or weight distribution on the patient support and/or a sudden increase of weight on the platform in areas other than the patient support, which can be indicative of a patient falling over or out of the patient support system. Likewise, a sudden increase in weight detected by the load cells 411 can be indicative of a component of the patient support colliding with something during movement.

In some embodiments, the load cells 411 are used to detect a change in the position of a weight on the patient support during imaging, which can indicate that the patient has moved during imaging and that an image of the patient may have a reduced quality (e.g., with respect to an image of a patient who did not move). Detecting movement of the patient may indicate that imaging should be repeated to acquire an image of adequate and/or improved quality.

In some embodiments, the load cells 411 are used to identify and/or confirm the identity of a patient using the patient weight and/or confirming if the detected weight is proper and/or expected. For example, a patient weight detected by the load cells is compared to an expected patient weight based on prior encounters and/or patient records and used, at least in part, to confirm the identity of the patient.

In some embodiments, the load cells 411 are used to compensate for flex in the platform, e.g., a mass on one side of the platform may be compensated by activating an actuator as described herein (e.g., 1, 2, or 3 actuators in the three-actuator embodiments; e.g., 1 or 2 actuators in the two-actuator embodiments) to move the platform to compensate for the mass.

Seat Tilt Axis

Figure 14:
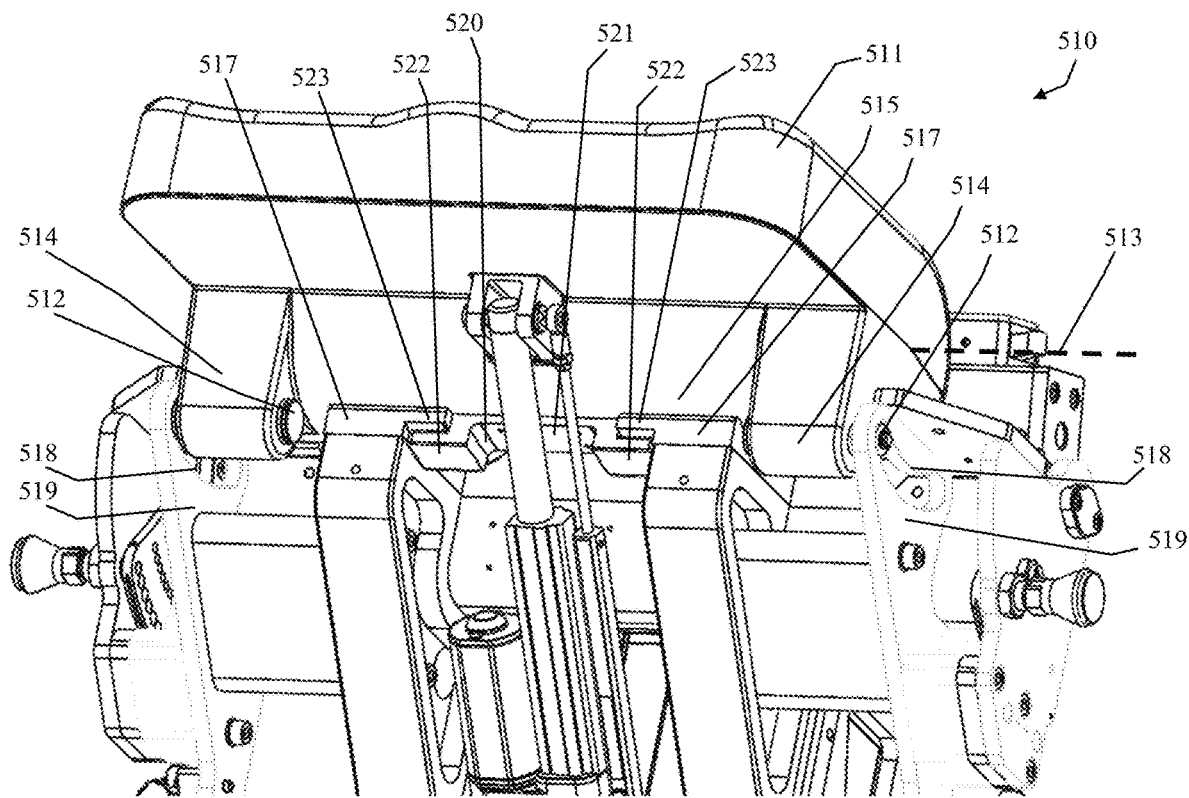
FIG. 14 is a partial perspective view of an adjustable seat assembly including a seat member.

With reference to FIG. 14, the configurable patient support 110 includes an adjustable seat assembly 510 including a seat member 511 with two offset rods 512. By this arrangement, the seat member 511 is positioned to extend outwardly from the back rest when the adjustable seat assembly 510 is in a first orientation to thereby offer support for a seated patient buttocks when that patient back is located against the back rest. Also by this arrangement, the seat member 511 is positioned downward (rotated about a rotational axis 513) to locate toward the same plane as the back rest and thus be positioned away from the patient received by the patient support assembly in a second position. Conventional adjustable seats include a large metallic axle aligned with the rotational axis of the seat and creates problems because the metallic axle is positioned near the imaging or therapy beam line. The adjustable seat assembly 510 does not include a metallic axle or shaft aligned with the rotational axis 513 of the seat member 511. In contrast, the rods 512 have axes 513 that are offset from the rotational axis 513 of the seat member 511.

Figure 15:
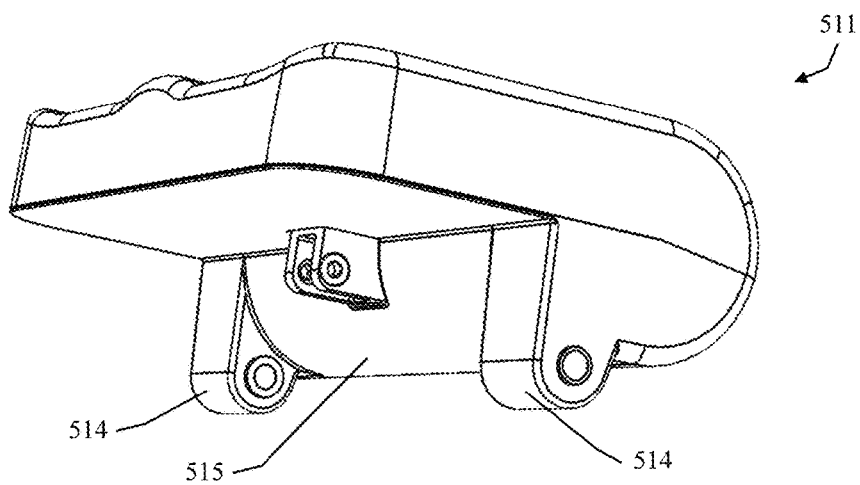
FIG. 15 is a perspective view of the seat member of FIG. 14.
Figure 17:
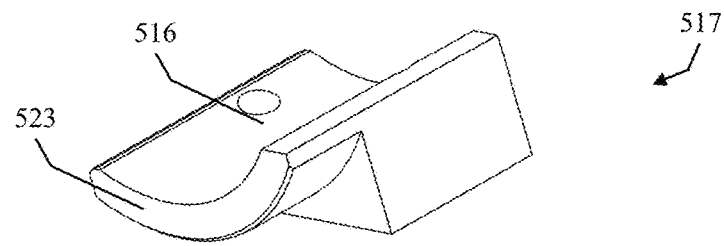
FIG. 17 is a perspective view of a mount of the adjustable seat assembly of FIG. 14.

With reference to FIGS. 14 and 15, the seat member 511 includes two lugs 514 that are configured to receive the offset rods 512. The seat member 511 includes an arcuate surface 515 that is slidably coupled to an arcuate surface 516 of two mounts 517 (FIG. 17). In some embodiments, the seat member 511 is P-shaped. In the illustrated embodiment, the arcuate surface 515 of the seat member 511 is positioned between the two lugs 514.

With reference to FIG. 14, a portion of the rods 512 is received within an arcuate slot 518 formed in a frame member 519. As the seat member 511 rotates about the rotational axis 513, the rods 512 translate within the slots 518 and the arcuate surface 515 slides relative to the mounts 517. In the illustrated embodiment, the rods 512 are offset from the rotational axis 513 of the seat member 511 in a first direction (e.g., Y-direction) and a second direction (e.g., Z-direction). As such, the seat member 511 is rotatable about the rotational axis 513 but does not include a metallic axle along the rotational axis 513 where it would interfere with the beam.

Figure 16:
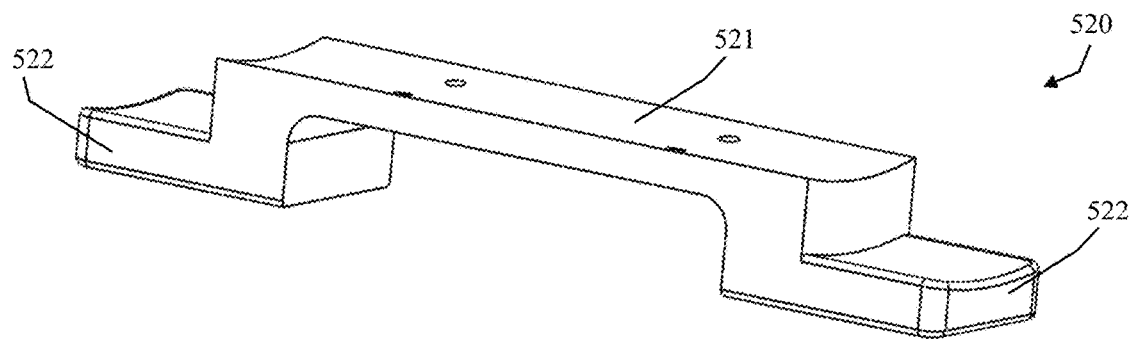
FIG. 16 is a perspective view of a cleat of the adjustable seat assembly of FIG. 14.

With continued reference to FIG. 14, the adjustable seat assembly 510 includes a cleat 520 coupled to the seat member 511 and is configured to constrain and/or prevent vertical movement of the seat member 511 as the seat member 511 moves between positions. With reference to FIG. 16, the cleat 520 includes a center portion 521 that is coupled to the arcuate surface 515 of the seat member 511. The cleat 520 also includes two wings 522 (arms) that are configured to be received below corresponding flanges 523 formed on the mounts 517. In other words, the wings 522 of the cleat 520 engage the flanges 523 of the mounts 517 to restrict the vertical movement of the seat member 511.

Figure 18:
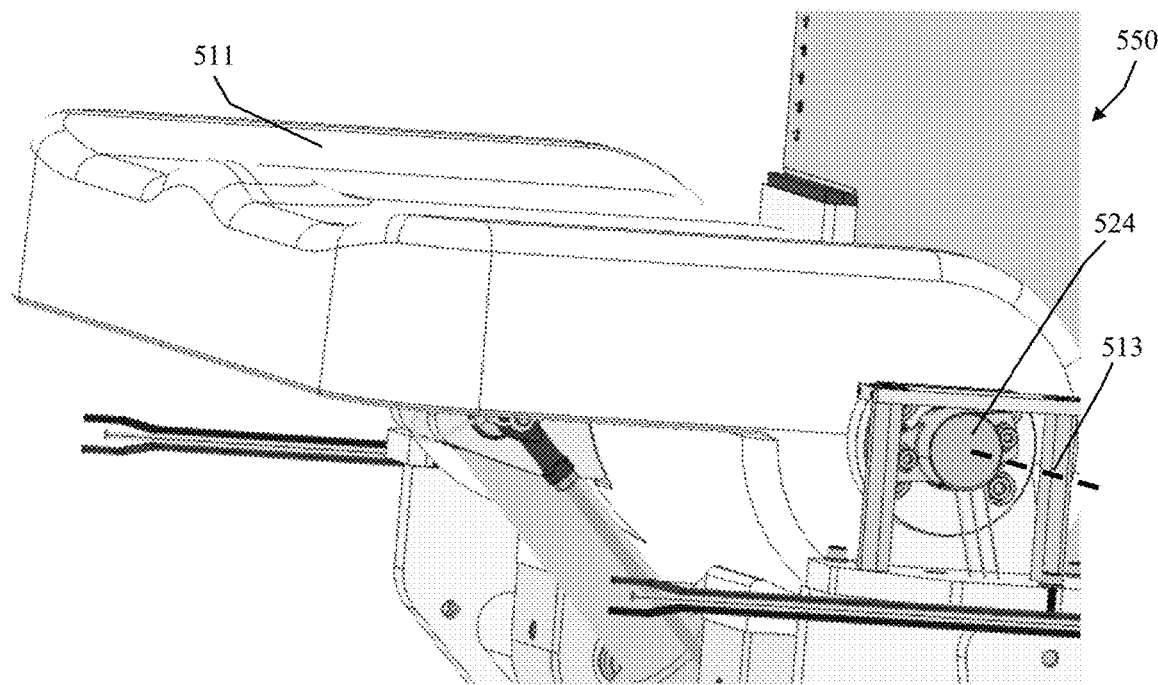
FIG. 18 is a partial perspective view of an adjustable seat assembly according to another embodiment.

With reference to FIG. 18, an adjustable seat assembly 550 according to another embodiment includes a seat member 511 that rotates about an axis 513 and a non-metallic axle 524 aligned with the rotational axis 513. In other words, the conventional metallic axle is replaced with a non-metallic axle 524 aligned with the rotational axis 513 of the seat member 511 such that the non-metallic axle 524 does not interfere with the imaging or treatment beam. In some embodiments, the non-metallic axle is made of a polymer or fiberglass (e.g., G-10).

Installation Leveling Adjustment

During installation, it is important that a rotational axis of the patient positioning system is aligned with the beam axis. When the axes are projected over large distances with uneven surface, the alignment becomes difficult. In some embodiments, the beam defines the origin of the coordinate system and alignment of the patient positioning system with the beam and/or beam coordinate system is important. Conventional patient positioning systems are not rotated or moved during treatment delivery and therefore no adjustment of the conventional system is required.

In some embodiments, the patient positioning system disclosed herein does not use a gantry and therefore precise alignment to the beam isocenter is desired. For example, patient positioning systems where the patient is able to walk on to the patient positioning system results in a large projection to the isocenter (e.g., approximately 148 cm).

In some embodiments, a plurality of adjusters 610 is utilized to level the patient positioning system 10 during installation. The adjustors 610 each have an X, Y, and Z adjustment for leveling. For example, the adjustor 610 can be adjusted in the Z-direction and then radially adjusted to provide an X and/or Y direction adjustment. In some embodiments, the X and Y adjustment is independent from (does not affect) the Z adjustment. The adjustor 610 is a compact design that does not increase the pit depth. In some embodiments, adjustors 610 are positioned under a bearing of the patient positioning system 10 for 3-point axis adjustment.

Figure 20:
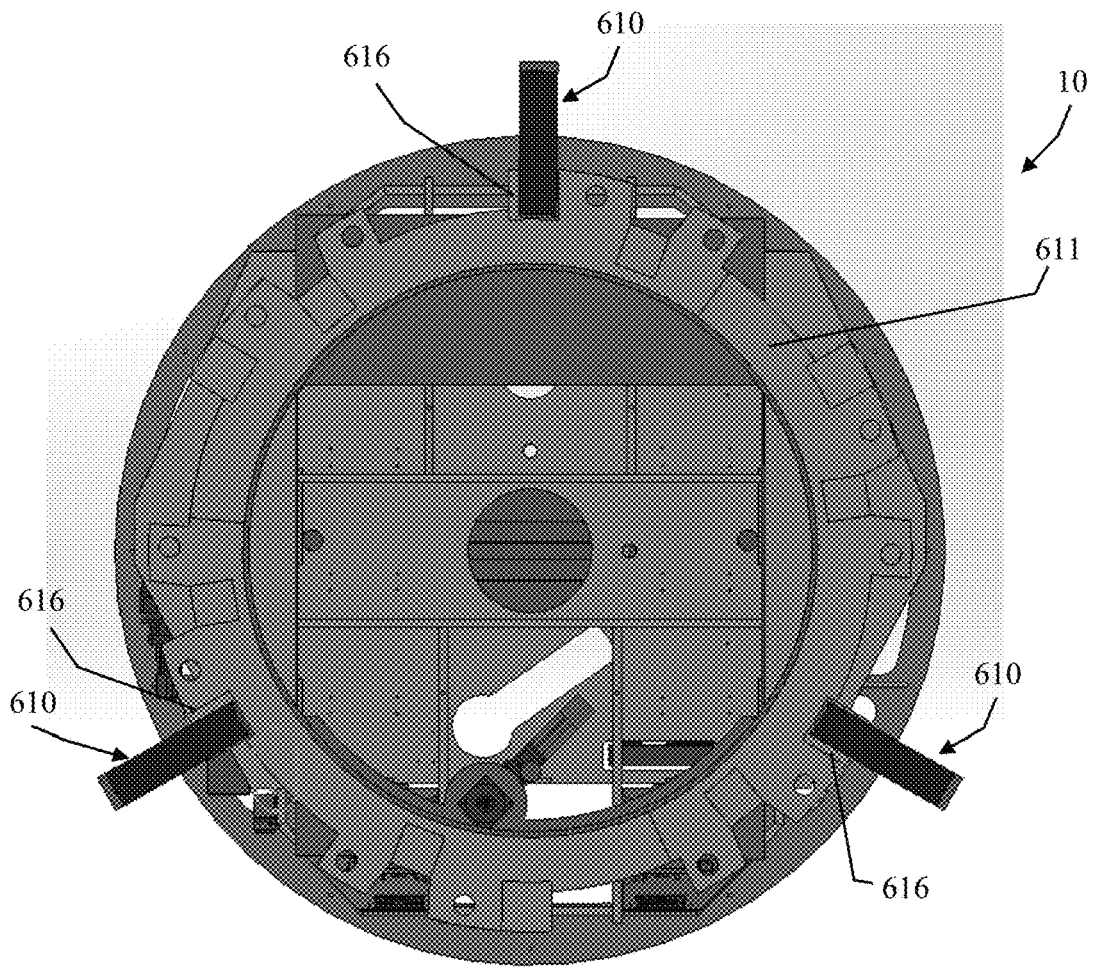
FIG. 20 is a bottom view of the patient positioning system of FIG. 1 with three adjustors for leveling and alignment.

With reference to FIG. 20, three adjustors 610 are coupled to a bottom 611 of the patient positioning system 10. In the illustrated embodiment, the adjustors 610 are equally spaced apart in a circumferential direction. In other words, the three adjustors 610 are spaced approximately 120 degrees apart. In the illustrated embodiment, the adjustors 610 are positioned in a pit between the patient positioning system 10 and a bottom of the pit.

Figure 19:
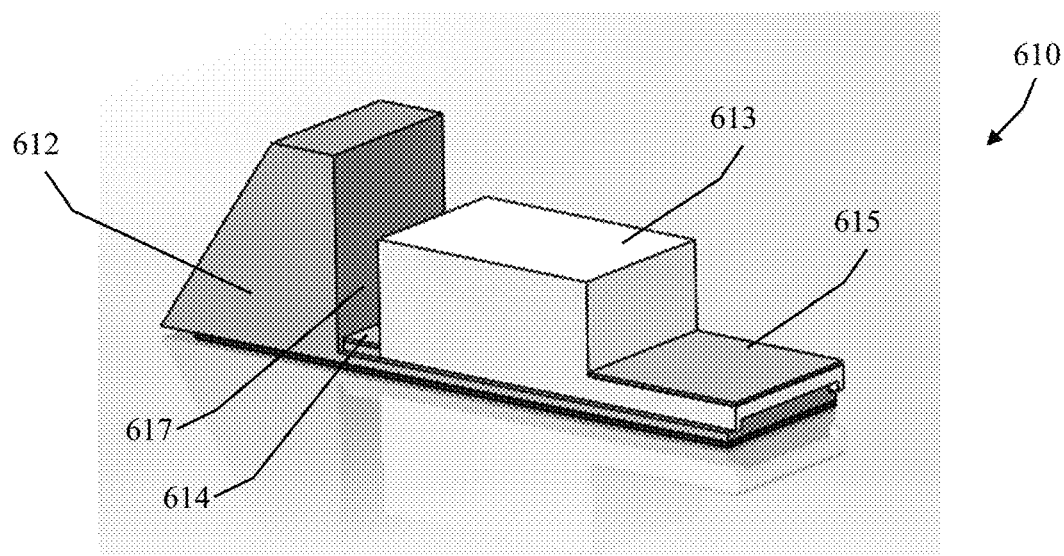
FIG. 19 is a perspective view of an adjustor.

With reference to FIG. 19, the adjustor 610 includes a first block 612 and a second block 613 movable with respect to the first block 612. The adjustor 610 includes a first low friction sheet 614 positioned between the first block 612 and the second block 613, and a second low friction sheet 615 positioned on the second block 613. In some embodiments, the low friction sheets 614, 615 are a low friction IGUS sheet material (e.g., as provided commercially at igus.com; an exemplary material is IGLIDUR G). A portion 616 (FIG. 20) of the patient positioning system 10 is positioned on the second low friction sheet 615 on the second block 613. In some embodiments, the portion 616 is a portion of a bottom bearing.

With continued reference to FIG. 19, a groove 617 is defined between the first block 612 and the second block 613 and the groove 617 is configured to receive levelling wedges to adjust the position of the second block 613 relative to the first block 612. In response to levelling wedges being inserted into the groove 617, the second block 613 slides along the first low friction sheet 614 with respect to the first block 612.

During installation, the adjustors 610 are positioned within the pit to define a level plane in a vertical direction (e.g., Z-direction). Then, one adjustor 610 is moved to achieve the desired position in a first direction (e.g., X-direction) and the other two adjustors 610 are moved to achieve the desired position in the second direction (e.g., Y-direction). In some embodiments, the adjustors 610 achieve an adjustment range of approximately +/−2.5 mm (e.g., approximately 2 to 3 mm (e.g., 2.00, 2.05, 2.10, 2.15, 2.20, 2.25, 2.30, 2.35, 2.40, 2.45, 2.50, 2.55, 2.60, 2.65, 2.70, 2.75, 2.80, 2.85, 2.90, 2.95, or 3.00 mm))

Locking Patient Support Interface

Figure 23A:
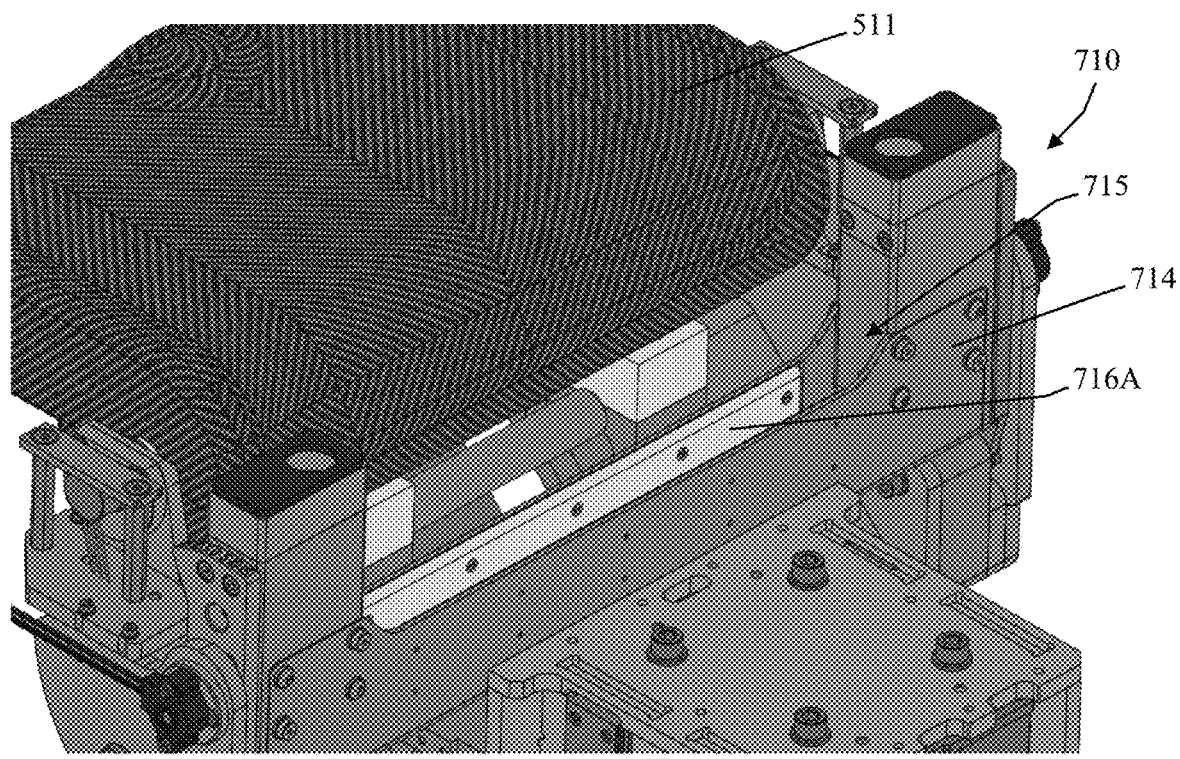
FIG. 23A is a colored perspective view of a base of a configurable patient support.
Figure 23B:
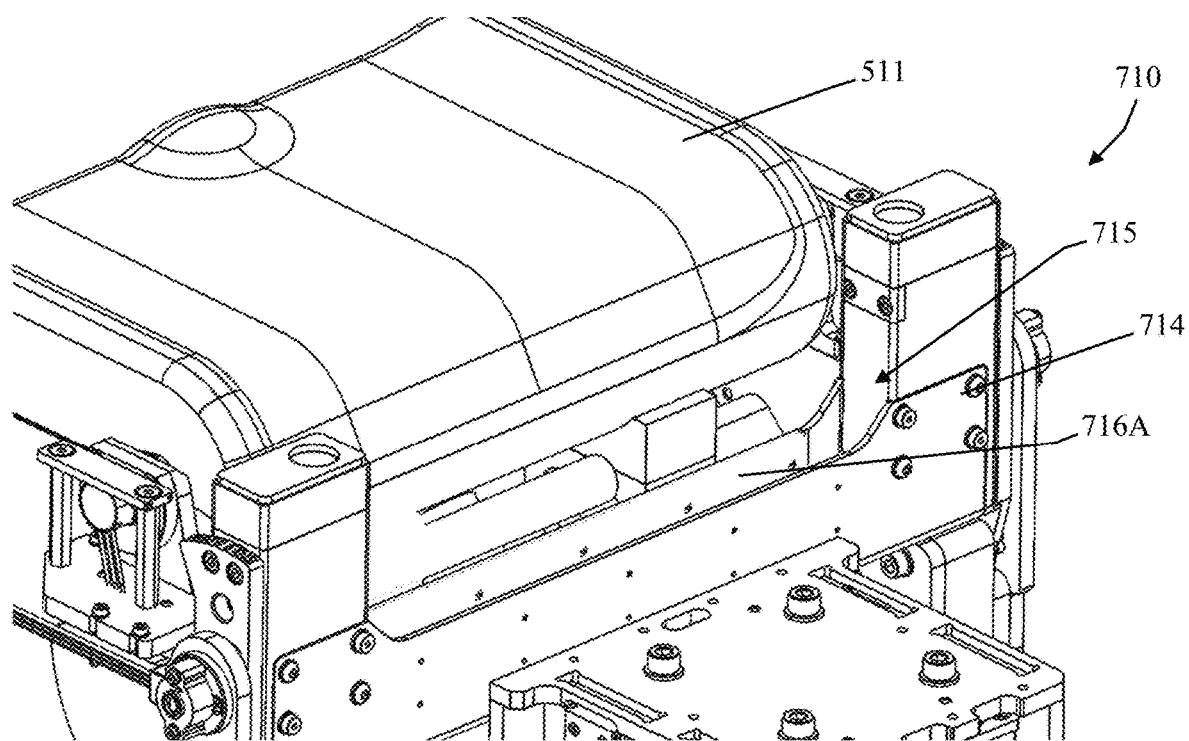
FIG. 23B is a black-and-white line drawing version of FIG. 23A.
Figure 24:
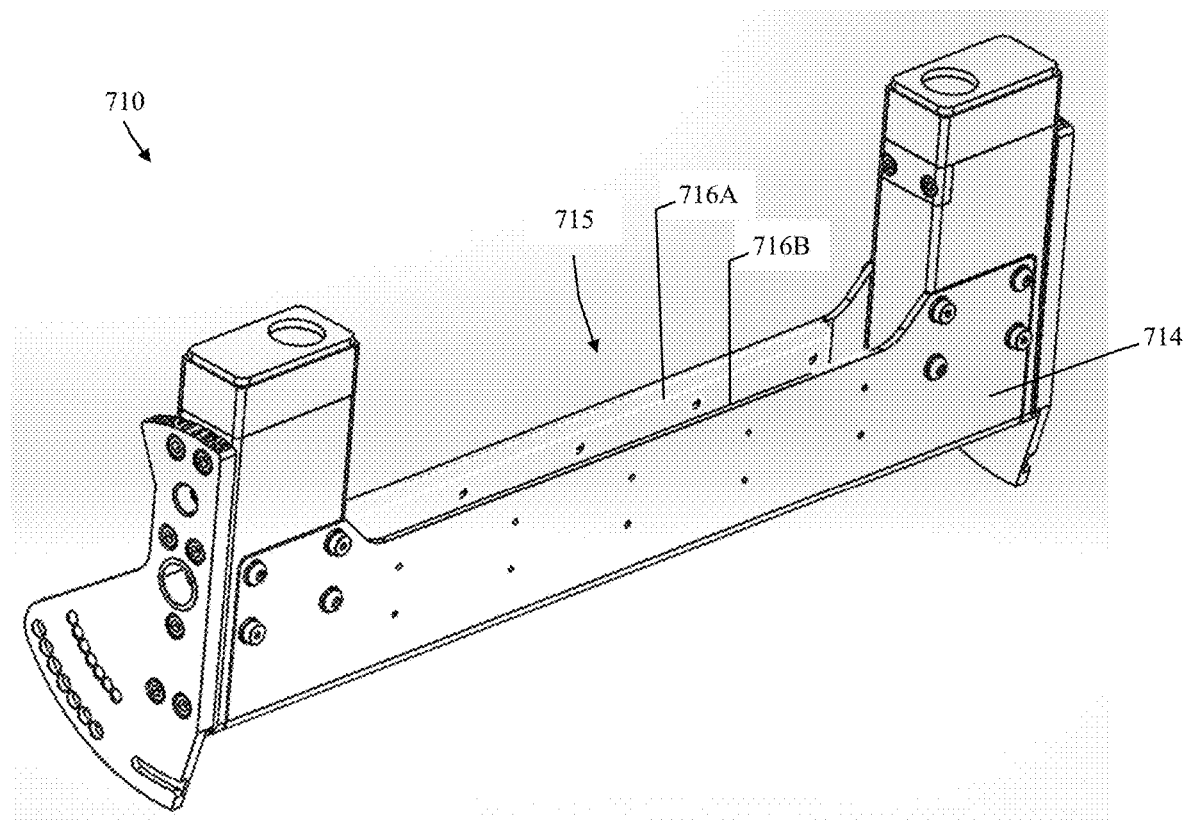
FIG. 24 is a partial perspective view of a portion of the base of FIG. 23A.

With reference to FIGS. 23A, 23B, and 24, a tilting and translating interface 710 for a patient positioning system 10 accepts modules of a backrest (for vertical sitting patients), a horizontal table (for prone/supine patients), and a smaller table (for QC purposes) (generically referred to as a support member). The interface 710 includes a base 714 with a receptacle 715 including a first low-friction pad 716A and a second low-friction pad 716B positioned within the receptacle 715. In the illustrated embodiment, the first pad 716A is positioned on a first side (front side) of the receptacle 715 and the second pad 716B is positioned on a second side (rear side), opposite the first side of the receptacle 715. In some embodiments, the first pad 716A and/or the section pad 716B are nylon.

Figure 21:
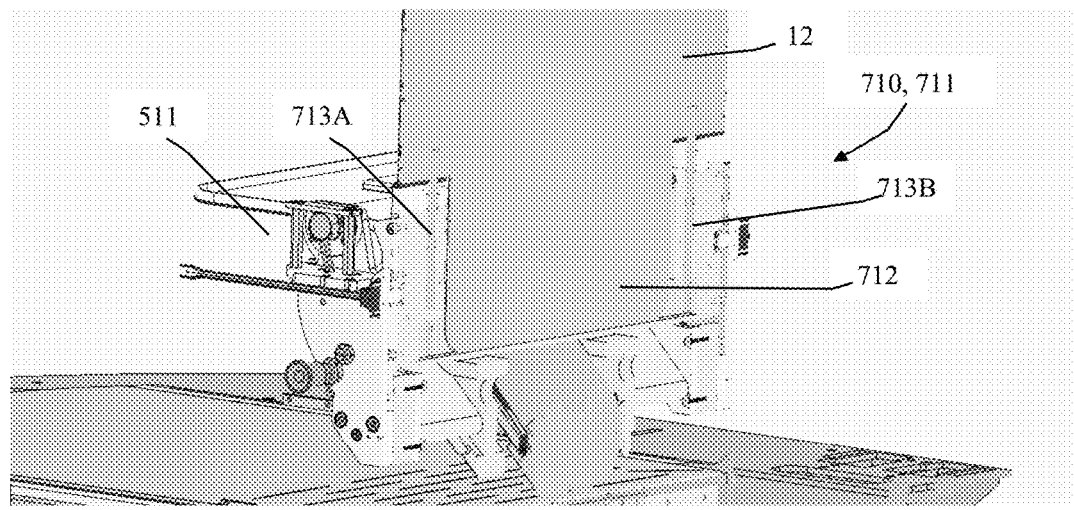
FIG. 21 is a partial perspective cross-sectional view of a configurable patient support.
Figure 22:
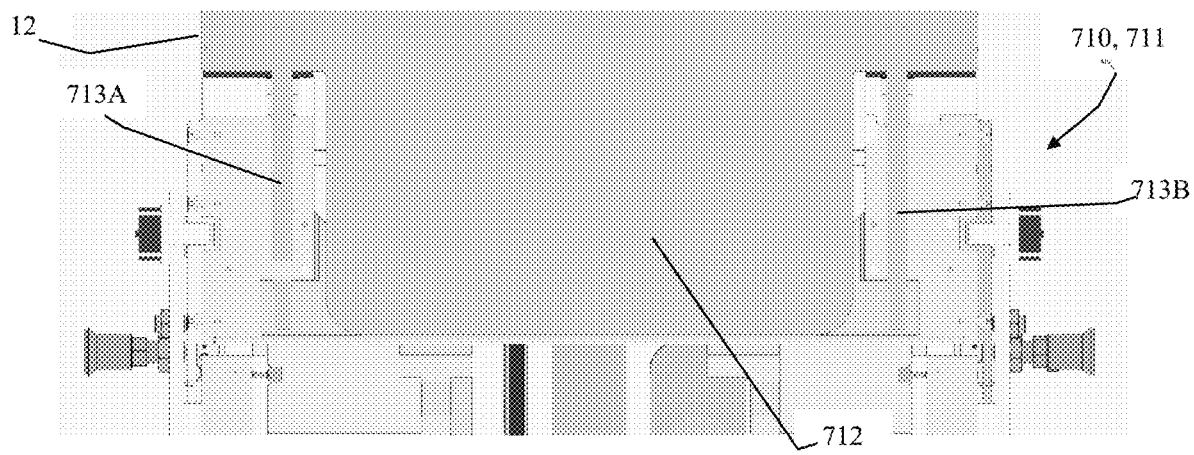
FIG. 22 is a partial cross-sectional view of a removable seat back including a tongue and two alignment rods.

With reference to FIGS. 21 and 22, in the illustrated embodiment, the support member (e.g., the backrest 12) includes a mechanical tongue and rod interface 711 that corresponds to the interface 710. The tongue and rod interface 711 ensures that the backrest 12 (or any other module components) is inserted fully and correctly with respect to the base 714. For alignment purposes, it is important that any interface does not permit movement of an installed backrest, while still accommodating for manufacturing and assembly tolerances.

The embodiment disclosed herein includes the tongue and rod interface 711 with two means of support: a tongue 712 and two rods 713A, 713B. As discussed herein, the disclosed module backrest is interchangeable with the interface 710 by a layperson user, is repeatable, and does not flex when installed.

Similar to the receptacle 715, the tongue 712 includes at least one low-friction (e.g., nylon) pad 717A-717D. In the illustrated embodiment, the tongue 712 includes four pads 717A-717D, with one on each side of the tongue 712. In some embodiments, the low-friction pads 717A-717D are nylon. The tongue 712 is removably received within the receptacle 715 to couple the support member (e.g., backrest, table top, etc.) with the base 714. The pads 717A-717D on the tongue 712 directly engage the pads 716A-716B in the receptacle 715 when the tongue 712 is received within the receptacle 715. A precision fit between the low-friction pads 716A-B and pads 717A-717D makes insertion easy while still maintaining low flex.

Figure 25:
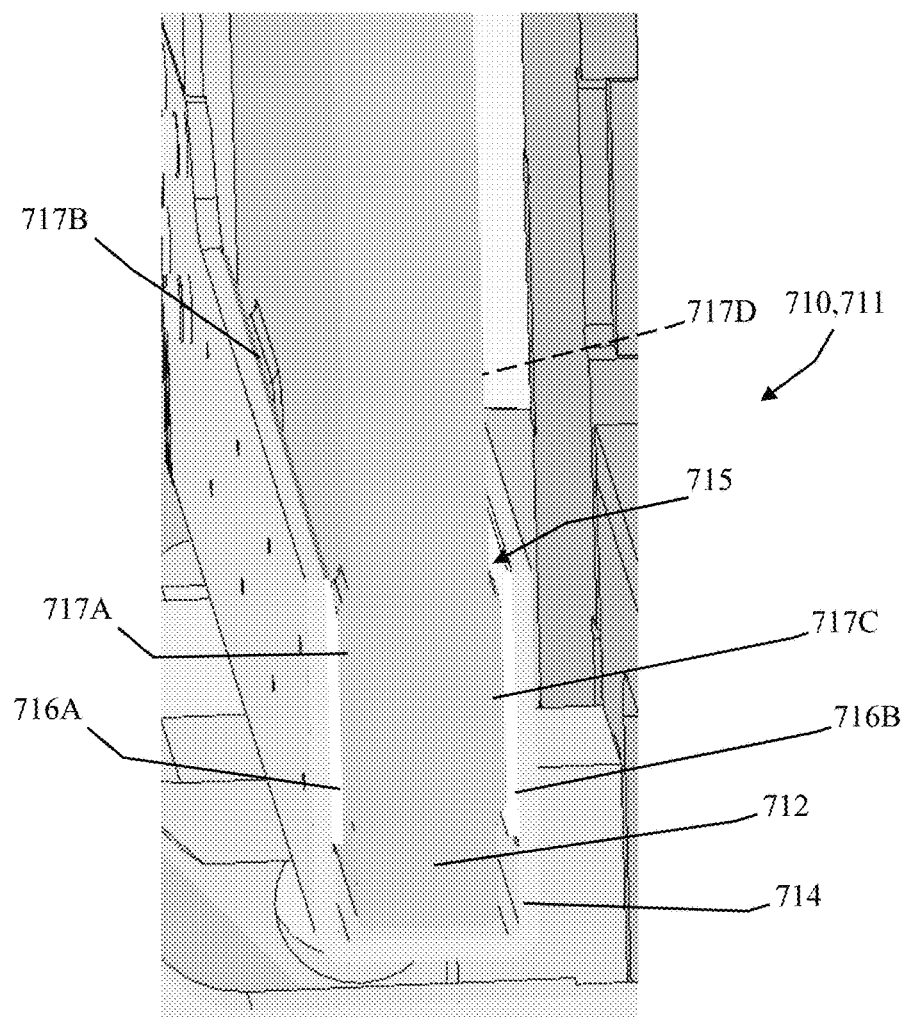
FIG. 25 is a partial perspective cross-sectional view of the removable seat back of FIG. 22.
Figure 26:
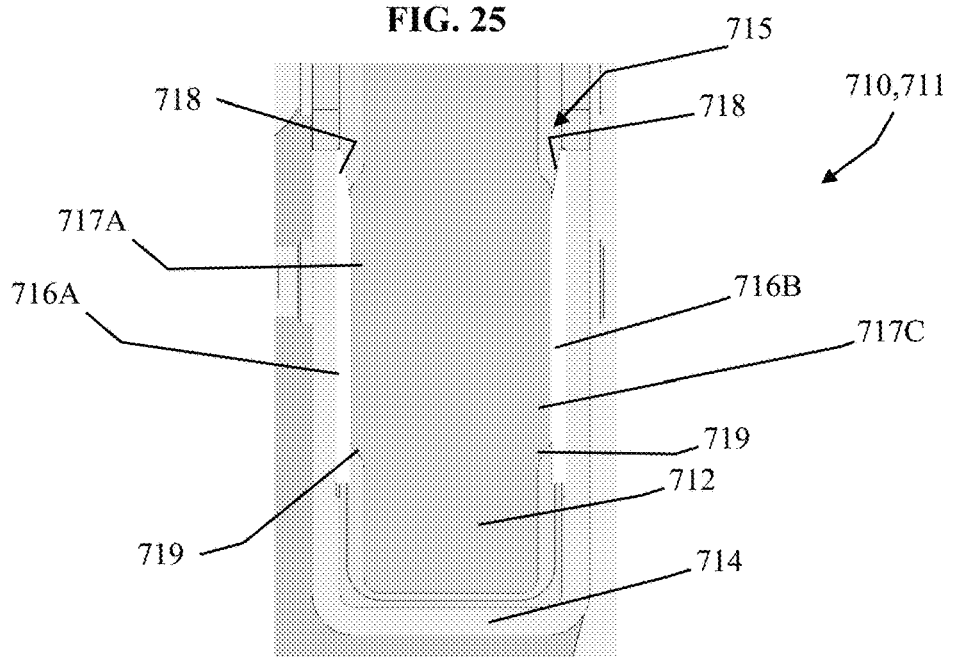
FIG. 26 is a cross-sectional view of the removable seat back of FIG. 25.

With reference to FIGS. 25 and 26, the pads 716A-716B in the receptacle 715 include a leading beveled edge 718 and the pads 717A-717D on the tongue 712 include a corresponding leading beveled edge 719. The corresponding beveled edges 718, 719 assist with proper alignment of the tongue 712 as it is inserted within the receptacle 715.

Figure 27:
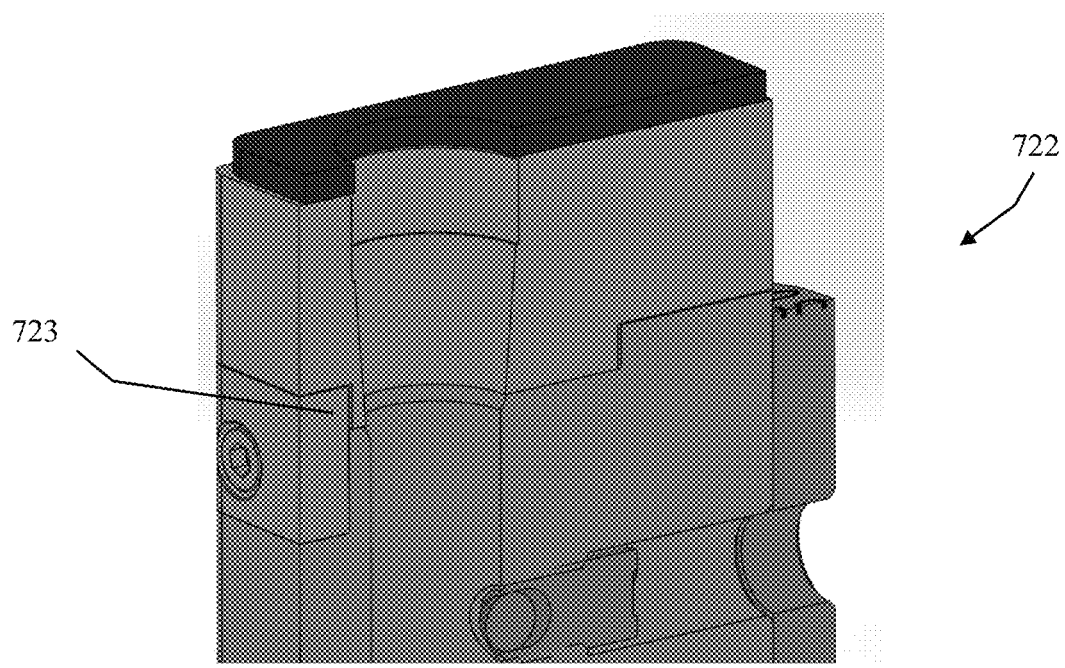
FIG. 27 is a partial cross-sectional view of a first rod block.
Figure 28:
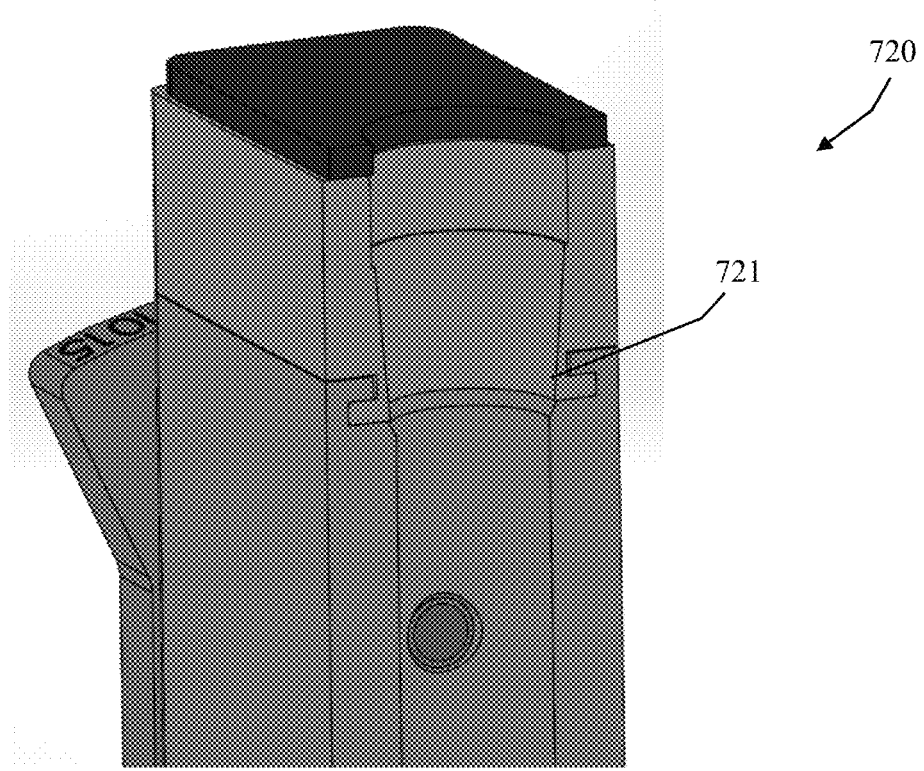
FIG. 28 is a partial cross-sectional view of a second rod block.

With reference to FIG. 22, the tongue 712 is positioned between the first rod 713A and the second rod 713B. In the illustrated embodiment, the rods 713A, 713B extend in a direction parallel to the tongue 712. The interface 710 further includes a first block 720 (FIG. 28) with a first bore 721 and a second block 722 (FIG. 27) with a second bore 723. When the tongue 712 is received within the receptacle 715, the first rod 713A is received within the first bore 721 of the first block 720 and the second rod 713B is received within the second bore 723 of the second block 722.

In some embodiments, each block 720, 722 constrains the corresponding rod 713A, 713B (and ultimately the backrest 12) in one of the X-direction or the Y-direction. In other words, the first block 720 permits adjustment in a first direction (an X-direction), and the second block 722 permits adjustment in a second direction (a Y-direction) orthogonal to the first direction. In other embodiments, any one of the blocks 720, 722 can constrain both the X-direction and the Y-direction of the backrest position.

In some embodiments, the first block 720 or 722 comprises a precisely dimensioned hole configured to accept a corresponding rod 713A or rod 713B; and the second block 720 or 722 comprises a precisely dimensioned hole configured to accept a corresponding rod 713A or rod 713B and the second block 720 or 722 is configured to freely move (e.g., slide) toward and away from the first block 720 or 722 to accommodate a width between the two rods 713A and 713B of the backrest that is imprecisely matched to a width between the holes in the blocks 720 and 722. Thus, in some embodiments, the first block is fixed and the second block may slide toward and away from the first block 720 or 722 to match the width of the rods of the back rest.

Figure 29:
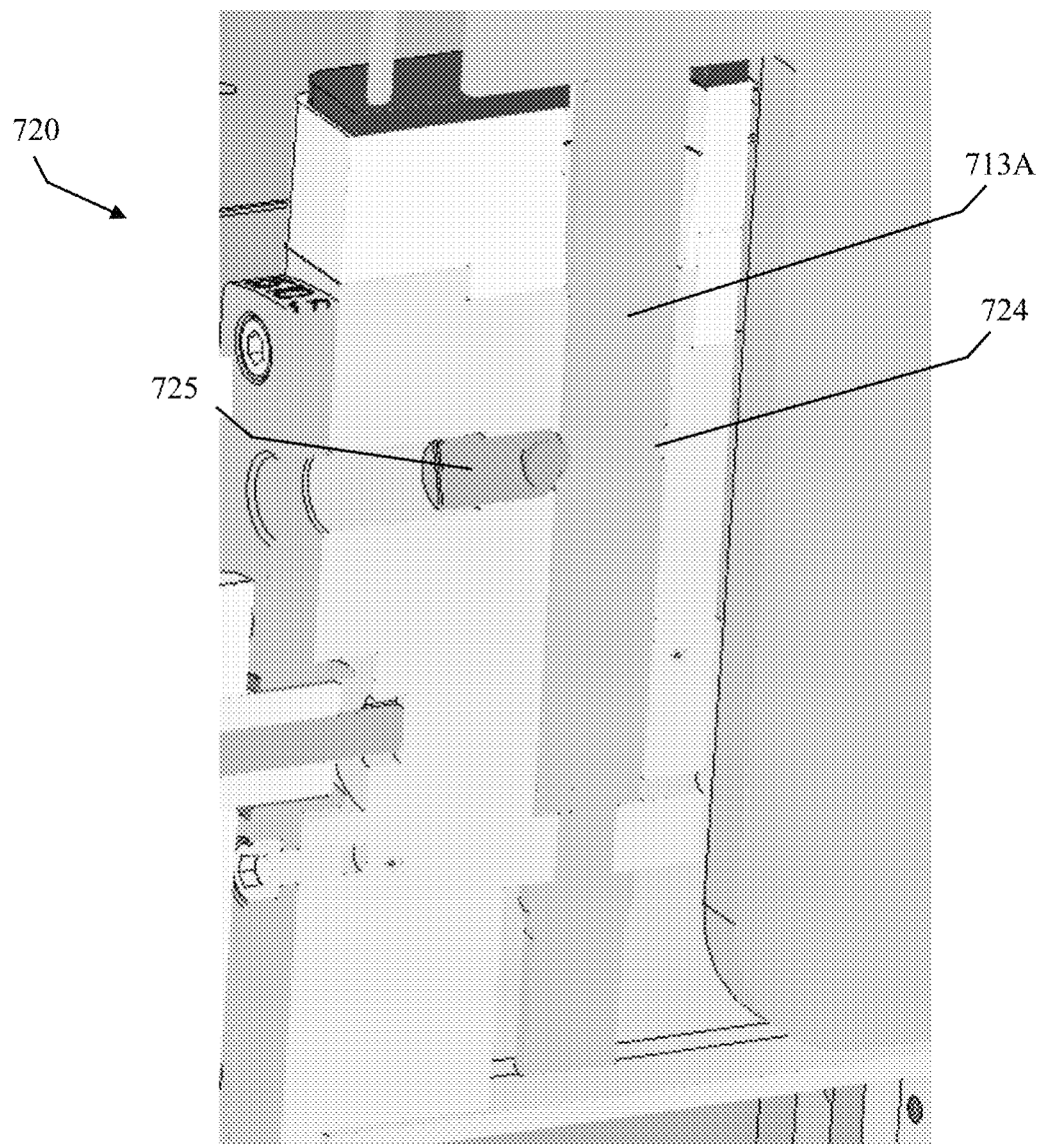
FIG. 29 is a partial cross-sectional view of a rod positioned within a block.

With reference to FIG. 29, in some embodiments, the rods 713A, 713B each include a circumferential groove 724 positioned around an exterior. A corresponding ball detent 725 extends at least partially within the bore and is received within the groove 724. In other words, the ball detent 725 and groove 724 create a Z-direction set point for the backrest 12.

In some embodiments a switch (e.g., a microswitch) is positioned at a bottom of the bores 721, 723. In some embodiments, more than one switch is included. In some embodiments, when the rod is positioned fully within the bore, the switch is mechanically actuated and the switch output provides an assurance that the seat rest is installed, fully installed, and/or properly installed.

In some embodiments, an indexing nob or resistor uniquely identifies each accessory. Conventional tabletops and accessories rely on an operator to ensure the correct part has been fitted and installed correctly. The indexing nob or resistor enables confirmation that the operator has installed the correct accessory, thereby mitigating operator error. In some embodiments, automatic execution or preparation of certain workflows may results from the installation of a certain accessory.

Vac-Bag

Figure 30:
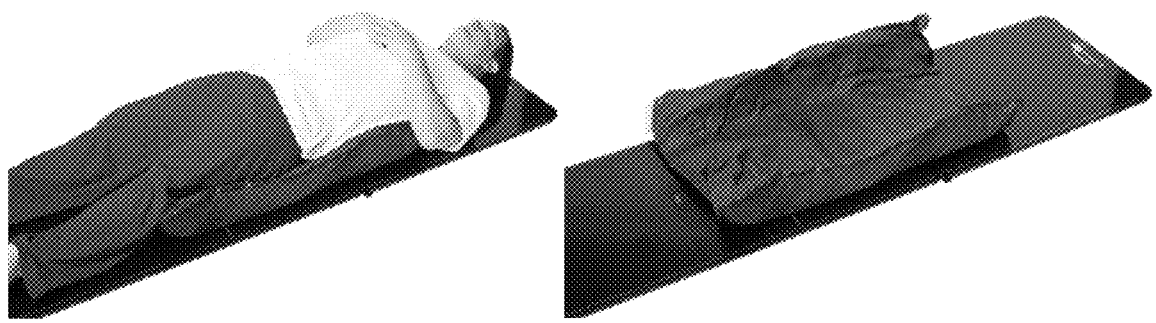
FIG. 30 is an illustration of a conventional conformable patient support.

With reference to FIG. 30, conventional vac-bags are used for seat, backrest, and arm rests. The conventional vac-bag is a bag containing "beans" (e.g., polymer (e.g., expanded polystyrene or the like) spheres as in a bean bag) and is squishy and malleable prior to evacuation. Anatomy is pressed into the vac-bag and is evacuated to lock the beans into place (e.g., mold the vac-bag to a patient to provide a custom fit contour). A custom vac-bag can then be removed, stored, and utilized again at a later time. However, conventional vac-bags do not form well to a patient in a vertical orientation. Specifically, the beans settle to the bottom of the bag when the vac-bag is positioned vertically; consequently, the vac-bag is unable to create a contour in the upper-most portion of the bag.

Figure 31:
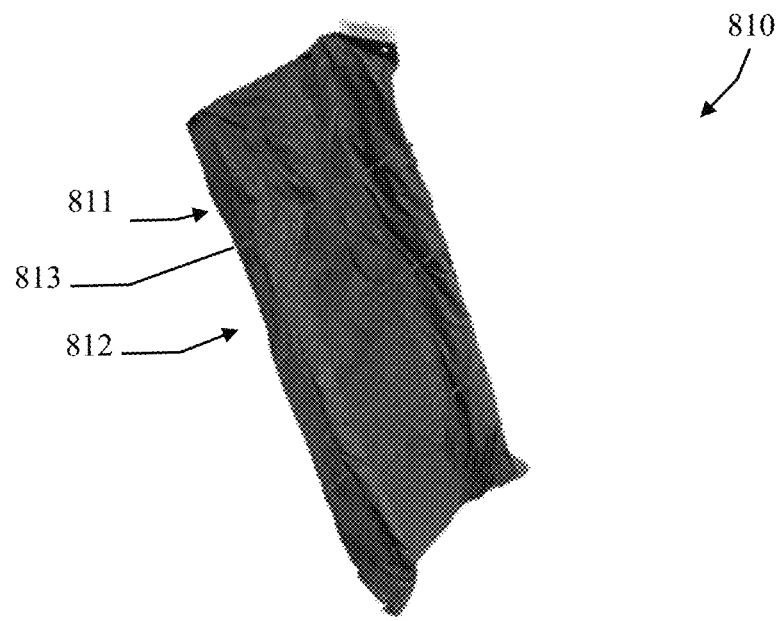
FIG. 31 is a perspective view of a vertical conformable patient support.

With reference to FIG. 31, a vertical conformable patient support 810 (e.g., vertical vac-bag) disclosed herein includes segmented compartments for the beans. In some embodiments, the conformable patient support includes an outer layer, an interior cavity including a first section 811, a second section 812, and a dividing member 813 positioned between the first section and the second section. A first plurality of beans is positioned within the first section 811 and a second plurality of beans is positioned within the second section 812. The first section is positioned above the second section when the conformable patient support is oriented to conform to a patient in an upright position.

A method of conforming a bag to a patient in an upright position disclosed herein includes evacuating a portion of the air within a bag containing a plurality of beans, orienting the bag vertically, pressing the bag against a patient in an upright position and evacuating a second portion of the air within the vac-bag. In other words, in some embodiments, vertical vac-bags disclosed herein include a partially evacuated bag prior to forming the patient contour. The partial evacuation helps keep the beans in a position suitable to take a patient contour when vertically oriented.

In some embodiments, personalized contoured vac-bags include a keyed interface (e.g., key and groove) to ensure correct repositioning of the vac-bag. For example, the bottom of the bag in some embodiments includes a key that is positioned within a corresponding notch formed on the seat.

Fluid Control Cassette

Figure 32:
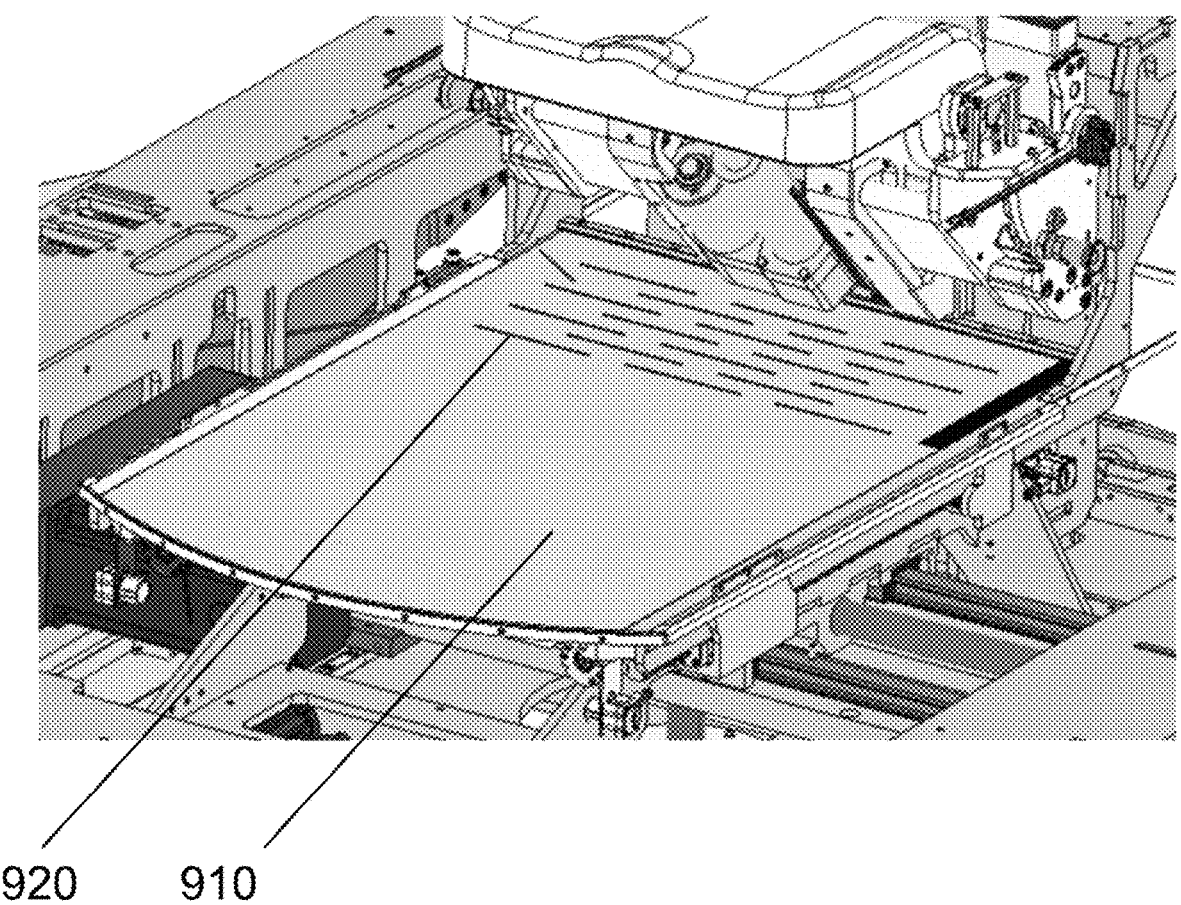
FIG. 32 is a perspective view of a floor panel.
Figure 33:
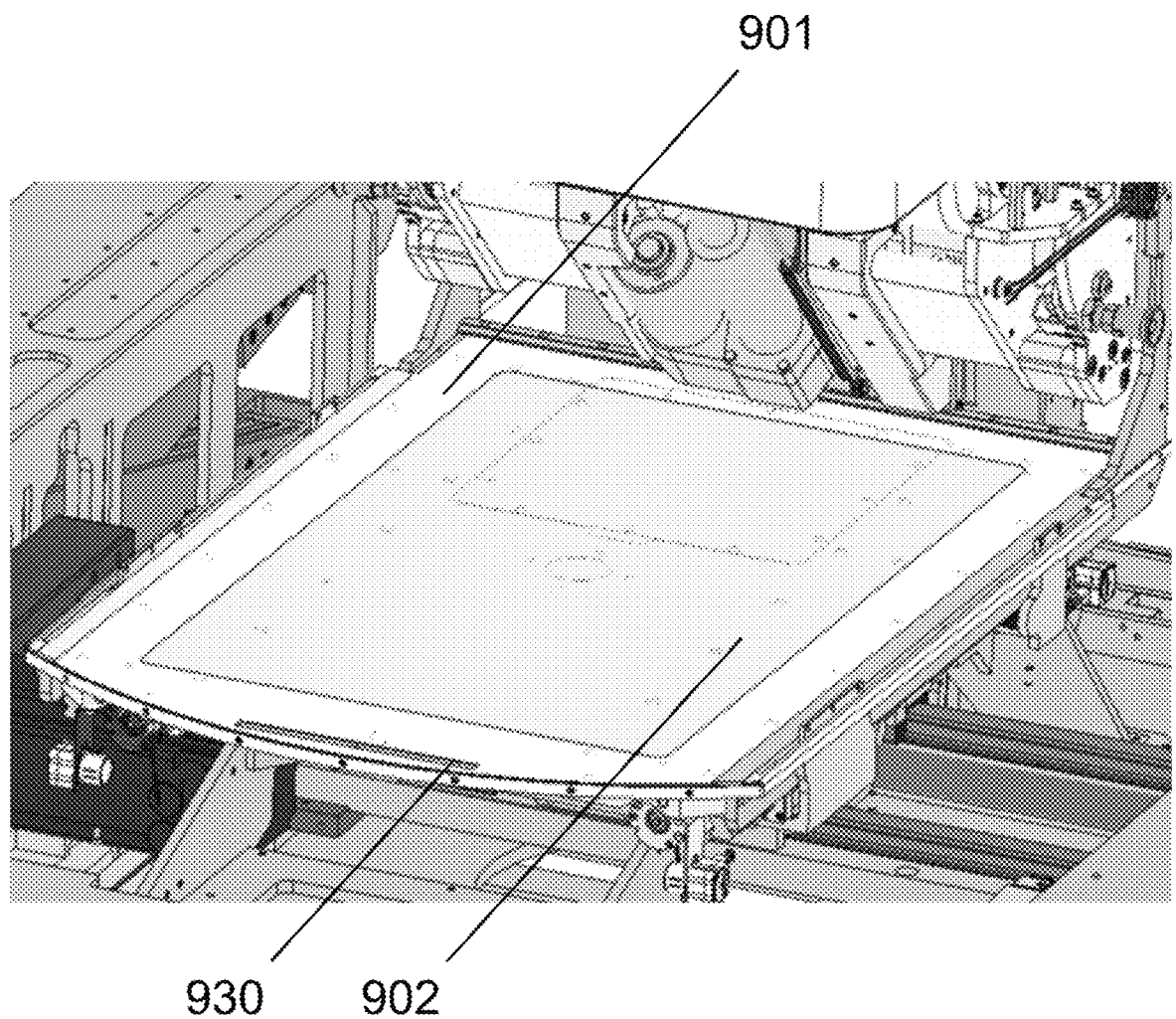
FIG. 33 is a perspective view of a removable fluid control cassette mounted in a floor panel.
Figure 34:
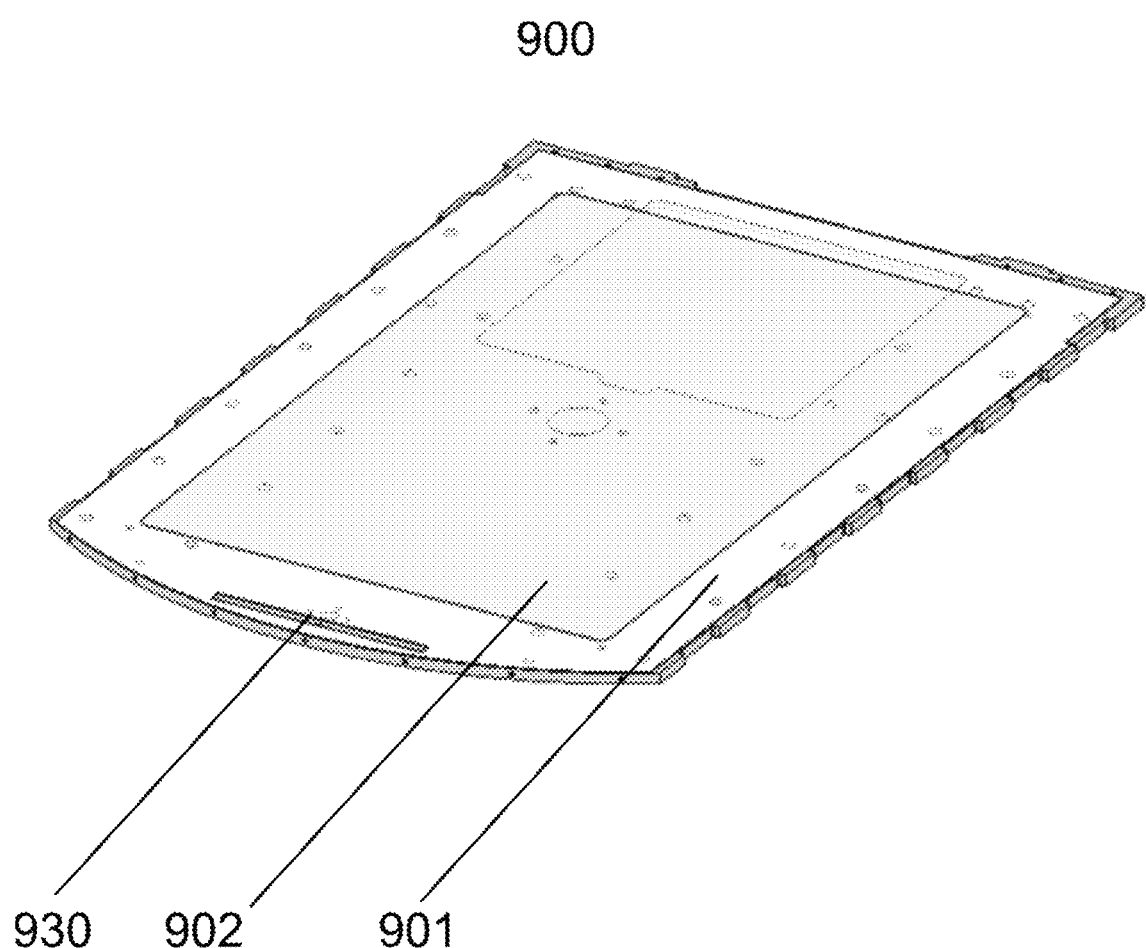
FIG. 34 is a perspective view of the removable fluid control cassette of FIG. 33.

In some embodiments, the patient positioning system 10 comprises a fluid control cassette 900 (FIGS. 32-34). In some embodiments, the rotating disc (e.g., below and supporting the patient support) comprises the fluid control cassette 900. In some embodiments, the patient positioning system 10 and/or the rotating disc comprises a floor panel 910 having a top surface and a bottom surface and the floor panel 910 comprises drainage holes 920 through which may flow a fluid contacting the top surface of the floor panel 910. In some embodiments, the floor panel 910 comprises a fluid control cassette receiving aperture structured to receive the fluid control cassette 900 and to removably couple the fluid control cassette 900 in a position below the floor panel 910. In some embodiments, the fluid control cassette 900 and the fluid control cassette receiving aperture are structured so that the fluid control cassette 900 may be inserted into the fluid control cassette receiving aperture by sliding the fluid control cassette 900 into the fluid control cassette receiving aperture. In some embodiments, the fluid control cassette receiving aperture comprises a first rail and a second rail that engage with a first edge and a second edge, respectively, of the fluid control cassette 900 to guide insertion of the fluid control cassette 900 into the fluid control cassette receiving aperture and to provide support for the inserted fluid control cassette 900.

When the fluid control cassette 900 is inserted into the fluid control cassette receiving aperture, the fluid control cassette 900 is positioned to contact a fluid that flows through the drainage holes 920 in the floor panel 910 and thus to control (e.g., absorb and retain) a fluid that flows through the drainage holes 920 in the floor panel 910. In some embodiments, the floor panel 910 comprises a fluid-resistant (e.g., hydrophobic) coating that promotes fluid shedding and fluid drainage through the drainage holes 920. In some embodiments, the floor panel 910 comprises grooves or other structural guidance features that guide fluid to, into, and through the drainage holes 920. In some embodiments, the floor panel 910 is sloped with respect to the horizontal to promote the movement of fluids toward and through the drainage holes 920.

In some embodiments, the fluid control cassette 900 and the fluid control cassette receiving aperture are structured so that the fluid control cassette 900 may be removed from the fluid control cassette receiving aperture by sliding the fluid control cassette 900 out of the fluid control cassette receiving aperture. After removal, the fluid control cassette 900 may be discarded, cleaned, and/or reused.

In some embodiments, the fluid control cassette comprises a handle 930 that facilitates insertion of the fluid control cassette 900 into the fluid control cassette receiving aperture by a user and/or that facilitates removal of the fluid control cassette 900 from the fluid control cassette receiving aperture by a user.

In some embodiments, the fluid control cassette 900 comprises a supporting plate 901 and an absorbent pad 902 (e.g., comprising an absorbent material). In some embodiments, the fluid control cassette 900 further comprises a peripheral sealing gasket (e.g., comprising a pliable and/or compressible material). In some embodiments, the peripheral sealing gasket seals the fluid control cassette 900 into the patient positioning system 10 and thus integrates the fluid control cassette 900 into the patient positioning system 10 for fluid control. In some embodiments, the peripheral sealing gasket minimizes and/or eliminates the flow of liquid away from the absorbent pad 902 and thus provides fluid containment. In some embodiments, the absorbent pad 902 comprises an antimicrobial compound, an antiviral compound, an antibacterial compound, a disinfectant, an anti-odor compound, and/or a superabsorbent polymer (SAP) (e.g., comprising a poly-acrylic acid sodium salt, a poly-acrylamide copolymer, an ethylene maleic anhydride copolymer, a cross-linked carboxymethylcellulose, a polyvinyl alcohol copolymer, a cross-linked polyethylene oxide, and/or a copolymer of polyacrylonitrile).

In some embodiments, the fluid control cassette 900 is integrated into the patient positioning system 10 (e.g., into the rotating disc). Accordingly, in some embodiments, the floor panel 910 is contacted by the patient (e.g., the patient is positioned with feet contacting the floor panel 910).

In some embodiments, the fluid control cassette 900 is a consumable fluid control cassette 900 that is removable by a person (e.g., a user (e.g., a technician, therapist, or cleaner)) operating the patient positioning assembly and replaceable (e.g., with another (e.g., dry, clean, and/or new) fluid control cassette 900) by a person (e.g., a user (e.g., a technician, therapist, or cleaner)) operating or cleaning the patient positioning system 10. In some embodiments, the fluid control cassette 900 is a washable and/or sterilizable fluid control cassette 900 that is removable by a person (e.g., a user (e.g., a technician, therapist, or cleaner)) operating or cleaning the patient positioning system 10, that is reusable (e.g., after washing and/or sterilizing the removed fluid control cassette 900), and that is replaceable by a person (e.g., a user (e.g., a technician, therapist, or cleaner)) operating or cleaning the patient positioning system 10.

Accordingly, the fluid control cassette 900 provides for the containment and/or absorption of fluid that contacts the rotating disc and/or floor panel 910, e.g., in cases where the patient positioned on the patient support assembly evacuates a bodily fluid (e.g., urine, vomit, diarrhea, etc.) while positioned on the patient support. The fluid control cassette 900 prevents and/or minimizes fluid from fouling the floor of the patient positioning system 10 (e.g., the rotating disc and/or floor panel 920). Furthermore, the fluid control cassette 900 prevents and/or minimizes fluid evacuated onto the rotating disc and/or floor panel 900 from contacting mechanical and/or electrical components under the patient support (e.g., under the rotating disc) and causing malfunction or nonfunction of the mechanical and/or electrical components and subsequent malfunction or nonfunctioning of the patient positioning system 10.

Emergency Patient Evacuation

In the event of a power loss, a need remains for patient egress. Conventional approaches use a conventional high voltage uninterrupted power source (UPS). The UPS maintains a high voltage in the system and may cause hazards (e.g., in view of water damage) and relies on operational control electronics. Conventional alternatives include a manual crank (e.g., a hand crank) to facilitate removal of the patient. Conventional mechanical or manual solutions are cumbersome and time consuming.

The emergency patient evacuation system disclosed herein includes a low voltage battery electrically coupled with at least one relay to electrically power the actuators and brakes required for assisting evacuation of the patient. The disclosed design reduces the risk by eliminating high voltage and improves robustness because no working electronics are required.

In some embodiments, potential energy of the platform is used to activate the electronics of the patient evacuation system (e.g., using a dynamo or the like), e.g., by initiating a controlled descent of the platform that converts the kinetic energy of platform descent into electrical potential (e.g., energy) that finds use in powering components of the patient support to move them out of the way to allow safe patient egress. In some embodiments, the potential energy of the platform (e.g., converted to kinetic energy and therefrom to electrical potential) and a low voltage battery both find use in powering the emergency patient evacuation system.

In some embodiments, axes that need a controlled release after power loss (e.g., vertically lowering the platform) electrically connect braking resistors across motor terminals to control the velocity of the platform lowering.

In some embodiments, the configurable patient support 110 is configured to provide a dynamic configuration that assists emergency egress of a patient from the patient support, e.g., by providing support for the patient and/or by applying a force to the patient to guide, push, or pull the patient out of the patient support and/or away from the patient positioning assembly in case of power loss or other emergency. For example, in some embodiments, the configurable patient support is configured to contact the patient, operatively engage the patient, and apply a force to at least a portion of the patient (e.g., an arm, a leg, a torso, a head, a foot, a hand, a buttocks, a knee, an elbow) to facilitate emergency egress out of the patient support and/or away from the patient positioning assembly in case of power loss and/or other emergency. In some embodiments, one or more of the back rest, the head rest, the arm rest, the seat member, the shin rest, and/or the foot brace (e.g., heel stop) contacts the patient, operatively engages the patient, and applies a force to at least a portion of the patient (e.g., an arm, a leg, a torso, a head, a foot, a hand, a buttocks, a knee, an elbow) to facilitate emergency egress of the patient out of the patient support and/or away from the patient support assembly. In some embodiments, one or more of the back rest, the head rest, the arm rest, the seat member, the shin rest, and/or the foot brace (e.g., heel stop) moves to guide the patient to facilitate emergency egress of the patient out of the patient support and/or away from the patient support assembly. The emergency patient evacuation system disclosed herein (e.g., comprising a low voltage battery electrically coupled with at least one relay) electrically powers the actuators and brakes for assisting emergency egress of a patient from the patient support.

In some embodiments, the configurable patient support 110 is configured to move to a static configuration for emergency egress of a patient out of the patient support and/or away from the patient support assembly, e.g., the configurable patient support is configured to move to a patient emergency egress state, e.g., to provide a static configuration that is a patient emergency egress state. The patient support configured in the patient emergency egress state comprises the back rest, the head rest, the arm rest, the seat member, the shin rest, and/or the foot brace (e.g., heel stop) in positions that facilitate emergency egress of the patient out of the patient support and/or away from the patient support assembly in case of power loss and/or other emergency. For example, the back rest, the head rest, the arm rest, the seat member, the shin rest, and/or the foot brace (e.g., heel stop) are in positions that allow easy movement of the patient away from the patient support and do not hinder emergency egress of the patient from the patient support. In some embodiments, the patient emergency egress state is configured to facilitate emergency egress of a patient in a standing position. In some embodiments, the patient emergency egress state is configured to facilitate emergency egress of a patient in a sitting position, e.g., by assisting a patient to stand and move out of the patient support and/or away from the patient support assembly. The emergency patient evacuation system disclosed herein (e.g., comprising a low voltage battery electrically coupled with at least one relay) electrically powers the actuators and brakes to provide the patient support in an emergency egress configuration.

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in the art are intended to be within the scope of the following claims.

We claim:

1. A patient positioning system comprising a configurable patient support comprising a back rest; a seat member; a shin rest; and/or a heel stop,
    wherein the back rest is operatively engaged with a back rest motor to provide a motorized back rest, the seat member is operatively engaged with a seat member motor to provide a motorized seat member, the shin rest is operatively engaged with a shin rest motor to provide a motorized shin rest, and/or the heel stop is operatively engaged with a heel stop motor to provide a motorized heel stop;
    wherein the motorized back rest, the motorized seat member, the motorized shin rest, and/or motorized heel stop is configured to operatively engage a patient to apply a force to the patient to facilitate patient movement; and
    wherein the patient positioning system further comprises a weight sensor and the force applied to the patient is calculated using a weight of the patient measured by the weight sensor.

2. The patient positioning system of claim 1, wherein the configurable patient support comprises at least three of a back rest; a seat member; a shin rest; and/or a heel stop.

3. The patient positioning system of claim 1, wherein the configurable patient support comprises a back rest; a seat member; a shin rest; and a heel stop.

4. The patient positioning system of claim 1, wherein the configurable patient support is provided in a configuration associated with a specific patient or patient class.

5. The patient positioning system of claim 1, wherein the configurable patient support is provided in a configuration associated with a specific imaging or treatment plan.

6. The patient positioning system of claim 1, wherein the configurable patient support is provided in a configuration for patient ingress.

7. The patient positioning system of claim 1, wherein the configurable patient support is provided in a configuration for patient egress.

8. The patient positioning system of claim 1, wherein the configurable patient support is provided in a configuration for patient imaging and/or treatment.

9. The patient positioning system of claim 1, wherein the configurable patient support is provided in a standby configuration.

10. The patient positioning system of claim 1, wherein the configurable patient support is configured to support a patient in an upright position.

11. The patient positioning system of claim 10, wherein the upright position is a standing, sitting, or perched position.

12. The patient positioning system of claim 1, wherein the configurable patient support further comprises arm rests.

13. The patient positioning system of claim 1, further comprising a microprocessor configured to coordinate movement of the motorized back rest, the motorized seat member, the motorized shin rest, and/or the motorized heel stop.

14. The patient positioning system of claim 13, further comprising non-volatile storage medium readable by the microprocessor.

15. The patient positioning system of claim 14, wherein the patient positioning system is configured according to a stored configuration previously recorded in the non-volatile storage medium.

16. The patient positioning system of claim 1, wherein the patient support is configured to rotate a patient around a vertical or substantially vertical axis with respect to a static radiation source.

17. The patient positioning system of claim 1, wherein the patient support is offset from a vertical axis of rotation such that a torso of a patient secured to the configurable patient support is aligned with the vertical axis of rotation.

* * * * *